US009588122B2

(12) United States Patent
Chang et al.

(10) Patent No.: US 9,588,122 B2
(45) Date of Patent: Mar. 7, 2017

(54) METHODS OF TREATING CANCER SENSITIVE TO ANTI-EGFR THERAPY AND MODIFYING TREATMENT USING PEROXIREDOXIN 6 BIOMARKER

(71) Applicant: The Board of Trustees of the Leland Stanford Junior University, Palo Alto, CA (US)

(72) Inventors: Edwin Chang, Menlo Park, CA (US); Lingyun Xu, Fremont, CA (US); Nick Hughes, Orinda, CA (US); Carsten H. Nielsen, Copenhagen N (DK); Sanjiv S. Gambhir, Portola Valley, CA (US); Parag Mallick, San Mateo, CA (US); Arutselvan Natarajan, Sunnyvale, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 93 days.

(21) Appl. No.: 14/206,223

(22) Filed: Mar. 12, 2014

(65) Prior Publication Data
US 2014/0275073 A1 Sep. 18, 2014

Related U.S. Application Data

(60) Provisional application No. 61/777,905, filed on Mar. 12, 2013.

(51) Int. Cl.
*G01N 33/50* (2006.01)
*G01N 33/574* (2006.01)
*A61K 31/517* (2006.01)
*A61K 31/5377* (2006.01)

(52) U.S. Cl.
CPC ..... *G01N 33/57488* (2013.01); *A61K 31/517* (2013.01); *A61K 31/5377* (2013.01); *G01N 33/57419* (2013.01); *G01N 33/57423* (2013.01); *G01N 33/57434* (2013.01); *G01N 33/57438* (2013.01); *G01N 2333/902* (2013.01)

(58) Field of Classification Search
None
See application file for complete search history.

(56) References Cited

U.S. PATENT DOCUMENTS 9,205,091 B2 * 12/2015 Maciag .............. A61K 31/4965

OTHER PUBLICATIONS

Berg et al., Biochemistry, 5th edition, New York: W H Freeman; 2002. Section 4.3, Immunology Provides Important Techniques with Which to Investigate Proteins. Retrieved from: http://www.ncbi.nlm.nih.gov/books/NBK22420/ on Oct. 26, 2015.*

(Continued)

*Primary Examiner* — Claire Kaufman
(74) *Attorney, Agent, or Firm* — Thomas | Horstemeyer, LLP

(57) ABSTRACT

The present disclosure provides methods of treating cancer and modifying a cancer treatment for a cancer with an anti-EGFR drug by creating PRDX6 expression profiles and using the profiles to evaluate and optionally modify treatment. The present disclosure also provides assays and systems for assessing sensitivity of a cancer to an anti-EGFR therapy.

15 Claims, 21 Drawing Sheets

(56) References Cited

OTHER PUBLICATIONS

Wang et al., Preclinical pharmacokinetic/pharmacodynamic models of gefitinib and the design of equivalent dosing regimes in EGFR wild-type and mutant tumor modles, Mol. Canc. Ther. 7(2):407-417, 2008.*
Stanford Reference 13-017, Blood biomarkers for monitoring response to anti-EGFR therapy, Stanford University Office of Technology Licensing [online], [retrieved Jul. 25, 2016], Retrieved from the Internet <URL:http://techfinder.stanford.edu/technology_detail.php?ID=29991>..*
Zhang et a;/. Triosephophate isomerase and peroxiredoxin 6, two novel serum markers for humanlung squamous cell carcinoma, Canc. Sci. 100(12):2396-2401, Dec. 2009.*
Thomson S, Petti F, Sujka-Kwok I, Epstein D, Haley JD. Kinase switching in mesenchymal-like non-small cell lung cancer lines contributes to EGFR inhibitor resistance through pathway redundancy. Clin Exp Metastasis. 2008;25:843-54.
Ullrich A, Coussens L, Hayflick JS, Dull TJ, Gray A, Tam AW, et al. Human epidermal growth factor receptor cDNA sequence and aberrant expression of the amplified gene in A431 epidermoid carcinoma cells. Nature. 1984;309:418-25.
Ullrich A, Riedel H, Yarden Y, Coussens L, Gray A, Dull T, et al. Protein kinases in cellular signal transduction: tyrosine kinase growth factor receptors and protein kinase C. Cold Spring Harb Symp Quant Biol. 1986;51 Pt 2:713-24.
Wakeling AE, Guy SP, Woodburn JR, Ashton SE, Curry BJ, Barker AJ, et al. ZD1839 (Iressa): an orally active inhibitor of epidermal growth factor signaling with potential for cancer therapy. Cancer Res. 2002;62:5749-54.
Xu, Y.H., Richert, N., Ito, S., Merlino, G.T. & Pastan, I. Characterization of epidermal growth factor receptor gene expression in malignant and normal human cell lines. Proceedings of the National Academy of Sciences of the United States of America 81, 7308-7312 (1984).
Yang HS, Matthews CP, Clair T, Wang Q, Baker AR, Li CC, et al. Tumorigenesis suppressor Pdcd4 down-regulates mitogen-activated protein kinase kinase kinase kinase 1 expression to suppress colon carcinoma cell invasion. Mol cell Biol. 2006;26:1297-306.
Yauch RL, Januario T, Eberhard DA, Cavet G, Zhu W, Fu L, et al. Epithelial versus mesenchymal phenotype determines in vitro sensitivity and predicts clinical activity of erlotinib in lung cancer patients. Clin Cancer Res. 2005;11:8686-98.
Yun CH, Mengwasser KE, Toms AV, Woo MS, Greulich H, Wong KK, et al. The T790M mutation in EGFR kinase causes drug resistance by increasing the affinity for ATP. Proc Natl Acad Sci U S A. 2008;105:2070-5.
Zang X, Pickin KA, Bose R, Jura N, Cole PA, Kuriyan J. Inhibition of the EGF receptor by binding of MIG6 to an activating kinase domain interface. Nature. 2007;450:741-4.
Zang Y, Xiang L, Hassan R, Paik CH, Carrasquillo JA, Jang BS, et al. Synergistic antitumor activity of taxol and Immunotoxin SS1P in tumor-bearing mice. Clin Cancer Res. 2006;12:4695-701.
Zhou Y, Aebersold R, Zhang H. Isolation of N-linked glycopeptides from plasma. Anal Chem. 2007;79:5826-37.
Albers, M., et al. Automated yeast two-hybrid screening for nuclear receptor-interacting proteins. Molecular & cellular proteomics : MCP 4, 205-213 (2005).
Amann, J., et al. Aberrant epidermal growth factor receptor signaling and enhanced sensitivity to EGFR inhibitors in lung cancer. Cancer research 65, 226-235 (2005).
Anderson, P.D., et al. Nkx3.1 and Myc crossregulate shared target genes in mouse and human prostate tumorigenesis. The Journal of clinical investigation 122, 1907-1919 (2012).
Barsnes H, Vizcaino JA, Eidhammer I, Martens L. PRIDE Converter: making proteomics data-sharing easy. Nat Biotechnol. 2009;27:598-9.

Beck, H.C., et al. Proteomic profiling of human colon cancer cells treated with the histone deacetylase inhibitor belinostat. Electrophoresis 31, 2714-2721 (2010).
Bland, J.M. & Altman, D.G. Comparisons within randomised groups can be very misleading. British Medical Journal 342(2011).
Bryant JA, Finn RS, Slamon DJ, Cloughesy TF, Charles AC. EGF activates intracellular and intercellular calcium signaling by distinct pathways in tumor cells. Cancer Biol Ther. 2004;3:1243-9.
Calvano SE, Xiao W, Richards DR, Felciano RM, Baker HV, Cho RJ, et al. A network based analysis of systemic Inflammation in humans. Nature. 2005;437:1032-7.
Citri A, Yarden Y. EGF-ERBB signalling: towards the systems level. Nat Rev Mol Cell Biol. 2006;7:505-16.
Cohen MH, Williams GA, Sridhara R, Chen G, Pazdur R. FDA drug approval summary: gefitinib (ZD1839) (Iressa) tablets. Oncologist. 2003;8:303-6.
Cummings RD, Soderquist AM, Carpenter G. The oligosaccharide moieties of the epidermal growth factor receptor in A-431 cells. Presence of complex-type N-linked chains that contain terminal N-acetylgalactosamine residues. J Biol Chem. 1985;260:11944-52.
Dannenberg, J.H., et al. mSin3A corepressor regulates diverse transcriptional networks governing normal and neoplastic growth and survival. Genes & development 19, 1581-1595 (2005).
Dennis G, Jr., Sherman BT, Hosack DA, Yang J, Gao W, Lane HC, et al. DAVID: Database for Annotation, Visualization, and Integrated Discovery. Genome Biol. 2003;4:P3.
Deutsch EW, Eng JK, Zhang H, King NL, Nesvizhskii AI, Lin B, et al. Human Plasma PeptideAtlas. Proteomics. 2005;5:3497-500.
Di Fiore PP, Pierce JH, Fleming TP, Hazan R, Ullrich A, King CR, et al. Overexpression of the human EGF receptor confers an EGF-dependent transformed phenotype to Nih 3T3 cells. Cell. 1987;51:1063-70.
Eisenhauer, E.A., et al. New response evaluation criteria in solid tumours: revised RECIST guideline (version 1.1). Eur. J Cancer 45, 228-247 (2009).
Engelman JA, Janne PA. Mechanisms of acquired resistance to epidermal growth factor receptor tyrosine kinase inhibitors in non-small cell lung cancer. Clin Cancer Res. 2008;14:2895-9.
Engelman JA, Zejnullahu K, Mitsudomi T, Song Y, Hyland C, Park JO, et al. MET amplification leads to gefitinib resistance in lung cancer by activating ERBB3 signaling. Science. 2007;316:1039-43.
Faca V, Pitted SJ, Newcomb L, Glukhova V, Phanstiel D, Krasnoselsky A, et al. Contribution of protein fractionation to lepth of analysis of the serum and plasma proteomes. J Proteome Res. 2007;6:3558-65.
Fang Q, Kani K, Faca VM, Zhang W, Zhang Q, Jain A, et al. Impact of protein stability, cellular localization, and abundance on proteomic detection of tumor-derived proteins in plasma. PLoS One 2011;6:e23090.
Fernandes H, Cohen S, Bishayee S. Glycosylation-induced conformational modification positively regulates receptor-receptor association: a study with an aberrant epidermal growth factor receptor (EGFRvIII/DeltaEGFR) expressed in cancer cells. J Biol Chem. 2001;276:5375-83.
Frederick BA, Helfrich BA, Coldren CD, Zheng D, Chan D, Bunn PA, Jr., et al. Epithelial to mesenchymal transition predicts gefitinib resistance in cell lines of head and neck squamous cell carcinoma and non-small cell lung carcinoma. Mol Cancer Ther. 2007;6:1683-91.
Gao, H., Falt, S., Sandelin, A., Gustafsson, J.A. & Dahlman-Wright, K. Genome-wide identification of estrogen receptor alpha-binding sites in mouse liver. Molecular endocrinology (Baltimore, Md.) 22, 10-12 (2008).
Gaster, R.S., et al. Matrix-insensitive protein assays push the limits of biosensors in medicine. Nat Med 15, 1327-1332 (2009).
Guo A, Villen J, Kornhauser J, Lee KA, Stokes MP, Rikova K, et al. Signaling networks assembled by oncogenic EGFR and c-Met. Proc Natl Acad Sci U S A. 2008;105:692-7.
Hanash, S.M., Baik, C.S. & Kallioniemi, O. Emerging molecular biomarkers—bloodbased strategies to detect and monitor cancer. Nature reviews. Clinical oncology 8, 142-50 (2011).
Harari PM. Epidermal growth factor receptor inhibition strategies in oncology. Endocr Relat Cancer. 2004;11:689-708.

(56) References Cited

OTHER PUBLICATIONS

Kani, K., et al. Quantitative proteomic profiling identifies protein correlates to EGFR kinase inhibition. Molecular cancer therapeutics 11, 1071-1081 (2012).

Keller A, Nesvizhskii Al, Kolker E, Aebersold R. Empirical statistical model to estimate the accuracy of peptide identifications made by MS/MS and database search. Anal Chem. 2002;74:5383-92.

Kidder, B.L., Yang, J. & Palmer, S. Stat3 and c-Myc genome-wide promoter occupancy in embryonic stem cells. PloS one 3, e3932 (2008).

Kobayashi, S., et al. EGFR mutation and resistance of non-small-cell lung cancer to gefitinib. N. Engl J Med 352, 786-792 (2005).

Lee, T.H., et al. Characterization of the murine gene encoding 1-Cys peroxiredoxin and identification of highly homologous genes. Gene 234, 337-344 (1999).

Ling YH, Li T, Perez-Soler R, Haigentz M, Jr. Activation of ER stress and inhibition of EGFR N-glycosylation by tunicamycin enhances susceptibility of human non-small cell lung cancer cells to erlotinib. Cancer Chemother Pharmacol. 2009;64:539-48.

Liu H, Liu ZQ, Chen CX, Magill S, Jiang Y, Liu YJ. Inhibitory regulation of EGF receptor degradation by sorting nexin 5. Biochem Biophys Res Commun. 2006;342:537-46.

Maemondo, M., et al. Gefitinib or chemotherapy for non-small-cell lung cancer with mutated EGFR. N Engl J Med 362, 2380-2388 (2010).

Mok, T.S., et al. Gefitinib or carboplatin-paclitaxel in pulmonary adenocarcinoma. N Engl J Med 361, 947-957 (2009).

Morandell S, Stasyk T, Skvortsov S, Ascher S, Huber LA. Quantitative proteomics and phosphoproteomics reveal novel insights into complexity and dynamics of the EGFR signaling network. Proteomics. 2008;8:4383-401.

Myers MV, Manning HC, Coffey RJ, Liebler DC. Protein expression signatures for inhibition of epidermal growth factor receptor mediated signaling. Mol Cell Proteomics. 2011.

Nesvizhskii Al, Keller A, Kolker E, Aebersold R. A statistical model for identifying proteins by tandem mass spectrometry. Anal Chem. 2003;75:4646-58.

Oyama M, Kozuka-Hata H, Tasaki S, Semba K, Hattori S, Sugano S, et al. Temporal perturbation of tyrosine phosphoproteome dynamics reveals the system-wide regulatory networks. Mol Cell Proteomics. 2009;8:226-31.

Pao W, Miller VA, Politi KA, Riely GJ, Somwar R, Zakowski MF, et al. Acquired resistance of lung adenocarcinomas to gefitinib or erlotinib is associated with a second mutation in the EGFR kinase domain. PLoS Med. 2005;2:e73.

Pao, W. & Chmielecki, J. Rational, biologically based treatment of EGFR-mutant nonsmall—cell lung cancer. Nature reviews. Cancer 10, 760-774 (2010).

Rauch A, Bellew M, Eng J, Fitzgibbon M, Holzman T, Hussey P, et al. Computational Proteomics Analysis System (CPAS): an extensible, open-source analytic system for evaluating and publishing proteomic data and high throughput biological experiments. J Proteome Res. 2006;5:112-21.

Rho JK, Choi YJ, Lee JK, Ryoo BY, Na, II, Yang SH, et al. Epithelial to mesenchymal transition derived from repeated exposure to gefitinib determines the sensitivity to EGFR inhibitors in A549, a non-small cell lung cancer cell line. Lung Cancer. 2009;63:219-26.

Riely GJ. The use of first-generation tyrosine kinase inhibitors in patients with NSCLC and somatic EGFR mutations. Lung Cancer 2008;60 Suppl 2:S19-22.

Rosell, R., et al. Screening for epidermal growth factor receptor mutations in lung cancer N. Engl J Med 361, 958-967 (2009).

Rubin BP, Duensing A. Mechanisms of resistance to small molecule kinase inhibition in the treatment of solid tumors. Lab Invest. 2006;86:981-6.

Sequist, L.V., et al. Genotypic and histological evolution of lung cancers acquiring resistance to EGFR inhibitors. Sci Transl Med 3, 75ra26 (2011).

Slamon DJ, Clark GM, Wong SG, Levin WJ, Ullrich A, McGuire WL. Human breast cancer: correlation of relapse and survival with amplification of the HER-2/neu oncogene. Science. 1987;235:177-82.

Sordella R, Bell DW, Haber DA, Settleman J. Gefitinib-sensitizing EGFR mutations in lung cancer activate anti-apoptotic pathways. Science. 2004;305:1163-7.

\* cited by examiner gefitinib erlotinib

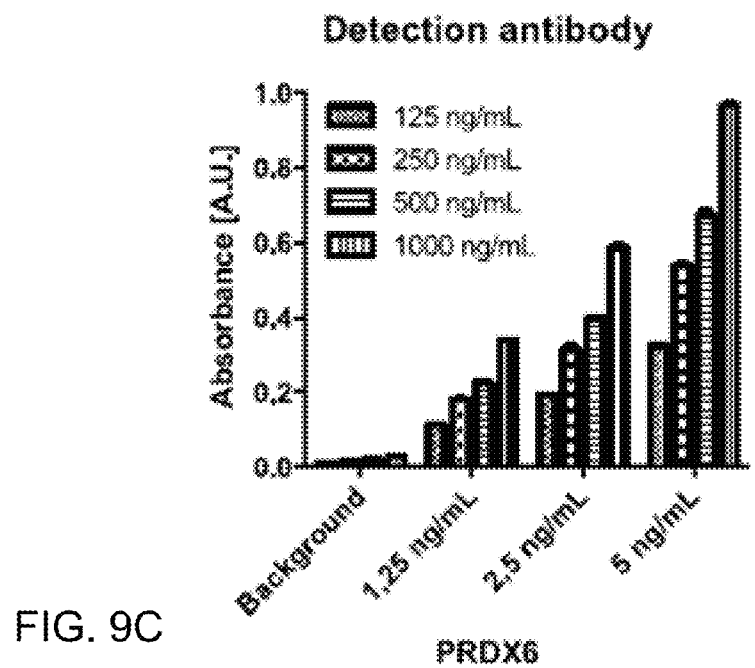
FIG. 9C
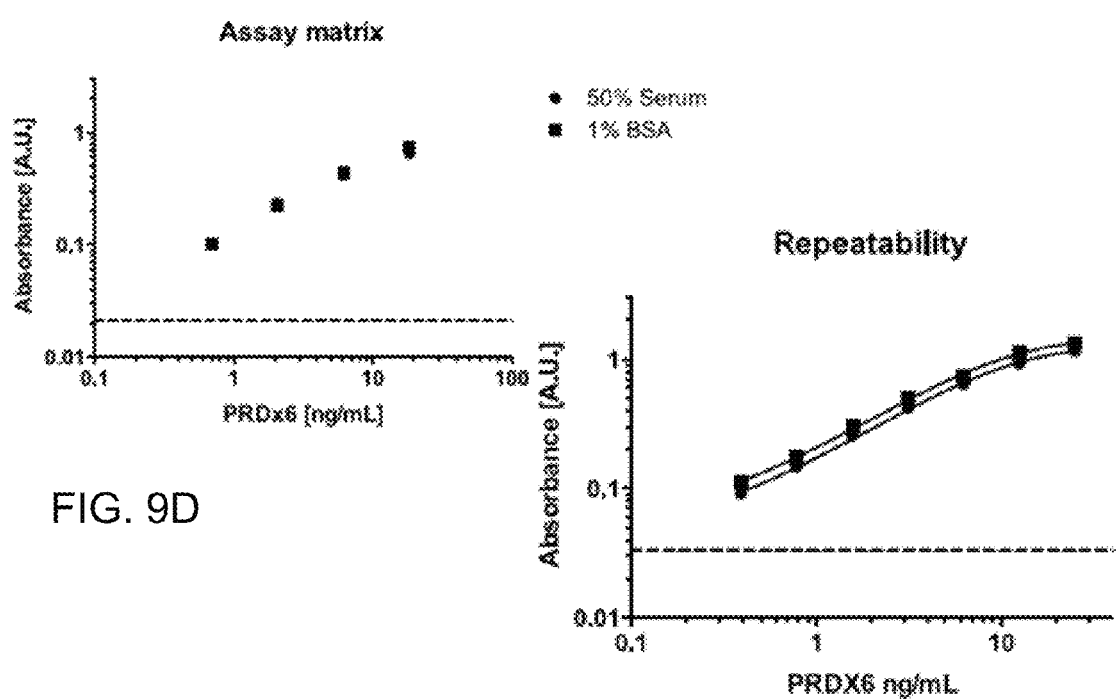
FIG. 9D
FIG. 9E

METHODS OF TREATING CANCER SENSITIVE TO ANTI-EGFR THERAPY AND MODIFYING TREATMENT USING PEROXIREDOXIN 6 BIOMARKER

CROSS-REFERENCE TO RELATED APPLICATIONS

This application claims the benefit of and priority to U.S. Provisional Application Ser. No. 61/777,905, having the title "Methods of Modifying Anti-EGFR Cancer Treatment Using Blood Biomarkers," filed on Mar. 12, 2013, the disclosure of which is incorporated herein in by reference in its entirety.

STATEMENT OF GOVERNMENTAL SUPPORT

This invention was made with government support under contracts CA119367 and CA151459 awarded by the National Institutes of Health. The government has certain rights in the invention.

BACKGROUND

Targeted therapies directed against key oncogenic targets offer considerable promise for the treatment of cancer. For many targeted therapies however, it is not possible to predict how a given patient will respond to treatment. As a result, oncologists must monitor response to therapy, such that patients who do not respond can quickly be switched to an alternative treatment regimen. If a patient does respond, a second problem then arises: how best to detect the onset of resistance as early as possible during the course of treatment. Such "early resistance detection" is an important clinical problem, and one that has been relatively unexplored to date. In this regard, the use of anti-EGFR therapeutics in cancers such as non-small cell lung cancer (NSCLC) provides a compelling example of the challenges facing oncologists in managing patients who will inevitably acquire resistance to treatment.

Patients with NSCLC exhibiting specific mutations in the EGFR domain often show a significant response to the anti-EGFR tyrosine kinase inhibitors (TKIs), such as gefitinib (Iressa®) and erlotinib (Tarceva®). Estimates indicate over 70% of NSCLC patients with EGFR-mutant tumors show a decrease in tumor burden following treatment with either of the aforementioned TKIs. However, lung tumors in patients treated with these agents often eventually acquire resistance to this form of therapy, with a median time to treatment failure of ten months. Once therapeutic resistance develops, the treatment regimen should be re-evaluated as soon as possible, and potentially modified. Modification may include switching the patient to a different therapy or stopping treatment with the anti-EGFR TKI for a period of time in the hope of re-sensitizing the tumor to the original therapy.

Presently, the dominant approach to therapy monitoring in the clinic is based on the use of serial imaging scans during treatment. In the case of NSCLC patients receiving anti-EGFR therapy, computed tomography (CT) scans are typically performed every two months. Despite the wide spread use of imaging to monitor treatment response, it suffers from a number of serious drawbacks that ultimately limits its effectiveness. Specifically, imaging scans are time-intensive, relatively costly, and, in the case of CT, expose the patient to ionizing radiation. Furthermore, the molecular changes that drive therapeutic response and the development of resistance may occur sometime before their effects are apparent on imaging or morphological imaging (using, for example, the standard RECIST criteria).

SUMMARY

Briefly described, embodiments of the present disclosure provide methods and systems, for treating cancer in a subject and/or determining sensitivity or resistance of a cancer in a subject, and cancer sensitivity assays for testing samples from a subject.

Embodiments of methods of treating cancer in a subject according to the present disclosure include the following steps: determining a pre-treatment level of peroxiredoxin 6 (PRDX6) protein in a sample taken from a subject having a cancer predicted to be sensitive to anti-epidermal growth factor receptor (EGFR) treatment; initiating a treatment regimen for the subject with an anti-EGFR drug, the treatment involving administering one or more doses of the anti-EGFR drug to the subject over a period of time; determining a second level of PRDX6 in a second sample taken from the subject no later than about 4 weeks after the initial treatment with the anti-EGFR drug; and creating a PRDX6 expression profile for the subject that compares the pre-treatment and second PRDX6 levels relative to the anti-EGFR treatment regimen. Exemplary methods also include optionally determining one or more subsequent levels of PRDX6 in samples taken from the subject after the second sample; updating the PRDX6 expression profile for the subject to include any subsequent PRDX6 levels; using the PRDX6 expression profile to evaluate efficacy of the anti-EGRF drug in reducing tumor volume; and continuing, modifying, or discontinuing the treatment regimen with the anti-EGFR drug based on the PRDX6 expression profile.

The present disclosure also provides methods of determining sensitivity or resistance of a cancer in a subject to an anti-EGFR drug. In embodiments, such methods include: determining a pre-treatment level of PRDX6 protein in a sample taken from a subject having cancer; providing one or more doses of an anti-EGFR drug to the subject over a period of time; determining a second level of PRDX6 in a sample taken from the subject no later than about 4 weeks after an initial treatment with the anti-EGFR drug; creating a PRDX6 expression profile comparing the pre-treatment level of PRDX6 with the second level of PRDX6, relative to the anti-EGFR treatment regimen; and determining sensitivity or potential non-responsiveness or resistance of the cancer to the anti-EGFR drug based on the PRDX6 expression profile.

In embodiments, the present disclosure also includes in vitro methods of determining sensitivity or resistance of a cancer in a subject to an anti EGFR drug. Embodiments of such methods include: obtaining a biopsy sample of cancer cells from a subject; growing the cancer cells in culture; determining a level of PRDX6 protein produced by the cells; exposing the cancer cells to the anti-EGFR drug; determining a second level of PRDX6 protein produced by the cells between about 10 and about 24 hours after exposing the cells to the anti-EGFR drug; creating a PRDX6 expression profile for the cells comparing the first level of PRDX6 to the second level of PRDX6; and determining sensitivity of the cancer to the anti-EGFR drug, resistance of the cancer to the anti-EGFR drug, or an inconclusive result, based on the PRDX6 expression profile.

The present disclosure also provides cancer sensitivity assays. In embodiments, cancer sensitivity assays of the present disclosure includes the following: a sample obtained from a subject having a cancer predicted to be sensitive to an anti-EGFR treatment, where the sample is taken before initiation of an anti-EGFR treatment regimen with an anti-EGFR drug or sometime during the anti-EGFR treatment regimen; a capture antibody specific for PRDX6 protein; and a detection antibody capable of binding PRDX6. In other embodiments, a cancer sensitivity assay of the present disclosure includes the following: a sample of cancer cells obtained from a subject; culture medium for growing the cells; an anti-EGFR drug used for treatment of cancer; a capture antibody specific for PRDX6 protein; and a detection antibody capable of binding PRDX6.

Other methods, compositions, plants, features, and advantages of the present disclosure will be or become apparent to one with skill in the art upon examination of the following drawings and detailed description. It is intended that all such additional compositions, methods, features, and advantages be included within this description, and be within the scope of the present disclosure.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1A illustrates the chemical structure of gefitinib (top) and erlotinib (bottom). FIG. 1B illustrates total protein identifications based on compartment with a PeptideProphet score≥0.9 and ProteinProphet score of ≥0.90. FIG. 1C is a histogram of ($log_2$) fold change versus unique protein identifications for the 2 hr and 16 hr treatments and shows quantitative changes in A431 proteomes were greater after 16 hours.

FIG. 2A illustrates the fold change of candidate biomarkers given as a function of compartment of identification with 16 hour gefitinib treatment. Proteins identified by cell-surface capture are depicted by rounded rectangles while proteins identified in the whole cell lysate are ellipses. Normalized fold change for each protein is given numerically and by the grayscale heat-map. FIG. 2B illustrates densitometry analysis for three independent biological replicate; experiments are listed below each immunoblot.

FIG. 3A shows the tumor growth curve for A431 xenografts in animals treated with 50 mg/kg gefitinib or left untreated and the tumor growth curve for gefitinib-resistant tumors (A431-ZDR) in animals treated with 50 mg/kg gefitinib or left untreated. FIG. 3B illustrates analysis by immunoblot of tumor lysates generated from A431 xenografts for the 16 proteins in the panel. Lysates were fractionated to enrich for soluble and insoluble proteins.

FIGS. 5A and 5B illustrate PRDX6 levels in cell media over the course of 32 hours after treatment for A431 and HCC827 cells, respectively.

FIG. 6A is a graph illustrating tumor growth curves (treatment initiated on day 1). FIG. 6B is a bar graph showing the amount of phospho-EGFR (normalized to total protein) in tumor lysates collected on day 15.

FIGS. 7A and 7B illustrate tumor growth curves (treatment initiated on day 1) for HCC827 and H1975 xenografts, respectively. FIGS. 7C and 7D illustrate serum PRDX6 levels in naïve (pre-inoculation), Day 0 (pre-treatment), Day 4 (post-treatment) and Day 15 (post-treatment) blood samples. FIGS. 7E and 7F are bar graphs of serum PRDX6 levels normalized to tumor volume. All error bars represent one standard error of the mean.

FIG. 8A is a bar graph showing mean serum PRDX6 levels from naïve (all mice), pre-treatment (all mice), and multiple early post-treatment blood samples (groups of 5 mice). FIG. 8B illustrates mean change from baseline in serum PRDX6 levels for paired pre- and post-treatment samples. FIG. 8C is a graph of mean change from baseline in tumor volume for vehicle and gefitinib-treated animals, and FIG. 8D is a graph of mean change from baseline in serum PRDX6 levels normalized to tumor volume for paired pre- and post-treatment samples. All error bars represent one standard error of the mean.

FIGS. 9A-9E illustrate the development of an embodiment of a PRDX6 sandwich ELISA. The antibody pair sc-59671:ab73350 yielded the highest signal (FIG. 9A), and a concentration of 1 μg/mL of both capture and detection antibody gave the best performance (FIGS. 9B-9C). The optimized ELISA was able to measure PRDX6 in the presence of 50% mouse serum (FIG. 9D) and showed a high degree of repeatability with sensitivity below 0.4 ng/mL (FIG. 9E). Dashed lines indicate the background readings.

FIGS. 12A-12B are graphs illustrating the ratio of shed biomarker (Iressa®/Vehicle) vs. $IC_{50}$ to Iressa®, and FIGS. 12D-12F are graphs of the area under the curve (AUC) vs. $IC_{50}$ to Iressa®, for PRDX6 (FIGS. 12A and 12D), EpCAM (FIGS. 12B and 12E), and cMET (FIGS. 12C and 12F).

DETAILED DESCRIPTION

Figure 1A:
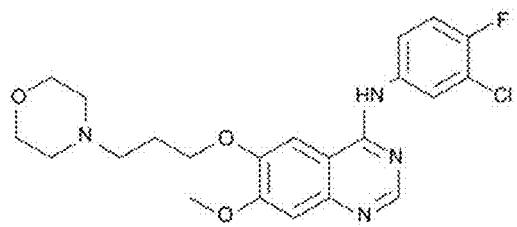
FIGS. 1A-1C illustrate sub-proteome analysis of A431 cells with and without gefitinib treatment.
Figure 1A:
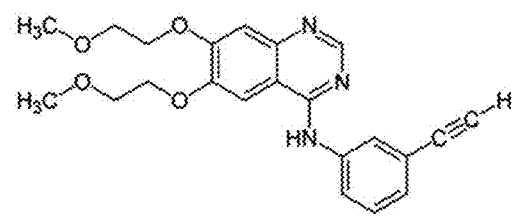

The details of some embodiments of the present disclosure are set forth in the description below. Other features, objects, and advantages of the present disclosure will be apparent to one of skill in the art upon examination of the following description, drawings, examples and claims. It is intended that all such additional systems, methods, features, and advantages be included within this description, be within the scope of the present disclosure, and be protected by the accompanying claims Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, medicine, oncology, organic chemistry, biochemistry, bioengineering, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

DEFINITIONS

In describing and claiming the disclosed subject matter, the following terminology will be used in accordance with the definitions set forth below.

The term "cancer", as used herein, shall be given its ordinary meaning, as a general term for diseases in which abnormal cells divide without control and form cancer or neoplastic cells or tissues. The term cancer can include cancer cells and/or precancerous cells. In particular, and in the context of the embodiments of the present disclosure, cancer refers to angiogenesis-related cancer. Cancer cells can invade nearby tissues and can spread through the bloodstream and lymphatic system to other parts of the body. There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

When normal cells lose their ability to behave as a specified, controlled and coordinated unit, a tumor may be formed. Generally, a solid tumor is an abnormal mass of tissue that usually does not contain cysts or liquid areas (although some brain tumors do have cysts and central necrotic areas filled with liquid). A single tumor may even have different populations of cells within it, with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors.

Representative cancers include, but are not limited to, bladder cancer, breast cancer, colorectal cancer, endometrial cancer, head and neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease, leukemia, acute lymphoblastic leukemia, acute myeloid leukemia, liver cancer, medulloblastoma, neuroblastoma, brain tumors generally, non-Hodgkin's lymphoma, osteosarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer, among others. In embodiments, the cancer is selected from anti-EGFR sensitive cancers, such as, but not limited to: non-small-cell lung cancer (NSCLC), colorectal cancers, pancreatic cancer, and prostate cancer.

A tumor can be classified as malignant or benign. In both cases, there is an abnormal aggregation and proliferation of cells. In the case of a malignant tumor, these cells behave more aggressively, acquiring properties of increased invasiveness. Ultimately, the tumor cells may even gain the ability to break away from the microscopic environment in which they originated, spread to another area of the body (with a very different environment, not normally conducive to their growth), and continue their rapid growth and division in this new location. This is called metastasis. Once malignant cells have metastasized, achieving a cure is more difficult.

Benign tumors have less of a tendency to invade and are less likely to metastasize. Brain tumors spread extensively within the brain but do not usually metastasize outside the brain. Gliomas are very invasive inside the brain, even crossing hemispheres. They do divide in an uncontrolled manner, though. Depending on their location, they can be just as life threatening as malignant lesions. An example of this would be a benign tumor in the brain, which can grow and occupy space within the skull, leading to increased pressure on the brain.

It should be noted that precancerous cells, cancer, tumors may be used interchangeably in the art.

"Epidermal Growth Factor Receptor" or "EGFR" is a member of the ErbB/HER family of tyrosine kinase receptors, which also includes ErbB2, clinically referred to as HER-2/neu. It is a receptor for Epidermal Growth Factor "EGF", which is implicated in many forms of cancer where the proper response to EGF levels is defective resulting, among other things, in overgrowth of cancer cells.

As used herein "anti-EGFR therapy" or "anti-EGFR treatment" includes treatment of certain EGFR-sensitive disorders, including certain cancers, with compounds that interfere with the EGFR pathway (e.g., by blocking the receptor or otherwise interfering with receptor binding to EGF), also called "anti-EGFR drugs". Representative compounds include, but are not limited to, monoclonal antibodies (MoAbs) and small molecule tyrosine kinase inhibitors (smTKIs) against EGFR. An "anti-EGFR drug" or anti-EGFR compound" includes drugs/compounds that target/antagonize the epidermal growth factor receptor (EGFR) or otherwise interfere with receptor, ligand interaction. Anti-EGFR drugs include, but are not limited to, the following: gefitinib (Iressa®) and erlotinib (Tarceva®). Anti-EGFR therapy has found application in cancers including NSCLC, colorectal cancer, pancreatic cancer, prostate cancer, and breast cancer, among others. An anti-EGFR therapy may include treatment with one or more anti-EGFR drugs alone or in combination with other therapeutic measures or other drugs.

As used in the present disclosure a cancer "sensitive to anti-EGFR therapy" includes cancers where there is a defect in EGF signaling. Cancers "sensitive to anti-EGFR therapy" and cancers "predicted to be sensitive to anti-EGFR therapy" includes cancers that have been successfully treated with anti-EGFR therapy or other cancers that show similar mechanism, thus providing a reasonable belief that such cancer would be sensitive to anti-EGFR therapy. Cancers "predicted to be sensitive to anti-EGFR therapy" includes cancers that, while they traditionally or initially display sensitivity to anti-EGFR therapy, may occasionally be resistant/non-responsive to anti-EGFR therapy or later develop (or be known to develop) resistance to the therapy. Representative cancers sensitive to anti-EGFR therapy include, but are not limited to, non-small cell lung cancer (NSCLC), colorectal cancers, pancreatic cancer, prostate cancer, and all three forms of breast cancer.

The terms "administer", "administering", or "administration", as used herein refer to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of the compound within the subject's body, or prescribing a compound or therapy to a subject even if the compound is taken by the subject themselves or given by an intermediary.

The term "initiating a treatment regimen for the subject" indicates providing a treatment plan for a subject and the time of initiation the treatment regimen for a subject is the time when the subject takes or is given the first dose of an anti-EGFR drug of the treatment.

The term "subject" as used herein includes, without limitation, an animal. In one embodiment, the animal is a vertebrate. In embodiments, the animal is a mammal. Representative mammals that can be subjects within the meaning of the present disclosure include, but are not limited to, a human, mouse, rat, guinea pig, dog, cat, horse, cow, pig, monkey, chimpanzee, baboon, and rhesus monkey.

As used herein, the term "pre-treatment level" refers to the level of a compound (e.g., a protein, lipid, small molecule, etc.) in a subject that is detected in a sample taken from the subject before or at the initiation of a treatment regimen. In embodiments, if the sample is taken before the initiation of a treatment regimen (e.g., with a drug, therapy, etc.), it is taken at a time sufficiently close to the beginning of treatment so that levels will not be expected to change significantly between the time of the sample and the initiation of treatment. Thus, for human subjects, it is likely that a pre-treatment level would be taken at the initiation of treatment (e.g., the same day) or no more than about a few days to one week prior to beginning treatment. A "pre-treatment level" of PRDX6 is the level of PRDX6 taken prior to or at the initiation of treatment of a subject with an anti-EGFR therapy/drug The term "PRDX6 expression profile" refers to an individualized profile reflecting the PRDX6 levels in a subject or a cell culture over time. A PRDX6 expression profile could also include a group profile reflecting the individual or average PRDX6 levels in a number of patients over time. In embodiments the profile shows the PRDX6 levels over a treatment period with an anti-EGFR drug and may also analyze the PRDX6 levels with respect to the treatment regimen (e.g., dosage, time, and the like), tumor size, and other information and/or data. In embodiments, the profile may be in graph format showing the levels of PRDX6 with respect to time, dosage of an anti-EGFR drug, and/or tumor size.

As used in the present disclosure, the term "modifying the treatment regimen" refers to adjusting a dosage of an anti-EGFR drug (e.g., amount of drug administered, dosage times, frequency of dosage, etc.) and can also include discontinuing a treatment regimen. The term "adjusting the dosage level" can include increasing, decreasing, or discontinuing the dosage of a drug. Increasing and decreasing the dosage level can include adjusting the dosage amount and/or the dosage intervals (timing).

ADDITIONAL ABBREVIATIONS

EpCAM, Epithelial cell adhesion molecule
c-MET, (MET or MNNG HOS Transforming gene) is a proto-oncogene that encodes a protein known as hepatocyte growth factor receptor (HGFR)
TXN, Thioredoxin
TROP2, Tumor-associated calcium signal transducer 2
SPOCK2, Testican-2
F3, Coagulation Factor III
MIF, Macrophage Migration Inhibitory Factor
CLDN1, Claudin 1
ANXA2, Annexin A2
PSAP, Prosaposin
FAM3C, family with sequence similarity 3, member C/"interleukin-like EMT inducer", "predicted osteoblast protein"
AKR1B1, aldo-keto reductase family 1, member B1 (aldose reductase)
CTSD, cathepsin D
LGALS3, lectin, galactoside-binding, soluble, 3
CALU, calumenin
HSPD1, heat shock 60 kDa protein 1 (chaperonin)
HDGF, hepatoma-derived growth factor
MANF/ARMET, mesencephalic astrocyte-derived neurotrophic factor
CALR, calreticulin
TPT1, tumor protein, translationally-controlled 1
Discussion The embodiments of the present disclosure encompass methods of treating cancer in a subject with an anti-EGFR treatment, methods of modifying an anti-EGFR treatment and detecting sensitivity and/or resistance to an anti-EGFR treatment, and assays and systems for detecting PRDX6 protein in a sample. Methods of the present disclosure include methods for modifying cancer treatment regimens, methods for treating cancer, methods for monitoring patient response to anti-EGFR cancer therapies, methods for determining sensitivity and/or resistance of cancers to anti-EGFR therapies, and methods for using determined levels of peroxiredoxin 6 (PRDX6) as a biomarker during treatment of a subject with anti-EGFR drugs to monitor and modify the treatment.

The methods of the present disclosure enable physicians to regularly monitor patient response to drugs that target the epidermal growth factor receptor (EGFR). A major use for these drugs is in cancer, and specifically the treatment of anti-EGFR sensitive cancers, such as, but not limited to, non-small cell lung cancer (NSCLC), colorectal cancer, breast cancer, pancreatic cancer, and prostate cancer.

Briefly described, the methods of the present disclosure involve measurement of certain biomarkers that are differentially expressed in response to anti-EGFR therapies in blood, by ELISA or any other suitable assays and monitoring response to anti-EGFR therapeutics. Changes in levels of these biomarkers during the course of therapy can be used to determine if the patient is responding to the anti-EGFR drug or has acquired resistance to it. Several biomarkers have been identified that appear to show differential expression in response to anti-EGFR drugs, including, but not limited to, peroxiredoxin 6 (PRDX6), beta-2-microglobulin (B2M), EpCAM, c-MET, TXN, CD166, TROP2, SPOCK2, F3, MIF, CLDN1, ANXA2, PSAP, FAM3C, AKR!B!, CTSD, LGALS3, CALU, HSPD1, HDGF, MANF/ARMET, CALR, and TPT1. One such biomarker is the protein peroxiredoxin 6 (PRDX6). A PRDX6 temporal signature of response to anti-EGFR therapies has been developed and validated in mouse models and human pre-clinical and clinical data, as discussed in greater detail in the examples below.

In contrast to in vivo imaging approaches, in vitro strategies based on blood biomarkers offer the potential to serve as effective tools for both short-term and long-term therapy. Blood samples can be taken regularly from patients during the course of treatment with relative ease, at minimal cost, and without exposing the patient to any significant risk. In addition, these samples can be analyzed quickly and inexpensively for multiple biomarkers using standard proteomic assays. At least one advantage of the methods of the present disclosure is that changes in the levels of biomarkers associated with key oncogenic processes appear to occur several weeks or months before a corresponding change in tumor size is detected on imaging. Thus, the methods of the present disclosure provide a blood biomarker strategy for monitoring response to anti-EGFR therapy, thus providing efficient methods for treating cancer by detecting and dealing with resistance earlier and with less invasive methods.

In exemplary embodiments, the methods of the present disclosure monitor changes in serum levels of the peroxiredoxin family member PRDX6 during the course of anti-EGFR therapy (e.g., gefitinib, erlotinib, and icontinib) to discriminate between anti-EGFR sensitive and anti-EGFR resistant tumors. Example 1 describes studies conducted to identify various candidate biomarkers (including PRDX6 and others) that demonstrate differential expression in response to anti-EGFR therapy. These compounds represent possible biomarkers in blood also appear to track response to anti-EGFR drugs. Thus, such biomarkers may be useful in methods for monitoring and modifying anti-EGFR treatment regimens for various forms of cancer, such as methods involving a panel of biomarkers.

Example 2 below describes the use of serial blood sampling from xenograft mouse models together with enzyme-linked immunosorbent assays (ELISAs) to quantify proteomic changes in serum and create a PRDX6 profile in response to an anti-EGFR drug. As discussed in greater detail in the example, the results illustrate the application of this approach for monitoring response to anti-EGFR therapy in cancer, both for early response assessment and for long-term monitoring to detect the onset of resistance.

Example 3 describes the relationship between the results from the cell culture studies and mouse model studies of Example 2 to human pre-clinical and clinical results, demonstrating that the human response tracks the mouse model and cell culture model, indicating the methods are applicable to human subjects. Example 3 also illustrates the ability to track PRDX6 levels during anti-EGFR treatment in human subjects to create a PRDX6 expression profile that provides information about the anti-EGFR treatment and allows modification of the treatment to optimize the efficacy of treatment.

The methods of the present disclosure offer a number of important advantages over traditional imaging-based approaches, including ease of sample collection, absence of ionizing radiation or other potential risks to patient safety, and low cost of sample analysis. It may have widespread applicability in the clinic, particularly for the treatment of NSCLC with erlotinib (Tarceva®), gefitinib (Iressa®), and icontinib.

In embodiments, the present disclosure includes methods of treating cancer in a subject by determining levels of certain anti-EGFR biomarkers in a sample (e.g., blood, tissue biopsy, etc.) from a subject and then providing and/or modifying a treatment regimen with an anti-EGFR therapy based on the profile of the biomarkers in the subject. In embodiments of the methods of the present disclosure, the biomarker is the peroxiredoxin 6 (PRDX6) protein, which is differentially expressed with respect to anti-EGFR drugs including, but not limited to, gefitinib, erlotinib, and icontinib. Thus, embodiments of methods of the present disclosure include determining levels of PRDX6 protein in a subject or a sample before treatment (pre-treatment level) and at various intervals after treatment with an anti-EGFR drug, such as one or more of the drugs listed above. In embodiments the determined levels of PRDX6 are used to provide a PRDX6 profile and the profile can be used to modify the treatment regimen with the anti-EGFR therapy, such as, but not limited to, adjusting dosage levels and/or times, determining sensitivity or resistance of the cancer to the anti-EGFR therapy, and/or continuing or discontinuing dosage with a drug, and the like.

In embodiments of the methods of the present disclosure, the cancers that can be treated and modified by the methods of the present disclosure include cancers that are sensitive to anti-EGFR therapy as well as cancers predicted to have sensitivity to anti-EGFR therapy. Exemplary cancers include, but are not limited to, non-small cell lung cancer (NSCLC) and colorectal cancers, pancreatic cancer, prostate cancer, and breast cancer. For instance, NSCLC is a leading cause of death in the US with approximately 220,000 new cases diagnosed per year, and approximately 160,000 deaths per year and only about a 15.6% 5-year survival rate. Approximately 15% of Stage IV NSCLC is characterized by overexpressed and dimerized EGFR. NSCLC has been shown to be sensitive to specific tyrosine kinase inhibitors to EGFR, including, but not limited to, Iressa® (gefitinib), Tarceva® (erlotinib) and icontinib.

Embodiments of the present disclosure include methods of treating cancer in a subject including the following steps. First, a sample is taken from a subject having a cancer predicted to be sensitive to anti-EGFR treatment before or at the initiation of a treatment regimen with an anti-EGFR therapy/drug. A pre-treatment level of peroxiredoxin 6 (PRDX6) protein is determined from this sample. The methods further include initiating treatment regimen for the subject with an anti-epidermal growth factor receptor (EGFR) drug. Initiation of the treatment regimen includes providing and/or administering one or more doses of the anti-EGFR drug to the subject over a period of time. In embodiments, the anti-EGFR drug includes one or more of Iressa® (gefitinib), Tarceva® (erlotinib), and Conmana® (icontinib). The initial treatment regimen dosing and timing can be determined by the subject's doctor/oncologist based on standard criteria (e.g., staging, body weight/size/age, treatment history, tumor size and number, and the like).

Then, a second level of PRDX6 is determined from a second sample taken from the subject. In embodiments, the second level of PRDX6 is determined from a second sample taken no later than about 4 weeks after the initial treatment with the anti-EGFR drug. In embodiments the second level is determined from a sample taken no later than about 2 weeks, or between about 2 weeks and about 4 weeks of initiation of the anti-EGFR therapy. In embodiments, a PRDX6 expression profile is created for the subject after the second level of PRDX6. The PRDX6 expression profile compares the pre-treatment and second PRDX6 levels. In embodiments with respect to one or more aspects of the anti-EGFR treatment regimen (e.g., time from initiation of treatment, dosage, etc.). The PRDX6 expression profile may also compare the PRDX6 levels with respect to other variables, such as tumor size, disease progression, symptoms, and the like. Embodiments of the methods include determining one or more subsequent levels of PRDX6 in samples taken from the subject at regular intervals of time after the second sample and updating and/or re-creating the PRDX6 expression profile comparing the pre-treatment, second, and subsequent PRDX6 levels. As noted, the PRDX6 expression profile can include the PRDX6 levels determined from the various samples, and, in embodiments, can correlate the PRDX6 levels with drug dosages, tumor load, and the like.

Then, the methods include determining and/or analyzing the efficacy of the anti-EGRF drug in reducing tumor volume using the PRDX6 expression profile. Then, the method includes continuing, modifying or discontinuing the treatment regimen with the anti-EGFR drug based on the PRDX expression profile. In embodiments, the dosage of the anti-EGFR drug can be modified/adjusted based on the PDX6 expression profile to increase efficacy of the anti-EGFR drug. In embodiments, the treatment regimen is modified by adjusting the dosage of the anti-EGFR drug up or down (or changing the timing/frequency) of dosage based on the analysis of the PRDX6 expression profile. For instance, the dosage may be increased if the PRDX6 profile indicates moderate sensitivity of the cancer to the treatment or if the result is inconclusive. In embodiments, the dosage may be maintained when the profile indicates standard or high sensitivity of the cancer to the treatment, and in others the treatment may be discontinued if the profile indicates resistance or acquired resistance to the drug.

The present disclosure also includes methods of treatment for cancer including determining a pre-treatment level of PRDX6 as described above protein in a sample taken from a subject having cancer predicted to be sensitive to anti-EGFR treatment and initiating a treatment regimen for the subject with at least one anti-EGFR drug where one or more doses of the anti-EGFR drug is administered to the subject over a period of time. Then, a second level of PRDX6 is determined in a sample taken from the subject no later than about 4 weeks after the initial treatment with the anti-EGFR drug. In embodiments the second level is determined from a sample taken about 2 weeks after or between 2 and 4 weeks after initiation of treatment. In embodiments of the methods of treating cancer, treatment with the anti-EGFR drug is continued when the second level of is sufficiently greater than the pre-treatment level of PRDX6 for the subject, indicating response of the cancer cells to the anti-EGFR drug (e.g., sensitivity). In the examples below, the PRDX6 expression profile in response to anti-EGFR treatment indicates that initial treatment results in an increase in PRDX6 levels due to induction of PRDX6 expression or secretion by the cancer cells by the drug treatment. Thus an increase in PRDX6 levels at the second sample time (e.g., about 2-4 weeks after initiation of drug treatment) indicates that the cancer is sensitive to the drug. In embodiments when the second PRDX6 level is about 10% greater, or more than 10% greater, than the pre-treatment level of PRDX6 for the subject it indicates sensitivity and treatment is continued. In some embodiments, a second level of about 20%, or more, greater than the pre-treatment level indicates that treatment is working and should be continued. Second levels above about 10% and above about 20% of the first level also indicate sensitivity. In embodiments of the methods of treating cancer of the present disclosure, continuing to treat the subject with the anti-EGFR drug includes maintaining the dosage of the anti-EGFR drug or adjusting the dosage of the anti-EGFR drug. In embodiments, a patient's individual PRDX6 expression profile may indicate a variance from the average response, and a PRDX6 level lower than about 10% greater than the pre-treatment level may indicate sensitivity. In such case, the clinician would make a determination based on experience with the patient, general experience, and analysis of the patient's PRDX6 expression profile.

When the second level of PRDX6 in the subject, taken as described above, is about the same as the pre-treatment (e.g., background) level, is less than the pre-treatment level, or is less than about 10% greater than the pre-treatment level of PRDX6, this may indicate that the tumor is not responding to the anti-EGFR drug, either due to insufficient dosage, resistance, or other factor. If insufficient dosage is suspected, dosage can be increased. Thus, in some embodiments, the method further includes increasing the amount of the drug subsequently administered to the subject when the second PRDX6 level is about the same as the pre-treatment level, less than the pre-treatment level, or less than about 10% greater than the pre-treatment level of PRDX6 for the subject.

If resistance is suspected other tests can be done to confirm resistance, or treatment can continue (at the same or increased dosages) and additional PRDX6 levels can be taken in a "wait and see" approach. If subsequent levels remain similar to pre-treatment levels and second levels, this may indicate resistance and treatment can be discontinued. Thus, in embodiments, when subsequent levels remain within about 10% of each other, this may indicated resistance and treatment can be discontinued or adjusted or further testing can be conducted.

In embodiments, the methods of treating cancer or modifying a cancer treatment in a subject further include determining a third level (and optional subsequent levels) of PRDX6 in a third sample taken from the subject after the second sample. In embodiments, the third level is determined from a sample taken from the subject about 6 weeks, or more, after an initial treatment with the anti-EGFR drug. In embodiments, the third level is determined from a sample taken from the subject within about 2 weeks from the sample used to determine the second level. The third level is then compared with the pre-treatment and second PRDX 6 levels. In embodiments, the method includes creating an updated or new PRDX6 expression profile after the third level (and/or any subsequent levels) is determined.

In the examples below, the PRDX 6 profiles obtained from cell culture, murine cancer models and human clinical data, indicate that for sensitive cancers, after an initial increase in PRDX 6 levels at a second sample time, the levels thereafter decrease as a function of a reduction in tumor size due to a fewer number of cancer cells to produce the PRDX 6. This profile demonstrates that a decrease in PRDX 6 levels at a third sample time, for instance, at about 6 weeks after an initial treatment, or at about 2 weeks, about 2-4 weeks, or more after the second sample, indicates sensitivity of the cancer to the anti-EGFR drug. Thus, in embodiments, the methods include continuing to treat the subject with the anti-EGFR drug when the third level of PRDX6 is the same or less than the second level of PRDX6 for the subject, since this would indicate that the drug is working to decrease tumor size and thus decrease PRDX6 expression by tumor cells. If the third level does not show a decrease from the second level, this may mean that the tumor is not responding to treatment, that the dosage should be increased, or that more time is needed for response. If the third level is greater than the second level it may mean that the cancer is resistant and additional PRDX6 levels may be taken at intervals of time after the third sample to continue to build the PRDX6 expression profile and evaluate the efficacy of the anti-EGFR treatment and confirm resistance or demonstrate sensitivity.

Thus, in embodiments, the methods of the present disclosure further include determining one or more subsequent levels of PRDX6 in a sample taken from the subject at regular intervals of time after the third sample and comparing each subsequent level of PRDX6 to the third PRDX6 level and to any other PRDX6 level taken between the third level and itself. Such methods also include determining possible resistance of the cancer to the anti-EGFR drug when at least two consecutive PRDX6 levels beyond the second level are within about 10% of each other or less, indicating non-responsiveness of the tumor and possible resistance. Also, if a third level of PRDX6 was lower than the second level, and one or more subsequent levels after the third are greater than the third level (e.g., more than about 10% greater than the third level), this can indicate tumor re-growth and possible acquired resistance to the anti-EGFR drug. When resistance is suspected and/or determined according to the methods of the present disclosure, the treatment regimen for the subject can be adjusted to improve efficacy of the treatment. In embodiments, adjusting the treatment regimen may include increasing or decreasing the dosage of the anti-EGFR drug, discontinuing the drug, replacing the anti-EGFR drug with another drug (e.g., a different anti-EGFR drug or a different cancer drug), or temporarily halting treatment in the hope of re-sensitizing the cancer to the drug.

The present disclosure also includes methods of determining sensitivity or resistance of a cancer in a subject to an anti-EGFR drug. Embodiments of such methods include determining a pre-treatment level of PRDX6 protein in a sample taken from a subject having cancer; administering one or more doses of an anti-epidermal growth factor receptor (EGFR) drug to the subject over a period of time; determining a second level of PRDX6 in a sample taken from the subject no later than about 4 weeks after an initial treatment with the anti-EGFR drug (or between about 2 weeks and about 4 weeks after initial treatment); and comparing the pre-treatment level of PRDX6 with the second level of PRDX6. In some embodiments, the first and second levels are used to create a PRDX6 expression profile for the subject. Embodiments of the methods further include determining sensitivity of the cancer to the anti-EGFR drug and continuing to treat the subject with the anti-EGFR drug when the second level of is about 10%, or more, greater than the pre-treatment level of PRDX6 for the subject. In embodiments, when the second level is between about 10% and about 20% greater or about 20%, or more, greater than the pre-treatment level of PRDX6 for the subject, this indicates sensitivity of the cancer. Embodiments also include determining potential non-responsiveness or resistance of the cancer to the anti-EGFR drug and optionally discontinuing treatment with the anti-EGFR drug when the second level is about the same as the pre-treatment level, about 10% less than the pre-treatment level, or less than 10% greater than the pre-treatment level of PRDX6 for the subject. As discussed above, if non-responsiveness or resistance is suspected, additional PRDX6 levels can be taken to confirm non-responsiveness ore resistance (e.g., by consecutive levels with little change or showing re-growth of tumors, e.g., within 10% of each other or growth after a third level is taken).

The methods of the present disclosure further include detecting acquired resistance to anti-EGRF therapy including determining one or more subsequent levels of PRDX6 in samples taken from the subject, where the one or more samples are taken beginning after samples used to determine the second or third level (in embodiments, at least about 6 weeks (between about 6 and about 8 weeks, about 6 weeks, or more) after an initial treatment with the anti-EGFR drug), and maintaining or increasing the amount of the anti-EGFR drug subsequently administered to the subject when the one or more subsequent levels of PRDX6 are about 10%, or more, less than the second level of PRDX6 for the subject. In embodiments, these methods further include determining potential acquired resistance to anti-EGRF therapy when the third level is the same or greater than the second level of PRDX6 for the subject, indicating a tumor that is not shrinking or that is continuing to grow or exhibiting re-growth.

In the above methods of the present disclosure the cancer is selected from a group of cancers sensitive to anti-EGFR therapy. In embodiments the anti-EGFR sensitive cancers can include, but are not limited to, small cell lung cancer (NSCLC), colorectal cancers, pancreatic cancer, prostate cancer, and breast cancer. Representative anti-EGFR drugs for use in the methods of the present disclosure include, but are not limited to, gefitinib, erlotinib, and icontinib.

In the methods of the present disclosure, determining a level of PRDX6 in a sample taken from the subject can include performing an ELISA assay on the sample with a capture antibody specific for PRDX6 and a detection antibody capable of binding PRDX6. In embodiments, the capture antibody is sc-59671 and the detection antibody is ab73350, since this combination provided enhanced detection as described in Example 2 below. Embodiments of the present disclosure also include assays and systems for use in the methods of the present disclosure.

In other embodiments, the methods of the present disclosure also include methods of determining sensitivity or resistance of a cancer to an anti-epidermal growth factor receptor (EGFR) drug using a sample from a patient to test drug activity or resistance in vitro before or simultaneously with administering the drug to the subject. In embodiments, such methods include obtaining a biopsy sample of cancer cells from a subject, growing the cancer cells in culture, determining a level of peroxiredoxin 6 (PRDX6) protein produced by the cells, exposing the cancer cells to the anti-EGFR drug, determining a second level of PRDX6 protein produced by the cells between about 10 and about 24 hours after exposing the cells to the anti-EGFR drug, and comparing the first level of PRDX6 to the second level of PRDX6. In embodiments, the methods include creating a PRDX6 expression profile for the subject cell culture. In embodiments, the PRDX6 expression profile for the cell cultures compares the first and second level of PRDX6 and, in some embodiments, also includes any subsequent level. The methods further include determining sensitivity of the cancer to the anti-EGFR drug when the PRDX6 profile indicates responsiveness of the cells to the anti-EGFR drug. For instance, in embodiments, when second level of PRDX6 is about 20%, or more, greater than the first level of PRDX6, this indicates sensitivity. In embodiments, a second level of PRDX6 about 10%, or more, greater than the first level indicates sensitivity. Embodiments of the methods also include determining resistance of the cancer to the anti-EGFR drug and recommending against treatment with the anti-EGFR drug when the PRDX6 profile indicates resistance. For instance, in embodiments, when second level is about the same as the first level, or within about 10% greater or lesser than the first level of PRDX6 it indicates resistance. In embodiments, a second level of PRDX6 between about 10% and 20% greater than the first level of PRDX6 indicates an inconclusive result. When an inconclusive result is obtained, further testing (e.g., continuing to expose the cell culture to the anti-EGFR drug and to determine subsequent PRDX6 levels, or other testing) can be conducted to indicate sensitivity or resistance. In embodiments, the methods can further include recommending treatment of the subject with the drug when the cancer is determined to be sensitive to the anti-EGFR drug, recommending against treatment of the subject with the drug when the cancer is determined to be resistant to the anti-EGFR drug, and/or recommending treatment of the subject with the drug and/or further testing when the result is inconclusive.

Embodiments of the present disclosure also include assays and systems for performing the methods described above. Embodiments of such assays and systems are described in the examples below. Briefly, in embodiments, a cancer sensitivity assay of the present disclosure includes a capture antibody specific for PRDX6 protein and a detection antibody capable of binding PRDX6 and producing a detectable signal. In embodiments, such an assay includes an ELISA sandwich assay specific for PRDX6. In some embodiments, a sample from a subject (e.g., a subject having a cancer predicted to be sensitive to an anti-EGFR treatment) can be tested in the assay, and the assay can include the sample obtained from the subject as well as the capture and detection antibodies capable of binding PRDX6. The sample can be obtained from the subject before initiation of a treatment regimen with an anti-EGFR drug, during the treatment regimen, or even after the treatment regimen has been completed. In embodiments where sample cells will be tested with anti-EGFR drug in vitro, the assay further includes culture medium for growing a sample of cancer cells obtained from a patient and an anti-EGFR drug to be tested with respect to the sample cells. In embodiments, the capture antibody is sc-59671 and the detection antibody is ab73350. In embodiments, the anti-EGFR drugs is selected from gefitinib, erlotinib, and icontinib. In embodiments, the sample cells are from a cancer selected from NSCLC, colorectal cancer, pancreatic cancer, prostate cancer, and breast cancer.

In embodiments, a system for assessing sensitivity of a cancer to an anti-EGFR drug according to the methods of the present disclosure includes an assay as described above for determining an amount of PRDX6 protein present in a sample from a subject or a cell culture, and instructions for producing a PRDX6 expression profile for a subject or cell culture. In embodiments, the assay for the system includes at least a capture antibody specific for PRDX6 protein and a detection antibody capable of binding PRDX6 and producing a detectable signal. In embodiments, the instructions for producing a PRDX6 expression profile include instructions for preparing a PRDX6 expression profile that compares two or more PRDX6 levels obtained from assay results of two or more samples from the subject or cell culture. As discussed above, for the samples used to obtain the PRDX6 expression levels for the profile, the first sample is obtained from the sample prior to treatment of the subject or exposure of the cell culture to the anti-EGFR drug, and the second (and any subsequent sample) is obtained at a time after initiation of treatment or exposure. Embodiments of the system of the present disclosure also include instructions for using the PRDX6 expression profile to assess the sensitivity of the cancer to the ant-EGFR drug using the methods discussed above. Thus, in embodiments, the instructions for using the PRDX6 expression profile suggest determining sensitivity of the cancer to the anti-EGFR drug when the expression profile shows a second level of PRDX6 about 20%, or more, greater than a first level of PRDX6, determining resistance of the cancer to the anti-EGFR drug when the expression profile shows a second level about the same as the first level or within about 10%, greater or lesser, than the first level of PRDX6, and determining an inconclusive result when the second level of PRDX 6 is between about 10% and about 20% greater than the first level of PRDX6. In embodiments, the instructions for producing the PRDX6 expression profile further include instructions for updating the PRDX6 expression profile based on the PRDX6 levels of one or more subsequent samples taken after the second sample, and where the instructions for using the PRDX6 expression profile further include instructions for maintaining or increasing the amount of the anti-EGFR drug subsequently administered when the one or more subsequent levels of PRDX6 are about 10%, or more, less than the second level of PRDX6, and determining potential acquired resistance to anti-EGRF therapy when a subsequent level is the same or greater than the second or immediately preceding level of PRDX6 for the subject. The instructions and elements of the system can include any compositions, vessels, apparatuses, and directions useful for carrying out the methods of the present disclosure discussed above and described in the examples.

As additional biomarkers are tested and their expression profiles in response to anti-EGFR drugs are analyzed and characterized, additional methods according to the present disclosure will include using a panel of anti-EGFR biomarkers to make more detailed assessments of anti-EGFR therapy response in subjects and to tailor treatments to a profile of the panel of biomarkers. Embodiments of such methods include determining a pre-treatment level of a panel of anti-EGFR biomarkers in a sample taken from a subject having a cancer believed to be sensitive to anti-EGFR treatment, wherein the panel of biomarkers includes two or more compounds differentially regulated by one or more anti-EGFR drugs. The methods further include initiating a treatment regimen for the subject with at least one anti-EGFR drug including administering one or more doses of the anti-EGFR drug to the subject over a period of time. The methods further include determining a second level of each biomarker in a second sample taken from the subject no later than 4 weeks after the initial treatment with the anti-EGFR drug and determining one or more subsequent levels of each biomarker in samples taken from the subject at regular intervals of time after the second sample. The pre-treatment, second, and subsequent levels for each biomarker are compared and/or analyzed and used to create an anti-EGFR biomarker expression profile for the subject. In embodiments, the biomarker expression profile can be used determine efficacy of the anti-EGRF therapy. In embodiments, the dosage of the anti-EGFR drug is based on the biomarker expression profile.

In embodiments of such methods, the panel of anti-EGFR biomarkers includes one or more compounds selected from the group including, but not limited to, peroxiredoxin 6 (PRDX6), beta-2-microglobulin (B2M), Epithelial cell adhesion molecule (EpCAM), MNNG HOS Transforming gene (c-MET), Thioredoxin (TXN), Tumor-associated calcium signal transducer 2 (TROP2), Testican-2 (SPOCK2), Coagulation Factor III (F3), Macrophage migration inhibitory factor (MIF), Claudin 1 (CLDN1), Annexin A2 (ANXA2), Prosaposin (PSAP), family with sequence similarity 3 (FAM3C), aldo-keto reductase family 1, member B1 (AKR1B1), cathepsin D (CTSD), lectin galactoside-binding soluble 3 (LGALS3), calumenin (CALU), heat shock 60 KDa protein 1 (HSPD1), hepatoma-derived growth factor (HDGF), mesencephalic astrocyte-derived neurotrophic factor (MANF/ARM ET), calreticulin (CALR), Activated Leukocyte Cell Adhesion Molecule/Center of Differentiation 166 (ALCAM/CD166), and tumor protein translationally-controlled 1 (TPT1).

Additional details about some embodiments of the methods of the present disclosure are described in the examples below.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Quantitative Proteomic Profiling Identifies Potential Biomarkers to EGFR Kinase Inhibition The present example demonstrates that proteomic discovery in in vitro tissue culture models can identify proteins with concordant in vivo behavior and further, can be a valuable approach for identifying tumor-derived serum proteins. In this Example Stable Isotope Labeling of Amino acids in Culture (SI LAC) is used with proteomic technologies to quantitatively analyze the gefitinib-related protein changes in a model system for sensitivity to EGFR targeted tyrosine kinase inhibitors. The change in expression profile was validated in vitro, and the panel of response markers was screened in an in vivo isogenic resistant model to demonstrate that these were markers of gefitinib response and not simply markers of phospho-EGFR downregulation. This work also demonstrated the ability to identify which proteins might be useful as markers for monitoring response and which proteins might be useful as markers for a priori prediction of response.

The epidermal growth factor receptor (EGFR) signaling pathway, which has been implicated in a range of cancers, including breast, lung, and colon carcinomas (1, 2), has been a particular focus of pathway-targeted therapeutics(3). The multilayered EGFR pathway, including ligands, receptors, and signaling molecules, impacts fundamental cellular processes such as differentiation, growth, motility, and division of epithelial cells (4, 5). Significant effort has been made to identify the constituents of the EGFR pathway, and demarcate the relationships among those constituents, their post-translational modifications (6), and more broadly to elucidate mechanisms for how the pathway interacts with diverse effector molecules which lead to changes in cellular behavior (7).

In addition to increasing understanding of the EGFR axis, clinical utility can be obtained by identifying novel pathway members whose abundance is indicative of pathway dependence and activation status. Lung cancer patients with activating mutations in EGFR demonstrate sensitivity to EGFR targeted tyrosine kinase inhibitors (TKI) (8, 9), such as gefitinib (ZD1839, Iressa®, AstraZeneca) and erlotinib (OSI-774, Tarceva®, Genentech) (10, 11). These compounds inhibit the downstream activity of the EGFR axis by competitively inhibiting ATP binding in the catalytic core of the kinase domain of EGFR. Though effective in some patients, many initially demonstrating clinical response to EGFR targeted TKI's ultimately develop resistance(12). Diverse transcriptomic and phosphoproteomic studies, have also been undertaken to explore the impact of EGFR TKI inhibition on sensitive and resistant cells (6, 13-15). These approaches have enhanced the understanding of EGFR biology and uncovered diverse mechanisms of resistance (16-19). Despite these studies, there is still an unmet biologic and clinical need for proteins predictive of response or indicative of therapy effectiveness to EGFR TKI's.

To bridge this gap, in the present example assessed the broad protein network effects of inhibiting EGFR kinase with gefitinib in an epidermoid cancer cell line (A431) that overexpresses EGFR. This cell line is a model system for sensitivity to EGFR targeted therapies (e.g., gefitinib) (20-22) and has been studied. To quantify the gefitinib induced changes in protein abundance, Stable Isotope Labeling of Amino Acids in Culture (SILAC) with mass spectrometry (MS) was employed. Following initial broadscale profiling, a panel of proteins was selected for more extensive follow-up analysis including interrogation with various EGFR-axis specific and non-specific therapeutic agents. In order to assess the portability of these protein markers beyond A431 tissue, the dose-dependent protein level change of the panel, and its generality both in vivo and to non small-cell lung cancer (NSCLC) tissue, was subsequently assessed. These experiments suggested that the results are not restricted to in vitro studies of the A431 cell line, and have utility for biologic and clinical studies of EGFR TKI inhibition.

Materials and Methods

Reagents and Cell Lines:

All chemicals were purchased from Sigma (St. Louis, Mo.) unless stated otherwise. Antibodies directed to ELAVL-1, GLTSCR2, KLF5, and QARS, were purchased from Abnova (Taipei City, Taiwan). Antibodies directed to HSPG2, BAG4, S100A9, SERPINE1, TNFAIP2, Lipocalin-2, and VAMP3 were purchased from Novus Biologicals (Littleton, Colo.). Antibody directed to Claudin-1 was purchased from Zymed/Invitrogen (Carlsbad, Calif.). Antibodies directed to ALB, Apo-L, C3, CBFB, EpCAM, PRDX6, and Transferrin were purchased from Abcam (Cambridge, Mass.). Antibodies directed to Testican 2 (SPOCK2), and TROP-2 were purchased from R&D Systems (Minneapolis, Minn.). Antibodies directed to EGFR, p-EGFR (Y-1068), and SNX5 were purchased from Santa Cruz Biotechnology (Santa Cruz, Calif.). The antibody directed to PDCD4 was purchased from Rockland Immunochemicals (Gilbertsville, Pa.). The antibody directed to actin was purchased from Sigma. A431, HCC827, H1650, H23, and H1975 cells lines were obtained from the standardized tissue bank, ATCC (Manassas, Va.), which authenticates tissues by genotype and used within six months. Cells were verified to be free of mycoplasma (USC core facility). The MTS assay for cell viability at 48 hours was conducted as directed by the manufacturer (Promega, Madison, Wis.).

Culture, Isotopic Labeling, and Treatment of Cells with Therapeutic Agents:

The A431 human epithelial carcinoma cells were grown in DMEM media (Invitrogen) containing 1% of dialyzed fetal bovine serum (FBS, Invitrogen) with $^{13}$C-lysine (Invitrogen) substituted for lysine for seven passages (1:2) according the previously published SILAC protocol (23). A concentration of one percent serum was used (instead of the more typical 10% or higher) for the shed protein studies because it increases the ability to reliably quantify cell-derived signals amongst the background bovine serum proteins by an order of magnitude compared to 10% serum without compromising phenotype. Specifically, 1% serum does not compromise cell growth, viability, or response to therapy. To confirm this cell viability assays were performed on A431 cells, and differences in cell growth rate or gefitinib $IC_{50}$ were not observed upon dosing between 1-10% serum. Cells remained attached to plates and there was no evidence of rounding-up. Incorporation of $^{13}$C Lys isotope exceeded 97% of the total protein lysine content. Samples from the same batch of cells were used for analysis of cell surface proteins and for analysis of conditioned media and whole cell lysate proteins. Cells were maintained in SI LAC media and grown in the presence of 100 nM of gefitinib (Protein Kinases, Inc., Germany) for 2 or 16 h. The shed proteins were obtained directly from the cell conditioned media after 16 h of treatment. Cells and debris were removed by centrifugation at 5,000×g and filtration through a 0.22-μm filter. Total extracts were obtained by sonication of ~2×10$^7$ cells in 1 ml of PBS containing the detergent octyl-glucoside (OG, 1% w/v) and protease inhibitors (complete protease inhibitor cocktail, Roche Diagnostics, Penzberg, Germany) followed by centrifugation at 20,000×g.

Protein Identification by LC-MS/MS:

Protein digestion and identification by LC-MS/MS was performed as described previously (24). Briefly, each one of the reversed-phase fractions were individually digested in solution with trypsin (400 ng/fraction) and grouped into 15 to 21 pools for each cell line and each compartment (i.e., cell surface, conditioned media, and soluble whole cell lysate) based on chromatographic features. Pools were individually analyzed by LC-MS/MS in a LTQ-FTICR or LTQ-ORBITRAP mass spectrometer (Thermo-Finnigan, Waltham, Mass.) coupled to a nanoflow chromatography system (Eksigent, Dublin, Calif.) using a 25-cm column (Picofrit 75 μm ID, New Objectives, Woburn, Mass.) packed in-house with MagicCl8 resin (Michrome Bioresources, Auburn, Calif.) over a 90 minute linear gradient. Acquired data was automatically processed using default parameters, except where noted, by the Computational Proteomics Analysis System V8.2—CPAS (25). The tandem mass spectra were searched against version 3.13 of the human IPI database (60,428 protein entries) with five sequences for human and bovine trypsin added. The search was performed with XITandem (2005, Dec. 1). The mass tolerance for precursor ions was set during the search to 1 AMU with a mass tolerance for fragment ions set to 0.5 Daltons. However, matches with less than 5 ppm mass accuracy were considered to false positives and discarded. A fixed modification of 6.020129 mass units was added to lysine residues for database searching to account for incorporation of the heavy lysine isotope. All identifications with a PeptideProphet (26) probability greater than 0.9 were submitted to Protein Prophet (27), and the subsequent protein identifications were filtered at a 1% error rate with tryptic fragments (1 missed cleavage) with allowance for fixed modification on C=57.021 and variable modifications on C=−17.027, E=−18.011, K=6.020, M=15.995, and Q=−17.027. Detailed proteomic methods in supplemental text.

In Vivo Xenografts:

The A431 resistant model was derived in vivo from tumors with demonstrated resistance upon gefitinib dosing over a 9 month period by serial passage of A431 subcutaneous xenografts in presence of 50 mg/kg of gefitinib (AstraZeneca, London, UK) for nine months. Eight to 10 week-old nude athymic BALB/c female mice were obtained from Charles River Breeding Laboratories (Wilmington, Mass.) and were maintained in pressurized ventilated cages at the Cedars-Sinai Medical Center vivarium. All animal experiments were performed as per the institutional guidelines and were approved by the Institutional Animal Care and Use Committee at CSMC. Gefitinib was administered orally daily to twenty animals. Control animals received vehicle alone (20 animals). The tumor volumes were measured twice a week with a digital vernier caliper and were calculated as: Tr/6×(larger diameter)×(smaller diameter)$^2$. The data are represented as a plot of mean tumor volumes versus time measured in days from 5 animals.

Verification:

In vitro and in vivo verification of proteomics data was accomplished by western blot. For in vitro experiments, cells were incubated in heavy SI LAC media (1% FBS) for 16 h with 0, 100, 500, and 1,000 nM gefitinib, erlotinib (LC Labs, Woburn, Mass.), AKT inhibitor (A6730, Sigma), or MAPK inhibitor (PD98059, Calbiochem) or 5, 25, 100 nM taxol (LC Labs). The cells were washed three times with PBS and lysed in RAF buffer (50 mM Tris-HCl, pH 7.4; 1% NP-40; 0.25% sodium deoxycholate; 150 mM NaCl; 1 mM EDTA; 1 mM PMSF; 1 mg/ml each aprotinin, leupeptin, pepstatin; 1 mM Na$_3$VO$_4$, 1 mM NaF) supplemented with 1% SDS. Lysates were sonicated for 10 minutes, heated at 95° C. for 10 minutes, and centrifuged for 15 minutes at 20,000×g. The supernatant was cleared through a 0.22-micron filter and protein concentration was determined (BCA, BioRad, Hercules, Calif.). Lysates were subject to SDS-PAGE and subsequent immunoblot. For in vivo experiments, mouse tumor pieces from 5 mice were pooled and suspended in RAF buffer and homogenized with a high-speed blender. The homogenate was centrifuged for 5 min at 200×g. The supernatant was sonicated on ice for 2 minutes and centrifuged for 1 hr at 12,000×g. The supernatant (soluble fraction) was cleared through a 0.22-micron filter and processed as above. The pellet (insoluble fraction) was resuspended in RAF buffer with 2% SDS and DTT, heated at 95° C. and sonicated prior to processing. Serum from 5 mice was pooled and depleted using two MARS-3 columns (Agilent) connected in tandem with HPLC. The unbound fraction was concentrated to a final concentration of 2 mg/ml and processed as above. Proteomics Data has been deposited at http://proteomics.fhcrc.org/CPL/home.html and is accessible to the public.

Results

Deep Quantitative Proteomics of Three Sub-Proteomes of A431 Cells

In order to quantitatively enumerate the changes associated with the inhibition of EGFR activity, untreated A431 cells were compared with A431 cells treated with 100 nM gefitinib for either 2 or 16 hours prior to multi-compartment proteomic analysis. Three separate proteome fractionation techniques were used to interrogate cellular changes: a) shotgun LC/MS/MS to assess the intracellular proteome [referred to as the "whole cell lysate"]; b) biotin-capture-based cell-surface profiling; and c) Solid-Phase Extraction of Glycoprotein (SPEG) profiling (28) for the enrichment and subsequent study of shed proteins. Using three separate techniques enabled a diversity of analysis; characterization of intracellular proteins facilitates understanding drug mechanism, whereas the cell-surface and shed proteins are potentially relevant to molecular diagnostics, tumor imaging, and targeted therapies. Analysis was performed in a reciprocal fashion (e.g., one experiment involved treatment of isotopically 'heavy' cells, and in a second experiment isotopically 'light' cells were treated). The dose of 100 nM gefitinib inhibits EGFR phosphorylation ($IC_{50}$ 40-80 nM) while minimizing suppression of other kinases (for example, the $IC_{50}$ for HER2 is 1,200-3,700 nM) (29).

Figure 1B:
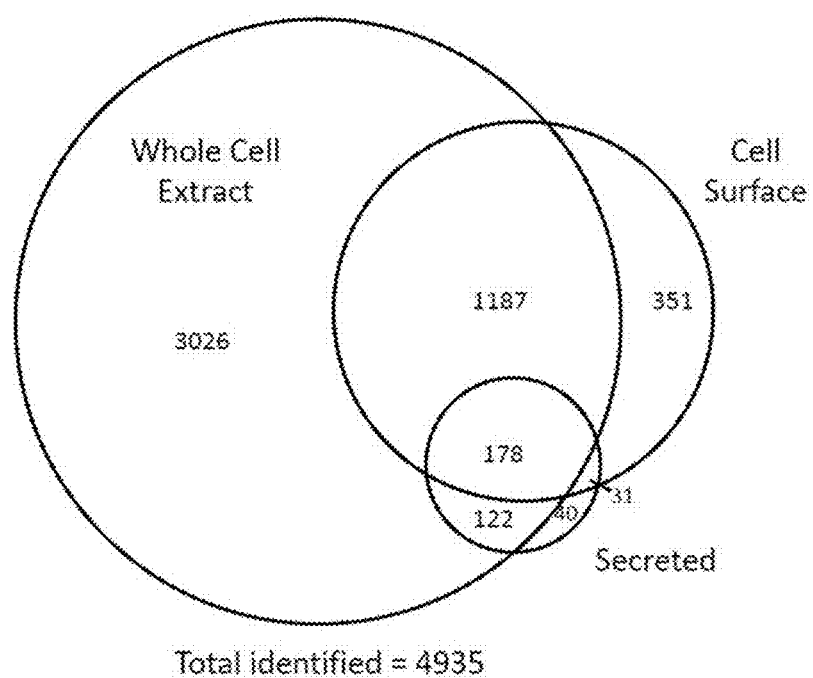
Figure 1C:
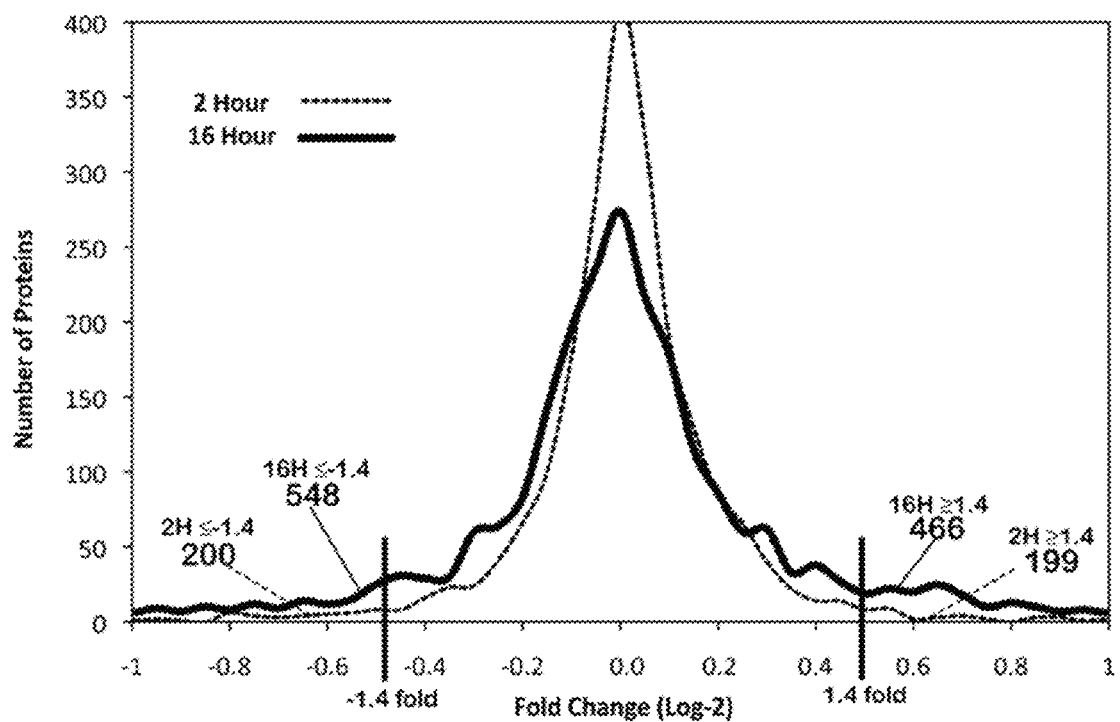

As a reference for non-TKI induced proteome changes, untreated A431(L) were admixed with untreated A431(H), and a standard deviation of 0.25 was observed in the H/L fold change (data not shown). This enabled establishment of a threshold for significant quantitative fold change (1.4). A total of 4,935 unique proteins (total peptides=329,435; unique peptides=82,269) were identified with notable overlap between sub-proteomes (FIG. 1B). The distribution of proteins with a fold change of ±1.4 was significantly higher in the 16-hour experiment, so this time point was used for subsequent analyses (FIG. 10).

Verification of Proteins Indicative of Response to Gefitinib Treatment

Figures 2A, 2B:
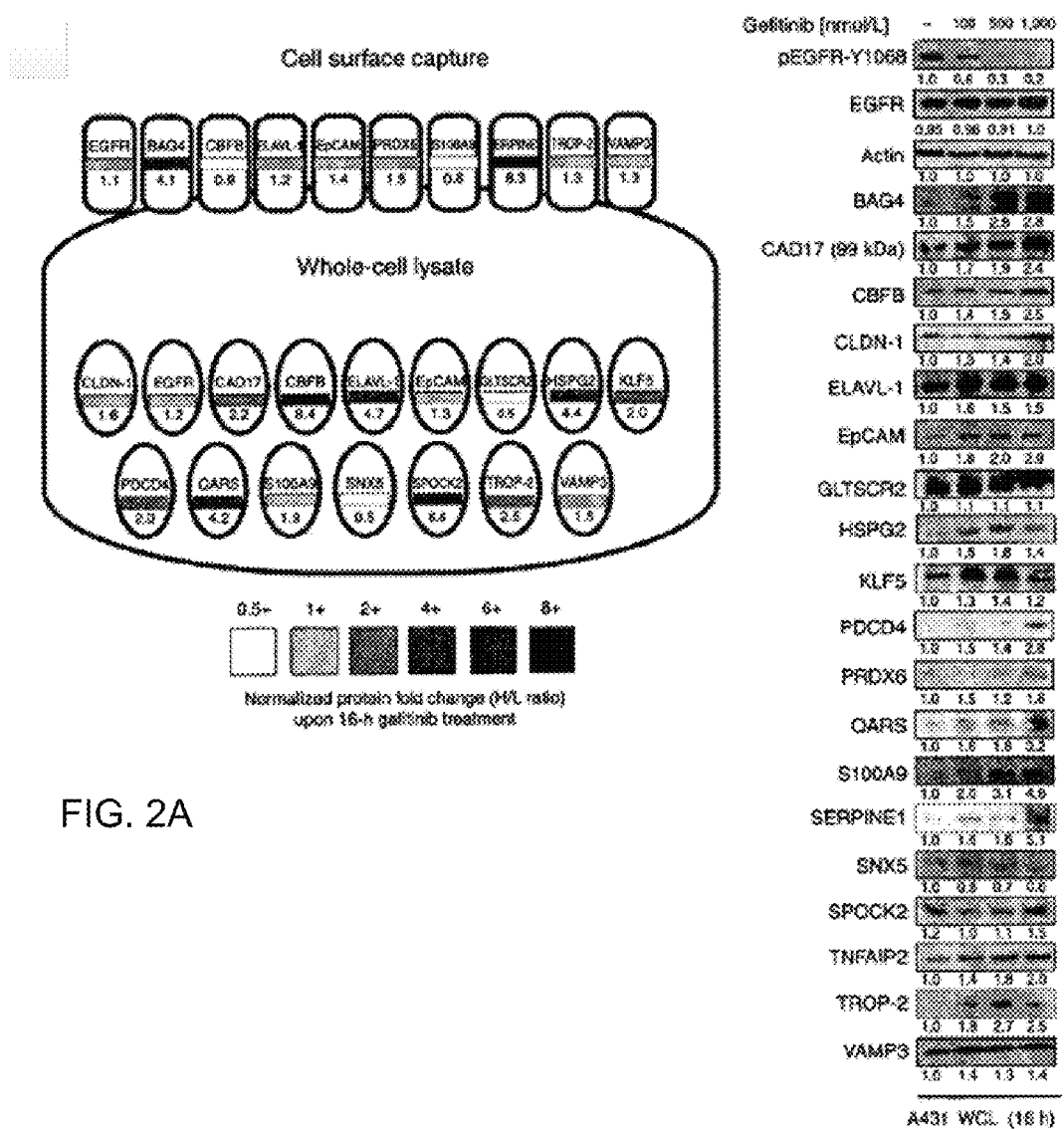
FIGS. 2A-2B illustrate in vitro verification of SILAC ratios.

Of the 180 proteins with greater than 1.4 fold changes in abundance upon gefitinib-treatment (data not shown), 19 were initially selected for immunoassay-based verification based on magnitude of change in abundance, availability of commercially available affinity reagents of sufficient quality, and confidence that the proteins were correctly identified and quantified (criteria are described in the Methods section). Protein selection was unbiased with regard to biological function. Focus was placed on proteins whose abundance was up-regulated in response to treatment, as these are likely to be useful markers of response. Immunoblots were performed on treated and untreated A431 lysates and verification of the treatment-response was possible for 19 proteins. Densitometry was used to determine the quantitative fold change in protein concentration from three independent experiments (FIG. 2). Dose-titration is a common technique to verify the dose-dependent impact of a perturbation. It is recognized, that higher concentrations of gefitinib may lead to off-target effects; however, it is most likely that such off-target effects would mute the dose-dependent effect rather than producing or amplifying it. The response of ELAVL-1 to gefitinib treatment at 100 nM was not amplified at higher doses (500 and 1,000 nM), but all other proteins had a dose-dependent increase when extracts of cells treated (after 16 hrs) with 100, 500, and 1,000 nM gefitinib as determined by western blot. VAMP3, KLF5, and GLTSCR2 demonstrated a marginal increase upon gefitinib dosing at 100 nM and, as a result, were excluded from further study. Overall, 16/19 (84%) immune-blot studies supported the proteomic predictions. This percentage may increase as new commercially available antibodies become available and as more sophisticated analytic techniques are employed.

Pathway Analysis of Protein Panel Demonstrates Specificity to EGFR Pathway

To ascertain if the protein level changes associated with gefitinib dosing were a result of downregulation of EGFR tyrosine phosphorylation, the enrichment of known phosphoproteins was examined amongst the 180 upregulated proteins. 56% of these proteins were previously characterized as phosphoproteins. This suggests that the proteomic experiment successfully impacted proteins associated with phosphorylation events. Use of gene-set enrichment identified protein networks associated with the perturbed proteins resulting from gefitinib treatment and allowed observation network changes associated with non-canonical EGFR networks. As the 16 verified proteins were not members of any obvious, known bio-module (though most were within 1-hop of canonical EGFR pathway members), confirmation was sought that the impact of treatment on the proteins in the selected panel was specific to EGFR inhibition. A431 cells were treated with either erlotinib (100-1,000 nM) or with the off-axis control chemotherapeutic paclitaxel (10-100 nM), and the changes in levels of the 16 validated proteins and controls were investigated using immunoblots (Table I). Treatment with erlotinib produced protein abundance changes that mirrored the effect of gefitinib, whereas none of the proteins tested demonstrated a change in abundance in response to paclitaxel treatment. Since the $IC_{50}$ of paclitaxel in A431 cells was previously shown to be ~10 nM (30), the lack of protein abundance changes with paclitaxel treatment at concentrations above the drug's $IC_{50}$ suggests that the proteins in the selected panel are not impacted by off-axis chemotherapeutics. The responses of the proteins in the panel to gefitinib and erlotinib and the lack of responses to paclitaxel suggest that levels of these proteins are perturbed as a function of the catalytic activity of the EGFR, but their known roles do not immediately suggest a mechanism for the observed behavior.

To demarcate the relative positions of each of the panel proteins within the broader EGFR signaling axis, the impact on their abundance by inhibition of MAPK and AKT pathways was assessed. A431 cells were treated with either an AKT pathway specific tyrosine kinase inhibitor (LY294002) or a MAPK-specific TKI (PD98059). The majority of the panel proteins showed a change in abundance with one of these treatments (Table I). Specifically, BAG4, CBFB, QARS, and TNFAIP2 showed a change in abundance in response to AKT inhibition, and CAD17, PDCD4, S100A9, SERPINE1, and Testican-2 showed a change in abundance in response to MAPK inhibition. ELAVL-1, EpCAM, HSPG2, TROP2, and SNX5 were unchanged by treatment of cells with either TKI. Claudin-1 was the only protein that had changes in expression in the presence of both TKIs. In aggregate, the TKI inhibition data suggest that when EGFR signaling is perturbed, protein level changes are effected at various biological nodes. The proteins that were not perturbed upon treatment with either a MAPK or an AKT TKI are either upstream of these pathways or are part of another pathway.

Potential a Priori and Post-Therapy Predictors of Therapeutic Response in Lung Cancer Cell Lines:

As noted above, EGFR targeted therapies are extensively used in the treatment of non-small cell lung cancer. Consequently, to demonstrate that the gefitinib induced protein level change is not specific to the A431 model, this study investigated the generality of the selected protein panel across a set of NSCLC cell lines with varying sensitivity to gefitinib (Table I). Gefitinib inhibits the phosphorylation of EGFR in HCC827, H1650, and H23 cell lines and is ineffective in H1975 cells as a result of the T790M mutation in EGFR kinase (31). There was clear concordance of the treatment-induced changes of protein abundance in the gefitinib-sensitive (HCC827, H1650) lines than in the gefitinib-resistant (H23, H1975) lines. Significant increase in the abundances of EpCAM, HSPG2, PDCD4, ELAVL-1, and TNFAIP2 were observed in the gefitinib-sensitive lines upon treatment. Basal protein abundance was also measured across eight NSCLC lines (HCC827, H2935, H3255, H1666, H1650, H1975, H2235, H23) and revealed a relation between protein level and $IC_{50}$ for many proteins in the panel, suggesting that, in addition to monitoring of therapeutic response, the levels of these proteins may correlate with gefitinib response a priori (data not shown).

Figure 3A:
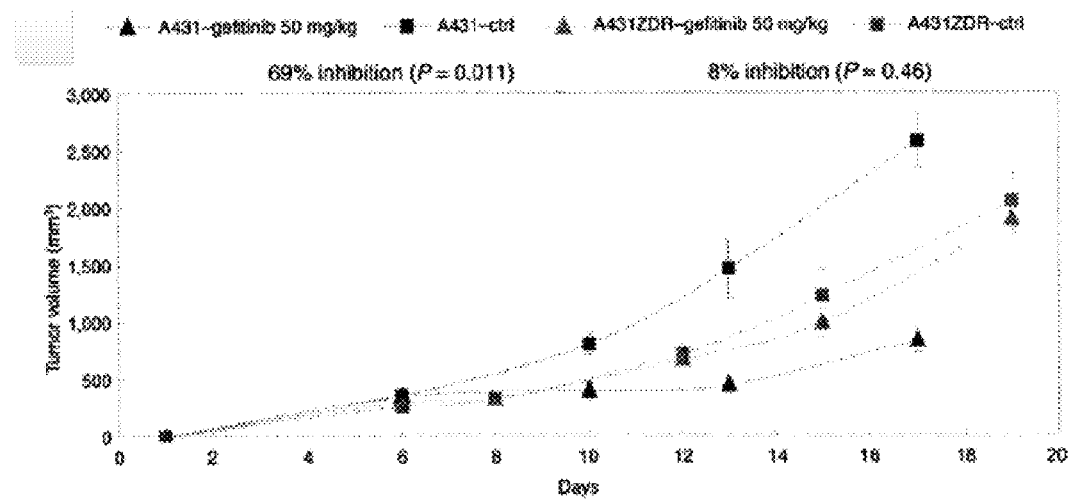
FIGS. 3A-3B illustrate that A431 tumors are responsive to gefitinib in vivo.
Figure 3B:
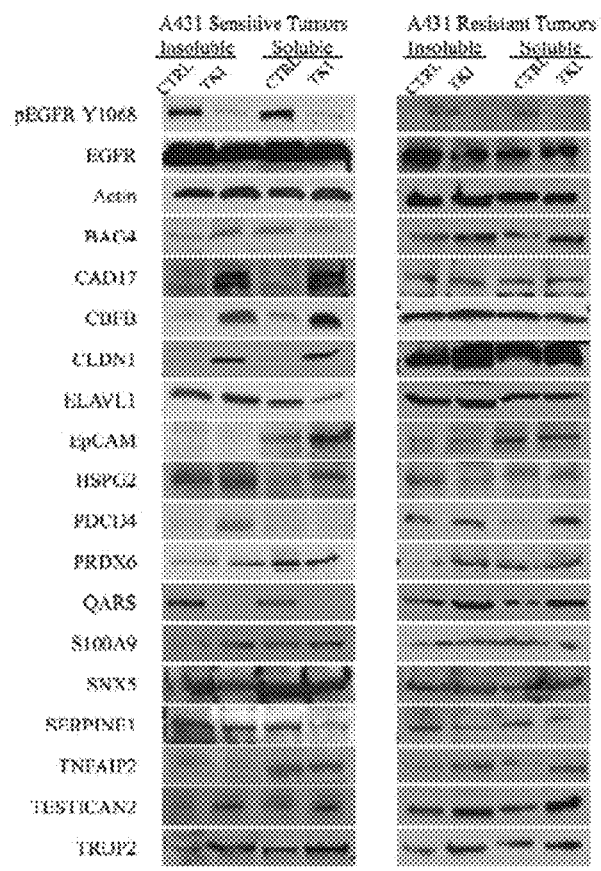

In Vitro Response Profile Also Observed In Vivo:

Next, the expression and gefitinib-induced perturbation of the proteins in the panel were measured in an A431 xenograft model. Mice were treated with 50 mg/kg gefitinib or vehicle control after tumors became palpable. In mice treated with gefitinib, tumors were significantly smaller than those in untreated mice and grew at a slower rate (FIG. 3A). Tumors and sera were collected at the experimental endpoint, and abundance of the panel proteins was determined. Tumor lysates were fractionated to separate cell lysates into intracellular and membrane fractions. Dose-dependent changes in abundance were measured for the 16 proteins and compared to levels in untreated animals. The changes observed in vivo for 12 of the 16 proteins were concordat with results from in vitro experiments (FIG. 3B). The dose-dependent changes in abundance were not identical in the cell-surface and the intracellular sub-proteomes. For proteins like PRDX6, which was chosen for validation based on its fold change in the whole-cell profiling experiments, the change in abundance in the insoluble (membrane) fraction was greater than that in the soluble fraction.

Protein Panel Differentiates Sensitive and Resistant A431 Tumors In Vivo:

To test whether some of these proteins may distinguish the response phenotype of tumors to EGFR kinase inhibitors in vivo, the basal levels and response to therapy of the markers were compared in an in vivo derived xenograft model resistant to gefitinib (A431-ZDR). This line maintains wild-type EGFR. In addition, K-ras alleles and PTEN levels are identical to those in the parent A431 tumors. No differences in tumor growth rates were observed when animals treated with gefitinib were compared with untreated controls (FIG. 3A) even though EGFR was down-regulated in tumors from treated animals (FIG. 3B). In all xenograft experiments, the serum concentration of gefitinib was 150+/−50 nM. CAD17, CBFB, ELAVL-1, EpCAM, HSPG-2, QARS, S100A9, SNX5, SERPINE1, Testican 2, and TROP-2 expression changes were different in the A431-ZDR tumors than in the A431 tumors (FIG. 3B). This illustrates that certain panel proteins are correlative to response to gefitinib.

Figure 4:
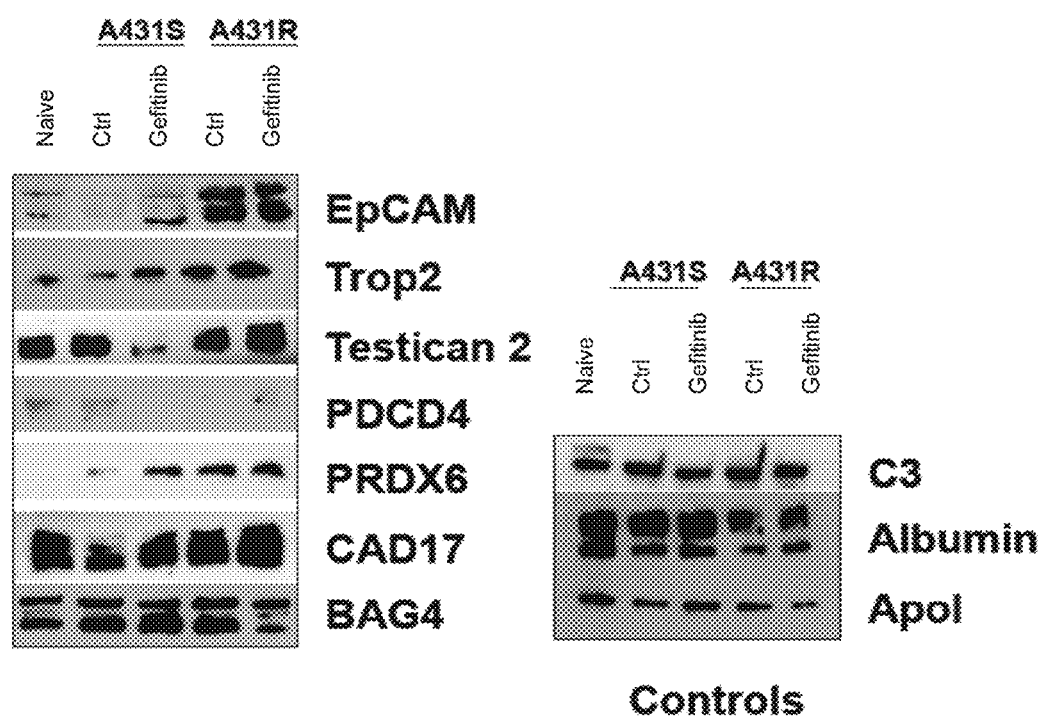
FIG. 4 illustrates analysis of panel proteins from serum of animals bearing gefitinib-sensitive and gefitinib-resistant tumors. Sera were collected from naïve mice and mice implanted with A431 cells and A431-ZDR tumors and analyzed by immunoblot for the 16 proteins in the panel. Seven of the 16 proteins were detectable in sera.

Protein Panel Differentiates Sensitive and Resistant A431 Tumors in Analysis of Serum from Tumor-Bearing Mice:

Sera from mice implanted with either A431 or A431-ZDR tumors were collected and immunoblots were performed. When these mice were treated with gefitinib, dose-dependent changes were observed in EpCAM, TROP2, and PRDX6 that differed in mice implanted with gefitinib sensitive and resistant tumor cells. In addition, the data differentiated sera from sensitive and resistant mice as the serum concentrations of EpCAM and PRDX6 were significantly higher in the A431-ZDR serum than in A431 serum (FIG. 4).

Discussion

The present example employed quantitative proteomics to identify a panel of proteins whose change in abundance upon treatment correlates with sensitivity to EGFR tyrosine kinase inhibition across a number of cell lines and in an in vivo (iso-genic sensitive/resistant) xenograft model. The results demonstrated differences between baseline abundance and levels of certain proteins after gefitinib treatment in gefitinib-sensitive versus resistant NSCLC cell lines (Table I). Several proteins showed changes dependent on gefitinib treatment in an in vivo tumor model (FIG. 3). The results presented highlight a proteomics paradigm where discovery in vitro successfully translates to concordant behavior in vivo. In addition, this model-based, but broad-scale approach allowed for significant and diverse investigation of the specificity and generality of discovered proteins. Although forty-eight proteins previously associated with EGFR signaling (32) were identified and quantified in the analysis, they showed no significant changes in abundance in response to EGFR targeted therapies. The average fold increase in abundance of these proteins was 0.98 in the intracellular fraction and 1.04 in the cell-surface sub-proteome.

The biological functions of the proteins identified in this study are diverse and (with the exception of SNX5, which has been implicated in membrane trafficking and degradation of the EGFR (34)) have not been previously implicated in EGFR function. Two of the proteins identified in this study, EpCAM and TROP2, have been implicated in gefitinib resistance (35, 36). In A431 cells and gefitinib-sensitive NSCLC cell lines, the expression of EpCAM and TROP2 was up-regulated upon gefitinib treatment (FIGS. 2-4), and the serum concentration of EpCAM was higher in mice implanted with gefitinib-resistant xenografts than gefitinib-sensitive cells. The basal levels of EpCAM in NSCLC cell lines also correlated with gefitinib resistance. PDCD4 is the only protein identified that was previously shown to function downstream of the EGFR signaling pathway. PDCD4 up-regulation is associated with increased c-jun transcriptional activity (37). PDCD4 expression was modulated by RAS/MAPK activity and gefitinib treatment in gefitinib-sensitive NSCLC cell lines (Table I). The other proteins in this panel have been implicated in various biological functions ranging from protein biosynthesis to regulation of fibrinolysis, demonstrating the biological reach of the EGFR signaling pathway. The reasons for the perturbation of levels of these proteins observed in A431 and NSCLC cell lines are unclear but an understanding of the involvement of these proteins in gefitinib resistance is worth pursuing EGFR was also observed to change glycosylation state, but not total abundance, in response to gefitinib treatment. By overlaying total protein fold change (+1.18 compared to untreated cells) with the N-linked glycosylation data, a region within domain III of EGFR extracellular domain was identified that demonstrated a dose-dependent decrease in glycosylation at N356 (data not shown). This is relevant to EGFR biology because N-linked glycosylation of EGFR impacts ligand binding(38), alters receptor self-association and activity(39), and modulates the effectiveness of EGFR-TKIs(40).

A component for this model-based discovery-based proteomic experiments is the translation of in vitro, model-based, perturbations to complex, in vivo, model systems. There are many steps in this process, from the initial discovery, through diverse verification steps and the development of assays for clinical application. The present study demonstrated that an in vitro model system for EGFR signaling may be utilized to predict gefitinib induced changes in NSCLC cell lines and in vivo xenografts. Such studies go beyond verifying the accuracy of mass-spectrometry results, but instead delve into the biological origins and consequences of observed quantitative events. Such studies are highly unique and allow an investigation into both the generality and specificity of putative marker studies. The present example demonstrates that in vitro model-based systems may be used to identify protein level changes that are recapitulated in complex systems. The present study utilized a compartment based strategy to enhance the likelihood for the translation of any putative biomarker to a clinical tool. Since most of the selected markers were not immediate family members of EGFR, the gefitinib inhibition profile was compared with that of two downstream nodes of EGFR signaling (MAPK and AKT). By investigating the protein profile of candidates across a large number of lung cancer cell lines, the generality of the marker panel was confirmed. By contrasting the impact of inhibition with EGFR (gefitinib) to MAPK(PD98059), AKT(LY294002), to that of a non-EGFR cytotoxic agent (paclitaxel) specificity of response was determined.

In this example, a panel of proteins was obtained via quantitative proteomic comparison of cells that overexpresses the EGFR before and after treatment with an inhibitor of EGFR kinase. The proteins up-regulated upon gefitinib treatment appear to be connected to the EGFR-kinase activity, and changes in expression are indicative of cellular network responsiveness to the targeted therapeutic agent. Expression changes were significantly concordant between in vitro and in vivo systems, suggesting that in vitro models may be generally used as a discovery environment. Five of the sixteen proteins have been observed in the sera of lung cancer patients, and at least two representative peptides from each of the sixteen proteins identified in this study have been identified by various research groups and deposited in Human Plasma PeptideAtlas(43) and/or PRIDE(44). The biological relevance of tumor-derived proteins may be easier to assess, and a variety of quantitative proteomic techniques are currently applicable in vitro and in vivo.

relapse and survival with amplification of the HER-2/neu oncogene. Science. 1987; 235:177-82.
2. Di Fiore P P, Pierce J H, Fleming T P, Hazan R, Ullrich A, King C R, et al. Overexpression of the human EGF receptor confers an EGF-dependent transformed phenotype to NIH 3T3 cells. Cell. 1987; 51:1063-70.
3. Arteaga C L, Baselga J. Tyrosine kinase inhibitors: why does the current process of clinical development not apply to them? Cancer Cell. 2004; 5:525-31.
4. Ullrich A, Riedel H, Yarden Y, Coussens L, Gray A, Dull T, et al. Protein kinases in cellular signal transduction: tyrosine kinase growth factor receptors and protein kinase C. Cold Spring Harb Symp Quant Biol. 1986; 51 Pt 2:713-24.
5. Citri A, Yarden Y. EGF-ERBB signalling: towards the systems level. Nat Rev Mol Cell Biol. 2006; 7:505-16.
6. Morandell S, Stasyk T, Skvortsov S, Ascher S, Huber L A. Quantitative proteomics and phosphoproteomics reveal novel insights into complexity and dynamics of the EGFR signaling network. Proteomics. 2008; 8:4383-401.
7. Zhang X, Pickin K A, Bose R, Jura N, Cole P A, Kuriyan J. Inhibition of the EGF receptor by binding of MIG6 to an activating kinase domain interface. Nature. 2007; 450:741-4.
8. Engelman J A, Janne P A. Mechanisms of acquired resistance to epidermal growth factor receptor tyrosine kinase inhibitors in non-small cell lung cancer. Clin Cancer Res. 2008; 14:2895-9.
9. Riely G J. The use of first-generation tyrosine kinase inhibitors in patients with NSCLC and somatic EGFR mutations. Lung Cancer. 2008; 60 Suppl 2:S19-22.

TABLE I

Cross Validation of Protein Panel across NSCLC Tissue and Treatments.
Dose-dependent change in protein levels were measured by western blot (data not shown) and are marked with (+) for increase, (−) for decrease, (N.C) for no change, and (~) for not detected. The cell lines have various sensitivities for gefitinib: A431, IC$_{50}$ = 40-80 nM; HCC827, 100 nM; H1650, 1 μM; H23, 8 μM; and H1975, 12 μM. Protein level changes of the panel of proteins after treatment with selective inhibitors of MAPK (PD 98059), AKT (LY294002), erlotinib (on-axis control), and paclitaxel (off-axis control) are shown.
Table 1: Cross Validation of Protein Panel across NSCLC Tissue, and Treatments

| Tissue gefitinib IC $_{50}$[nM] Treatment | A431 0.5 gefitinib | HCC827 0.1 gefitinib | H1650 1.0 gefitinib | H23 8.0 gefitinib | H1975 12.0 gefitinib | A431 AKT (A6730) | A431 MAPK (PD98059) | A431 erlotinib | A431 paclitaxel |
|---|---|---|---|---|---|---|---|---|---|
| BAG4 | + | N.C. | N.C. | + | N.C. | + | N.C. | + | N.C. |
| CAD17 | + | + | + | + | N.C. | N.C. | + | + | N.C. |
| CBFB | + | + | + | N.C. | N.C. | + | N.C. | + | N.C. |
| Claudin 1 | + | N.C. | + | N.C. | N.C. | + | + | + | N.C. |
| ELAVL-1 | + | + | + | N.C. | N.C. | N.C. | N.C. | + | N.C. |
| EpCAM | + | + | + | N.C. | N.C. | N.C. | N.C. | + | N.C. |
| HSPG2 | + | N.C. | + | N.C. | N.C. | N.C. | N.C. | + | N.C. |
| PDCD4 | + | + | + | N.C. | N.C. | N.C. | + | + | N.C. |
| PRDX6 | + | + | + | N.C. | N.C. | N.C. | + | + | N.C. |
| QARS | + | + | + | N.C. | ~ | + | N.C. | + | N.C. |
| S100A9 | + | + | N.C. | N.C. | N.C. | N.C. | + | + | N.C. |
| SNX5 | − | − | N.C. | N.C. | N.C. | N.C. | N.C. | − | N.C. |
| SERPINE1 | + | + | + | N.C. | N.C. | N.C. | + | + | N.C. |
| TNFAIP2 | + | N.C. | + | + | N.C. | + | N.C. | + | N.C. |
| TESTICAN2 | + | + | N.C. | ~ | N.C. | N.C. | + | + | N.C. |
| TROP-2 | + | + | + | N.C. | N.C. | N.C. | N.C. | + | N.C. |

References for Example 1

The following references are incorporated by reference in pertinent part.
1. Slamon D J, Clark G M, Wong S G, Levin W J, Ullrich A, McGuire W L. Human breast cancer: correlation of
10. Cohen M H, Williams G A, Sridhara R, Chen G, Pazdur R. FDA drug approval summary: gefitinib (ZD1839) (Iressa) tablets. Oncologist. 2003; 8:303-6.
11. Harari P M. Epidermal growth factor receptor inhibition strategies in oncology. Endocr Relat Cancer. 2004; 11:689-708.

12. Rubin B P, Duensing A. Mechanisms of resistance to small molecule kinase inhibition in the treatment of solid tumors. Lab Invest. 2006; 86:981-6.
13. Rho J K, Choi Y J, Lee J K, Ryoo B Y, Na, I I, Yang S H, et al. Epithelial to mesenchymal transition derived from repeated exposure to gefitinib determines the sensitivity to EGFR inhibitors in A549, a non-small cell lung cancer cell line. Lung Cancer. 2009; 63:219-26.
14. Thomson S, Petti F, Sujka-Kwok I, Epstein D, Haley J D. Kinase switching in mesenchymal-like non-small cell lung cancer lines contributes to EGFR inhibitor resistance through pathway redundancy. Clin Exp Metastasis. 2008; 25:843-54.
15. Guo A, Villen J, Kornhauser J, Lee K A, Stokes M P, Rikova K, et al. Signaling networks assembled by oncogenic EGFR and c-Met. Proc Natl Acad Sci USA. 2008; 105:692-7.
16. Engelman J A, Zejnullahu K, Mitsudomi T, Song Y, Hyland C, Park J O, et al. MET amplification leads to gefitinib resistance in lung cancer by activating ERBB3 signaling. Science. 2007; 316:1039-43.
17. Pao W, Miller V A, Politi K A, Riely G J, Somwar R, Zakowski M F, et al. Acquired resistance of lung adenocarcinomas to gefitinib or erlotinib is associated with a second mutation in the EGFR kinase domain. PLoS Med. 2005; 2:e73.
18. Sordella R, Bell D W, Haber D A, Settleman J. Gefitinib-sensitizing EGFR mutations in lung cancer activate anti-apoptotic pathways. Science. 2004; 305:1163-7.
19. Lynch T J, Bell D W, Sordella R, Gurubhagavatula S, Okimoto R A, Brannigan B W, et al. Activating mutations in the epidermal growth factor receptor underlying responsiveness of non-small-cell lung cancer to gefitinib. N Engl J Med. 2004; 350:2129-39.
20. Ullrich A, Coussens L, Hayflick J S, Dull T J, Gray A, Tam A W, et al. Human epidermal growth factor receptor cDNA sequence and aberrant expression of the amplified gene in A431 epidermoid carcinoma cells. Nature. 1984; 309:418-25.
21. Bryant J A, Finn R S, Slamon D J, Cloughesy T F, Charles A C. EGF activates intracellular and intercellular calcium signaling by distinct pathways in tumor cells. Cancer Biol Ther. 2004; 3:1243-9.
22. Oyama M, Kozuka-Hata H, Tasaki S, Semba K, Hattori S, Sugano S, et al. Temporal perturbation of tyrosine phosphoproteome dynamics reveals the system-wide regulatory networks. Mol Cell Proteomics. 2009; 8:226-31.
23. Ong S E, Mann M. A practical recipe for stable isotope labeling by amino acids in cell culture (SILAC). Nat Protoc. 2006; 1:2650-60.
24. Faca V, Pitteri S J, Newcomb L, Glukhova V, Phanstiel D, Krasnoselsky A, et al. Contribution of protein fractionation to depth of analysis of the serum and plasma proteomes. J Proteome Res. 2007; 6:3558-65.
25. Rauch A, Bellew M, Eng J, Fitzgibbon M, Holzman T, Hussey P, et al. Computational Proteomics Analysis System (CPAS): an extensible, open-source analytic system for evaluating and publishing proteomic data and high throughput biological experiments. J Proteome Res. 2006; 5:112-21.
26. Keller A, Nesvizhskii A I, Kolker E, Aebersold R. Empirical statistical model to estimate the accuracy of peptide identifications made by MS/MS and database search. Anal Chem. 2002; 74:5383-92.
27. Nesvizhskii A I, Keller A, Kolker E, Aebersold R. A statistical model for identifying proteins by tandem mass spectrometry. Anal Chem. 2003; 75:4646-58.
28. Zhou Y, Aebersold R, Zhang H. Isolation of N-linked glycopeptides from plasma. Anal Chem. 2007; 79:5826-37.
29. Wakeling A E, Guy S P, Woodburn J R, Ashton S E, Curry B J, Barker A J, et al. ZD1839 (Iressa): an orally active inhibitor of epidermal growth factor signaling with potential for cancer therapy. Cancer Res. 2002; 62:5749-54.
30. Zhang Y, Xiang L, Hassan R, Paik C H, Carrasquillo J A, Jang B S, et al. Synergistic antitumor activity of taxol and immunotoxin SS1P in tumor-bearing mice. Clin Cancer Res. 2006; 12:4695-701.
31. Yun C H, Mengwasser K E, Toms A V, Woo M S, Greulich H, Wong K K, et al. The T790M mutation in EGFR kinase causes drug resistance by increasing the affinity for ATP. Proc Natl Acad Sci USA. 2008; 105: 2070-5.
32. Dennis G, Jr., Sherman B T, Hosack D A, Yang J, Gao W, Lane H C, et al. DAVID: Database for Annotation, Visualization, and Integrated Discovery. Genome Biol. 2003; 4:P3.
33. Calvano S E, Xiao W, Richards D R, Felciano R M, Baker H V, Cho R J, et al. A network-based analysis of systemic inflammation in humans. Nature. 2005; 437: 1032-7.
34. Liu H, Liu Z Q, Chen C X, Magill S, Jiang Y, Liu Y J. Inhibitory regulation of EGF receptor degradation by sorting nexin 5. Biochem Biophys Res Commun. 2006; 342:537-46.
35. Frederick B A, Helfrich B A, Coldren C D, Zheng D, Chan D, Bunn P A, Jr., et al. Epithelial to mesenchymal transition predicts gefitinib resistance in cell lines of head and neck squamous cell carcinoma and non-small cell lung carcinoma. Mol Cancer Ther. 2007; 6:1683-91.
36. Yauch R L, Januario T, Eberhard D A, Cavet G, Zhu W, Fu L, et al. Epithelial versus mesenchymal phenotype determines in vitro sensitivity and predicts clinical activity of erlotinib in lung cancer patients. Clin Cancer Res. 2005; 11:8686-98.
37. Yang H S, Matthews C P, Clair T, Wang Q, Baker A R, Li C C, et al. Tumorigenesis suppressor Pdcd4 down-regulates mitogen-activated protein kinase kinase kinase 1 expression to suppress colon carcinoma cell invasion. Mol Cell Biol. 2006; 26:1297-306.
38. Cummings R D, Soderquist A M, Carpenter G. The oligosaccharide moieties of the epidermal growth factor receptor in A-431 cells. Presence of complex-type N-linked chains that contain terminal N-acetylgalactosamine residues. J Biol Chem. 1985; 260:11944-52.
39. Fernandes H, Cohen S, Bishayee S. Glycosylation-induced conformational modification positively regulates receptor-receptor association: a study with an aberrant epidermal growth factor receptor (EGFRvIII/DeltaEGFR) expressed in cancer cells. J Biol Chem. 2001; 276:5375-83.
40. Ling Y H, Li T, Perez-Soler R, Haigentz M, Jr. Activation of E R stress and inhibition of EGFR N-glycosylation by tunicamycin enhances susceptibility of human non-small cell lung cancer cells to erlotinib. Cancer Chemother Pharmacol. 2009; 64:539-48.
41. Myers M V, Manning H C, Coffey R J, Liebler D C. Protein expression signatures for inhibition of epidermal growth factor receptor mediated signaling. Mol Cell Proteomics. 2011.

42. Fang Q, Kani K, Faca V M, Zhang W, Zhang Q, Jain A, et al. Impact of protein stability, cellular localization, and abundance on proteomic detection of tumor-derived proteins in plasma. PLoS One. 2011; 6:e23090.
43. Deutsch E W, Eng J K, Zhang H, King N L, Nesvizhskii A I, Lin B, et al. Human Plasma PeptideAtlas. Proteomics. 2005; 5:3497-500.
44. Barsnes H, Vizcaino J A, Eidhammer I, Martens L. PRIDE Converter: making proteomics data-sharing easy. Nat Biotechnol. 2009; 27:598-9.

Example 2

PRDX6 as a Blood Biomarker for Monitoring Response to Anti-EGFR Therapy

Targeted therapies directed against the epidermal growth factor receptor (EGFR) are commonly employed in the treatment of several different types of cancer. Although the majority of patients treated with these agents show a short-term response, nearly all patients inevitably develop resistance at some point during therapy. Despite the need to detect the onset of treatment resistance as early as possible, clinicians currently lack an effective way to routinely monitor response over the full duration of treatment. The present example describes the use of serial blood sampling from xenograft mouse models together with enzyme-linked immunosorbent assays to show that the peroxiredoxin family member PRDX6 is a robust blood biomarker of response to anti-EGFR therapy. The following results demonstrate that early changes in serum levels of PRDX6 during the course of anti-EGFR therapy can discriminate between responding and non-responding tumors. This approach offers a number of compelling advantages over current imaging-based strategies for monitoring response to targeted therapeutics.

Results

Biomarker Selection

To select candidate blood biomarkers of gefitinib response proteomic data derived from a pilot cell culture study via quantitative mass spectrometry was used'. This data included differential proteomic changes in cell lysates at 16 hours post-treatment between gefitinib treated and vehicle treated A431 cells. Initial focus was on five proteins that increased significantly in A431 cell lysates following treatment with gefitinib, namely: epithelial cell adhesion molecule (EpCAM), peroxiredoxin 6 (PRDX6), tumor-associated calcium signal transducer 2 (TACSTD2 or TROP2), claudin 1 (CLDN1), and sparc/osteonectin, cwcv and kazal-like domains proteoglycan (testican) 2 (SPOCK2).

In pilot experiments with subcutaneous xenograft mouse models derived from the A431 cell line, consistent detection of PRDX6 was possible by ELISA with as little as 40 µl of serum. The ability to detect PRDX6 in very small volumes of blood that could be collected serially via submandibular bleeds offered the possibility of monitoring PRDX6 levels in individual animals during the course of therapy. Therefore, efforts were focused on investigating PRDX6 as a potential blood biomarker of gefitinib response.

PRDX6 Changes after Gefitinib Treatment in Cell Culture

The first experiments focused on PRDX6 changes in cell culture following gefitinib treatment of the cell lines A431 and HCC827, both of which are sensitive to anti-EGFR therapy[8,9]. A431 is an epidermoid cancer cell line that exhibits high expression of wild-type EGFR[10] and is considered a model system for the study of EGFR. Conversely, HCC827 is a non-small cell lung cancer cell line that is characterized by high expression of EGFR together with a deletion in exon 19 of the EGFR domain that sensitizes it to anti-EGFR TKIs[9].

A431 and HCC827 cells were plated onto 100 mm tissue culture plates, and treated with either gefitinib or vehicle (DMSO). For each treatment group, plates were collected at 0, 4, 8, 16, 24 and 32 hours after the start of treatment, and PRDX6 protein levels in both cell media and cell lysate measured by sandwich ELISA. The PRDX6 ELISA antibody pair, antibody concentration and incubation time were optimized to achieve the sensitivity, reproducibility and robustness in the presence of serum.

Figure 5A:
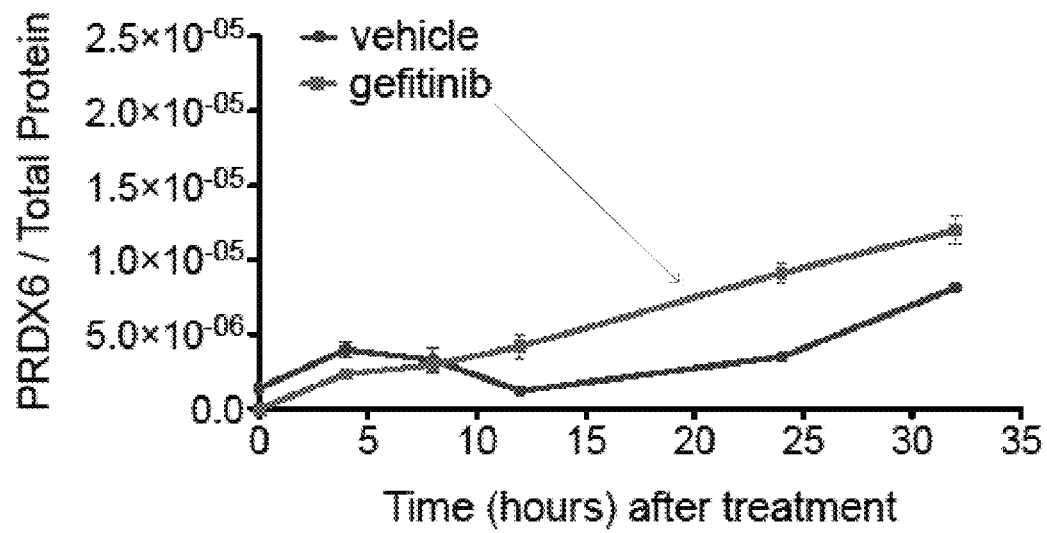
FIGS. 5A-5B are a series of graphs illustrating changes in PRDX6 (normalized to total protein) for A431 and HCC827 cells after treatment with either vehicle or gefitinib.
Figure 5B:
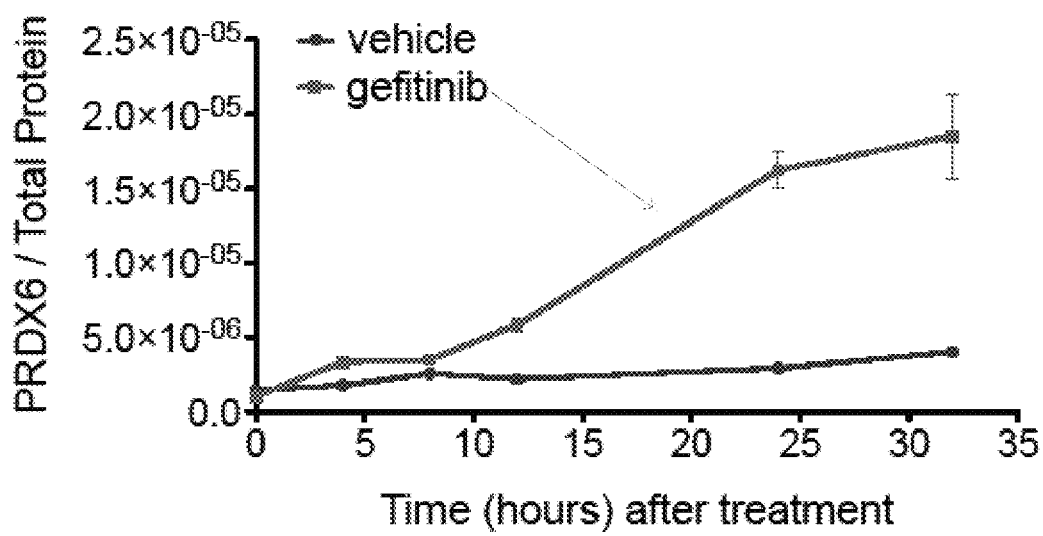
Figure 5C:
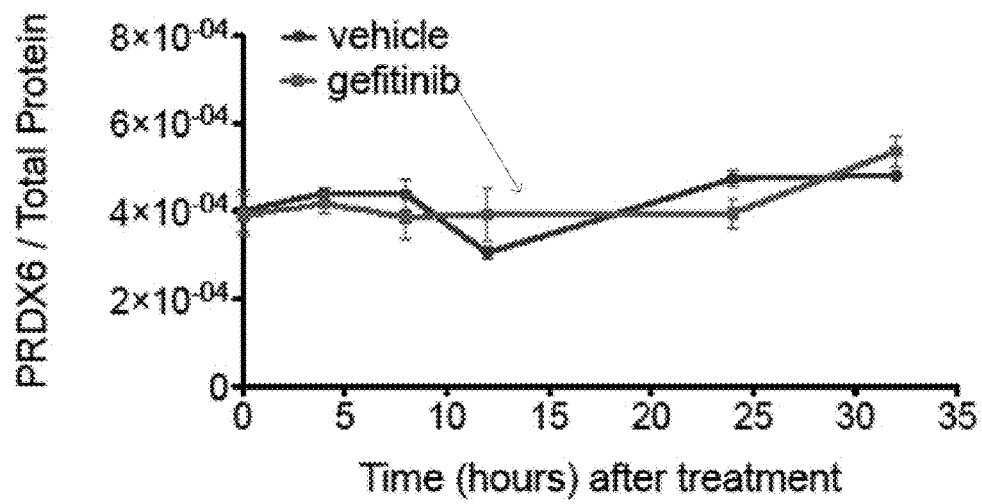
FIGS. 5C and 5D show PRDX6 levels in cell lysate over the course of 32 hours after treatment for A431 and HCC827 cells, respectively. All error bars represent one standard error of the mean.
Figure 5D:
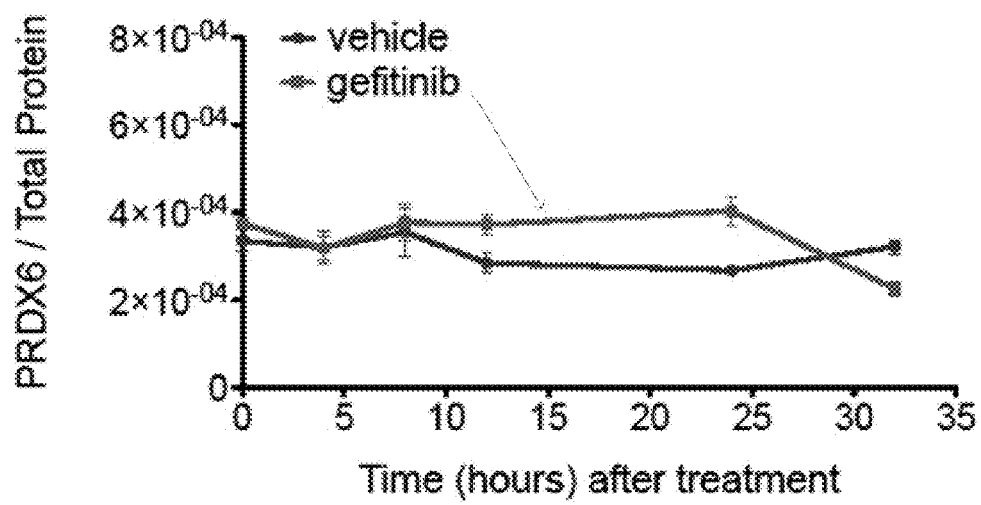

PRDX6 levels in cell media from A431 cells treated with either vehicle or gefitinib increased after treatment, although the increase was significantly greater for gefitinib treated compared with vehicle treated cells (FIG. 5A). Specifically, the difference in mean PRDX6 between vehicle and gefitinib treated A431 cells was statistically significant at 12 hours ($P=0.025$) and 24 hours ($P=0.0062$), but not at 32 hours ($P=0.0513$). For HCC827 cells, PRDX6 levels in cell media increased substantially after gefitinib treatment, whereas there was no significant change after treatment with vehicle (FIG. 5B). The difference in mean PRDX6 between vehicle and gefitinib treated HCC827 cells was statistically significant at 12 hours ($P=0.0018$), 24 hours ($P=0.0003$), and 32 hours ($P=0.0069$). There was no significant difference in mean PRDX6 in A431 cell lysate at any time point (FIG. 5C). In the case of HCC827, PRDX6 was significantly higher in cell lysates from gefitinib treated compared with vehicle treated cells at 12 hours ($P=0.0442$) and 24 hours ($P=0.016$), and significantly lower at 32 hours ($P=0.0129$) (FIG. 5D).

Serum PRDX6 Changes in Gefitinib Treated A431 Xenografts

Figure 6A:
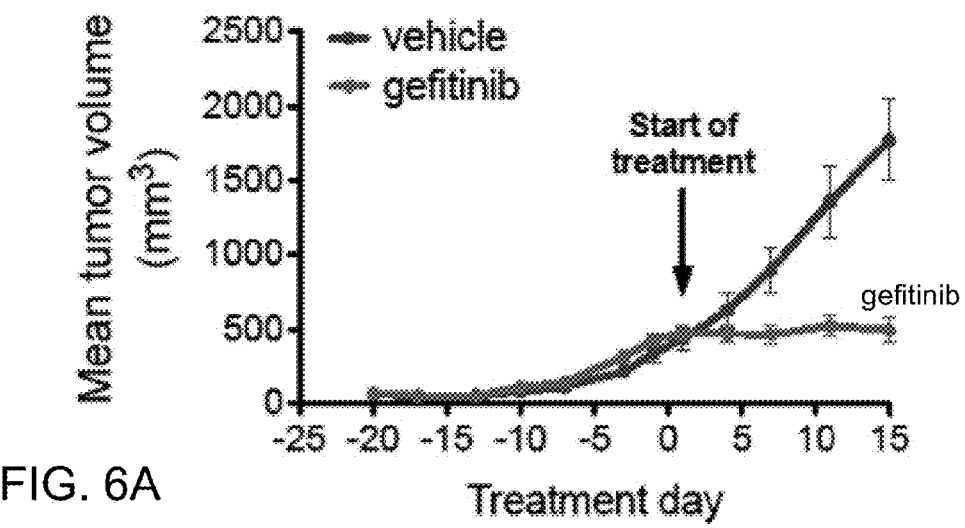
FIGS. 6A-6B illustrate changes in PRDX6 for A431 xenografts treated with either vehicle or gefitinib.
Figure 6B:
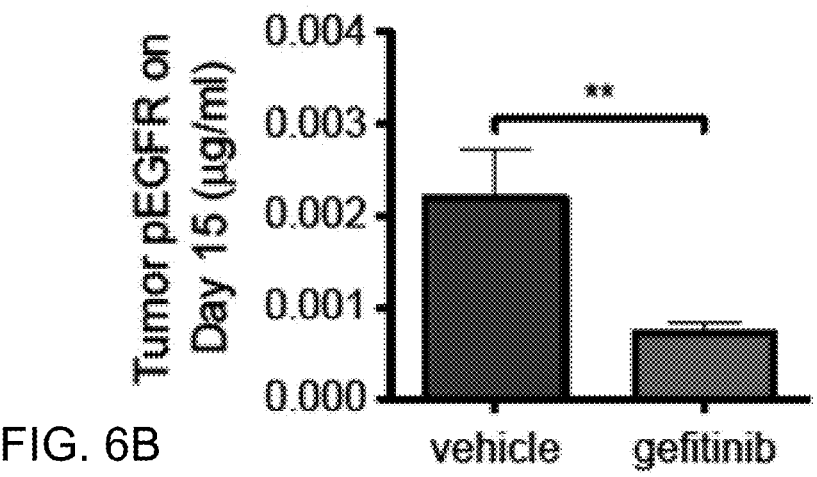

To test if the gefitinib-induced changes in PRDX6 that were observed in cell culture could also be detected in vivo, a subcutaneous xenograft study was performed using the A431 cell line in mice. A431 xenografts treated with gefitinib exhibited a marked arrest in tumor growth that was maintained throughout the course of treatment (FIG. 6A). The difference in tumor volumes between vehicle and gefitinib treated mice was statistically significant at Day 7 ($P=0.0102$), Day 11 ($P=0.002$) and Day 15 ($P=0.0001$). To confirm the anti-EGFR effects of gefitinib, phospho-EGFR levels were analyzed in tumors from vehicle and gefitinib treated mice collected at the end of the study (FIG. 6B). Mean phospho-EGFR levels in the tumor lysates from gefitinib treated mice were significantly lower ($P=0.008$) compared with the vehicle treated mice.

Figure 6C:
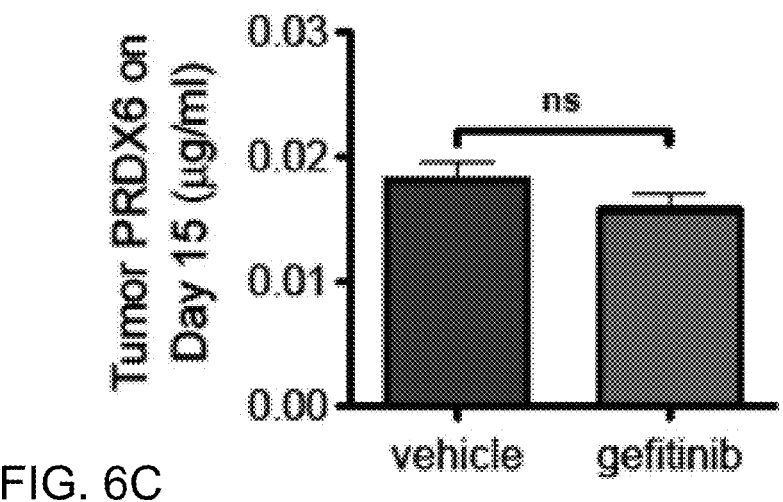
FIG. 6C is a graph illustrating levels of PRDX6 (normalized to total protein) in tumor lysates collected on day 15.

To understand the effect of gefitinib on PRDX6 in A431 xenografts, levels of PRDX6 were first assayed in tumor lysates (FIG. 6C). There was no statistically significant difference in tumor PRDX6 between the vehicle and gefitinib-treated xenografts ($P=0.2185$).

Figure 6D:
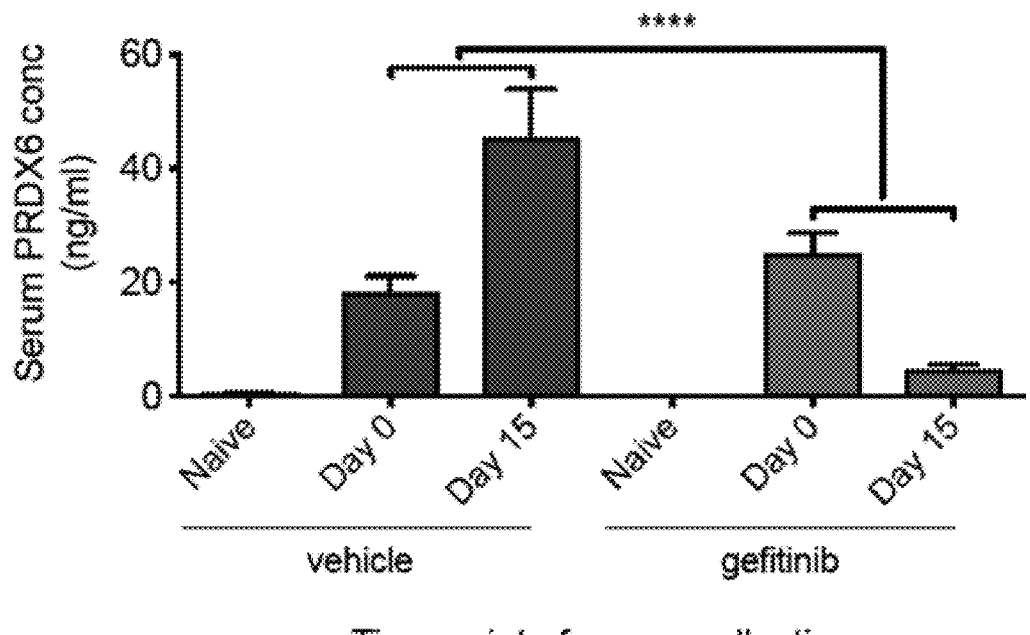
FIG. 6D illustrates serum PRDX6 levels in naïve (pre-inoculation), Day 0 (pre-treatment) and Day 15 (post-treatment) blood samples.

Next, serum levels of PRDX6 were analyzed from blood samples collected prior to tumor inoculation (naïve), immediately before the start of treatment (Day 0), and at the end of the study (Day 15). Naïve serum samples from all mice showed only trace levels of PRDX6 that were indistinguishable from background on the ELISA for the majority of samples (FIG. 6D). Mean serum PRDX6 levels between Day 0 and Day 15 increased in xenografts treated with vehicle and decreased in xenografts treated with gefitinib (FIG. 6D). The difference in the mean change from baseline in serum PRDX6 between vehicle and gefitinib treated animals was statistically significant ($P<0.0001$).

Figure 6E:
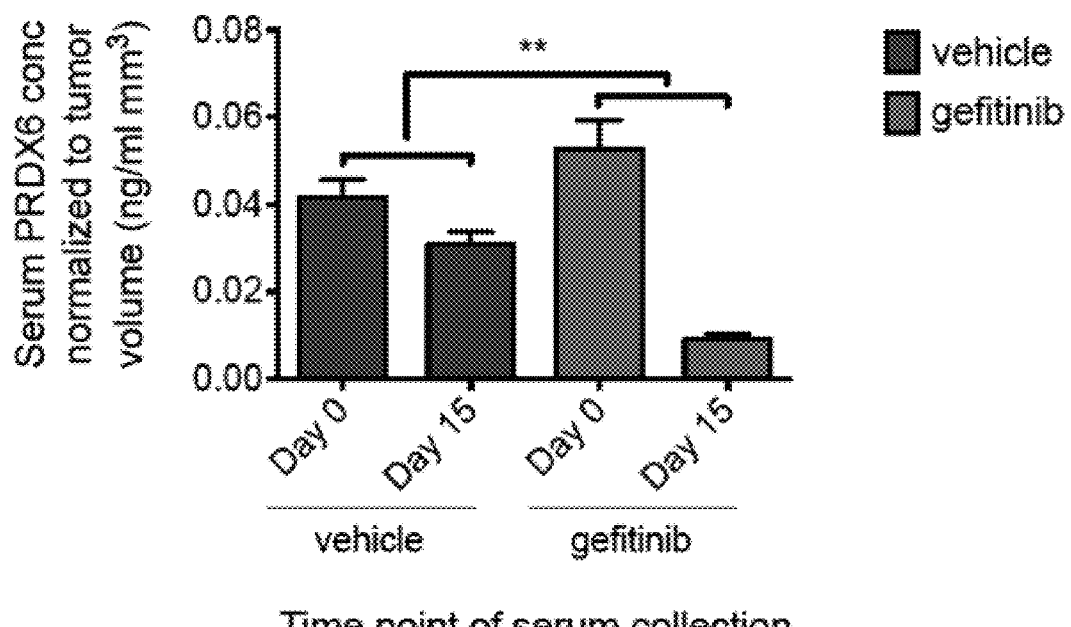
FIG. 6E is a bar graph illustrating serum PRDX6 levels normalized to tumor volume. All error bars represent one standard error of the mean. Key: ns—not significant, * $P<0.05$,  $P<0.01$, * $P<0.001$, **** $P<0.0001$.

To understand the effect of tumor growth on serum PRDX6 levels during the course of therapy, the correlation between PRDX6 levels and tumor volume were analyzed in both vehicles treated and gefitinib treated animals. Serum PRDX6 levels from A431 xenografts treated with vehicle exhibited a highly significant correlation with tumor volume ($R^2=0.93$, $P<0.0001$), whereas there was no correlation in xenografts treated with gefitinib ($R^2=0.08$, $P=0.24$). To evaluate whether the observed difference in serum PRDX6 changes between vehicle and gefitinib treated mice could be explained by the difference in tumor burden, serum PRDX6 levels were normalized to tumor volume and compared between the two treatment groups (FIG. 6E). Notably, the difference in the mean change from baseline in serum PRDX6 normalized to tumor volume was statistically significant ($P=0.0027$).

Serum PRDX6 Changes in Gefitinib Treated NSCLC Xenografts

To determine if gefitinib induced changes in serum PRDX6 levels generalized to tumors derived from non-small cell lung cancer cell lines, a xenograft mouse model study was performed using the NSCLC cell lines HCC827 and H1975, which are sensitive and resistant to gefitinib, respectively[9,11]. The H1975 cell line is characterized by the double mutation L858R/T790Min the EGFR kinase domain. The L858R mutation results in a dramatic increase in EGFR activity, while the T790M mutation impairs the ability of reversible EGFR TKIs to bind to the ATP binding domain of the EGFR kinase and, hence, provides resistance to these agents.

Figure 7A:
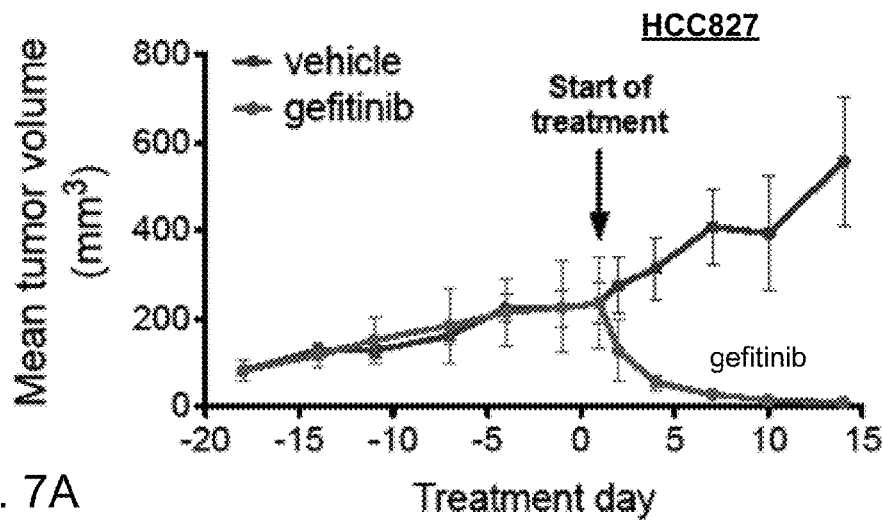
FIGS. 7A-7F are a series of graphs illustrating changes in serum PRDX6 levels for HCC827 and H1975 xenografts treated with either vehicle or gefitinib.
Figure 7B:
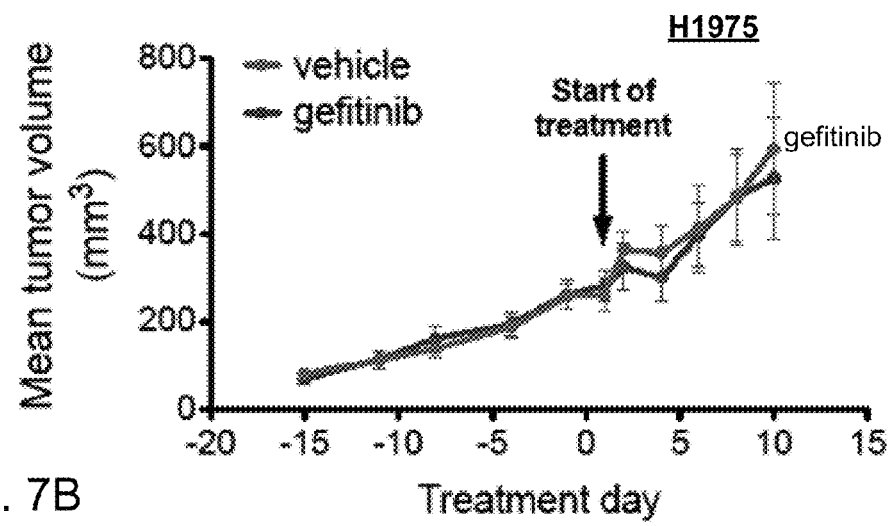

HCC827 xenografts treated with gefitinib showed a highly significant response (FIG. 7A). The difference in tumor volumes between the vehicle treated and gefitinib treated HCC827 xenografts was statistically significant from Day 4 ($P=0.0044$) onwards. H1975 xenografts showed no response to gefitinib (FIG. 7B), and there was no significant difference in tumor volumes between gefitinib and vehicle treated mice in this group at any point during the study.

Figure 7C:
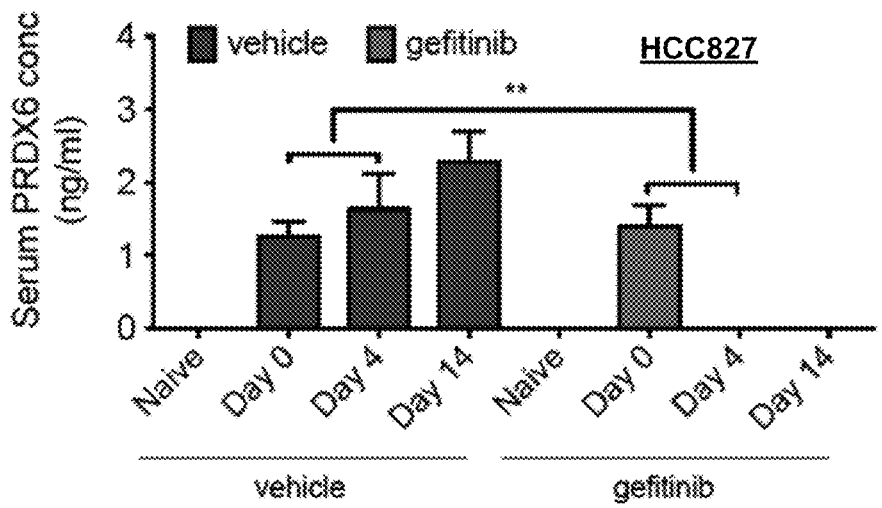

For HCC827 (sensitive) xenografts, mean serum PRDX6 levels increased after treatment with vehicle and decreased dramatically after treatment with gefitinib (FIG. 7C). The difference in the mean change from baseline in serum PRDX6 between vehicle and gefitinib treated animals was statistically significant on both Day 4 ($P=0.0032$) and Day 14 ($P=0.0002$). Furthermore, the difference in the mean change from baseline in serum PRDX6 normalized to tumor volume (FIG. 7E) was significant on Day 4 ($P=0.01$) and Day 14 ($P=0.0303$).

Figure 7D:
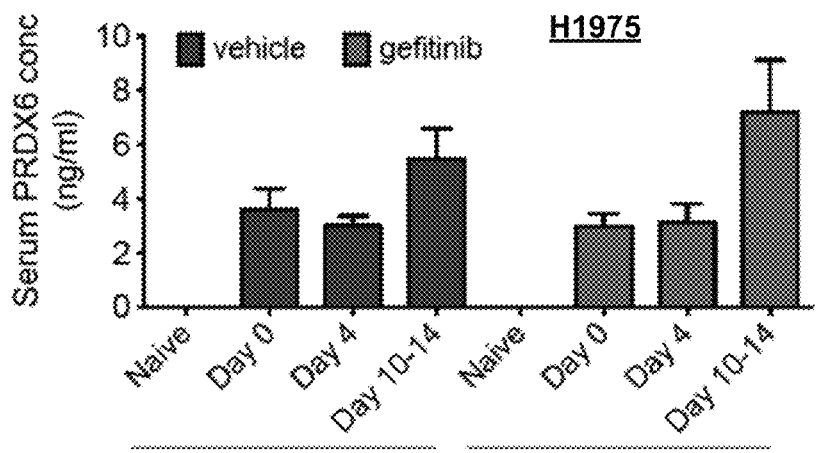
Figure 7E:
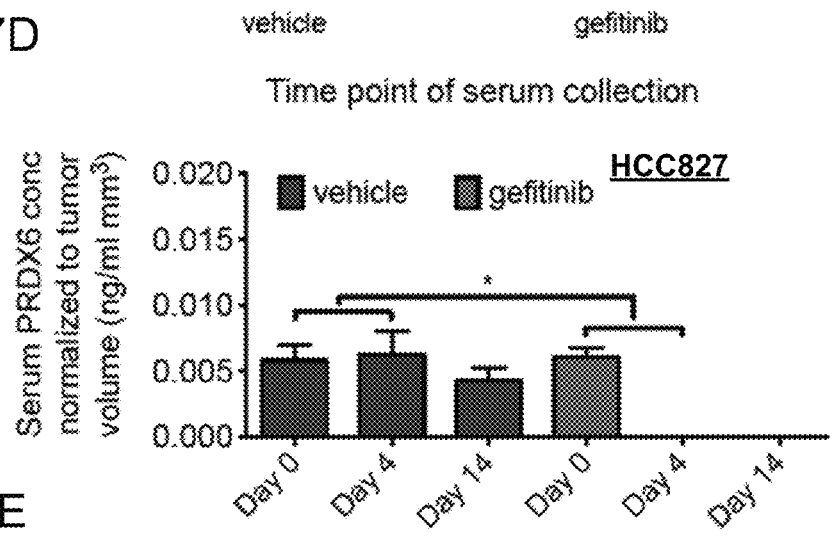
Figure 7F:
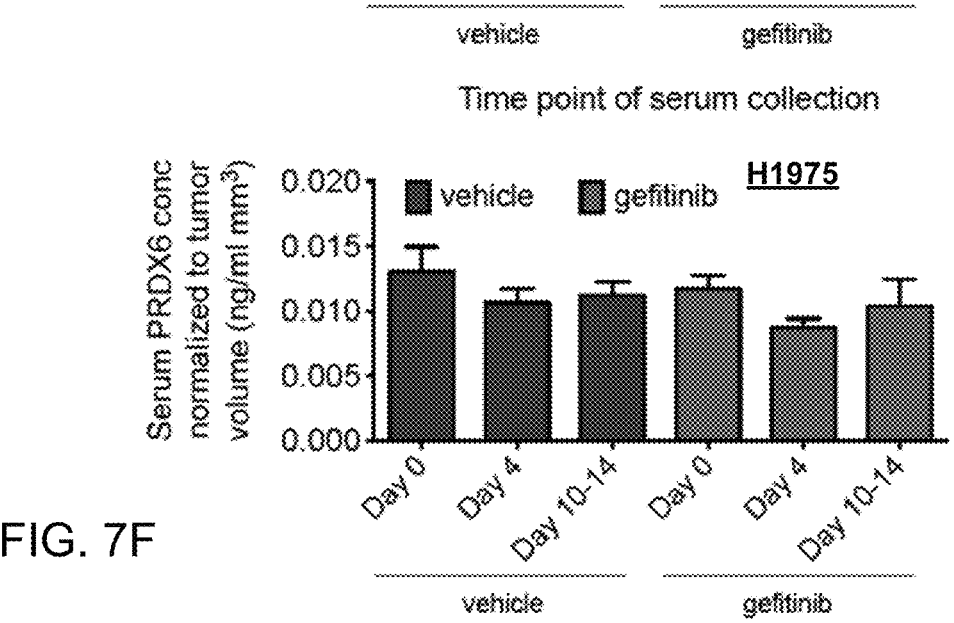

For H1975 (resistant) xenografts, mean serum PRDX6 levels increased after treatment with vehicle or gefitinib (FIG. 7D). The difference in the mean change from baseline in serum PRDX6 between vehicle and gefitinib treated animals was not statistically significant on either Day 4 ($P=0.461$) or Day 10-14 ($P=0.3404$). Furthermore, the difference in the mean change from baseline in serum PRDX6 normalized to tumor volume (FIG. 7F) was not significant on either Day 4 ($P=0.7922$) or Day 10-14 ($P=0.8849$).

Next, PRDX6 levels were assayed in tumor samples collected at the end of the study. Since HCC827 xenografts are highly sensitive to gefitinib it was not possible to derive tumor lysates for these models due to a lack of sufficient tumor tissue. However, no statistically significant difference was found in the tumor lysate PRDX6 levels between the HCC827 vehicle treated xenografts and the H1975 vehicle and gefitinib treated xenografts ($P=0.8876$, one-way ANOVA) (data not shown).

Dynamics of Serum PRDX6 Changes after Gefitinib Therapy

To gain insight into the time course of serum PRDX6 levels following the onset of gefitinib therapy, serum from HCC827 xenografts treated with either gefitinib or vehicle, for which blood samples were collected at multiple early time points following the start of treatment, were analyzed. Specifically, blood samples we collected by submandibular bleed from all mice prior to tumor inoculation and immediately before the start of treatment, and then by cardiac puncture from groups of 5 mice from each treatment arm at 12, 24, 48 and 72 hours after the start of treatment.

Figure 8A:
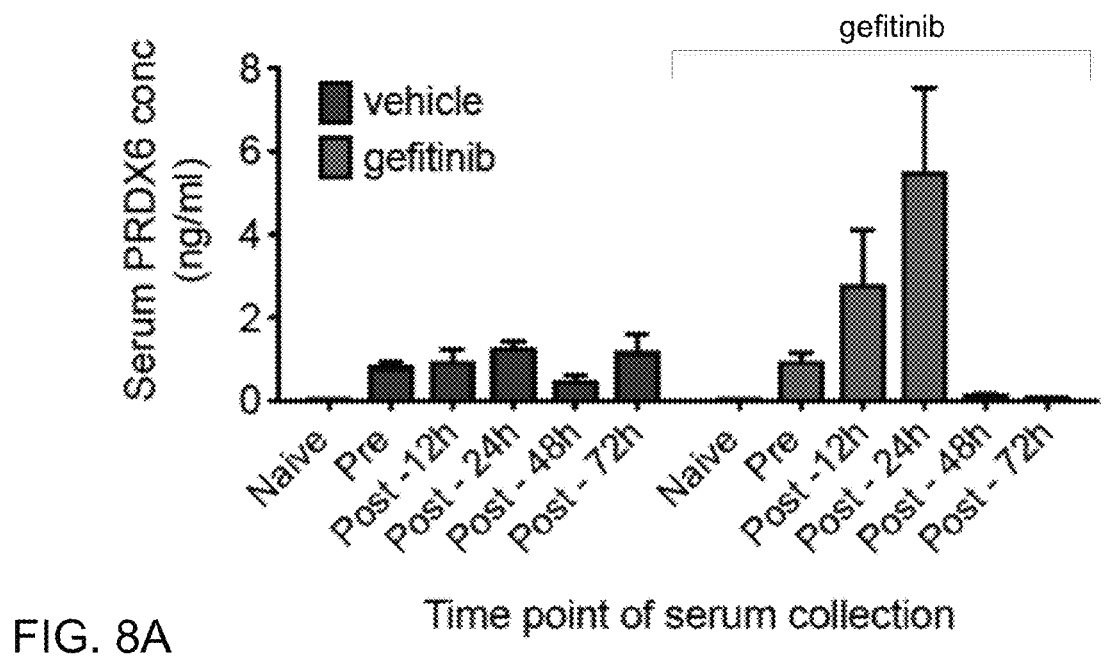
FIGS. 8A-8D illustrate early changes in serum PRDX6 levels for HCC827 xenografts treated with either vehicle or gefitinib.
Figure 8B:
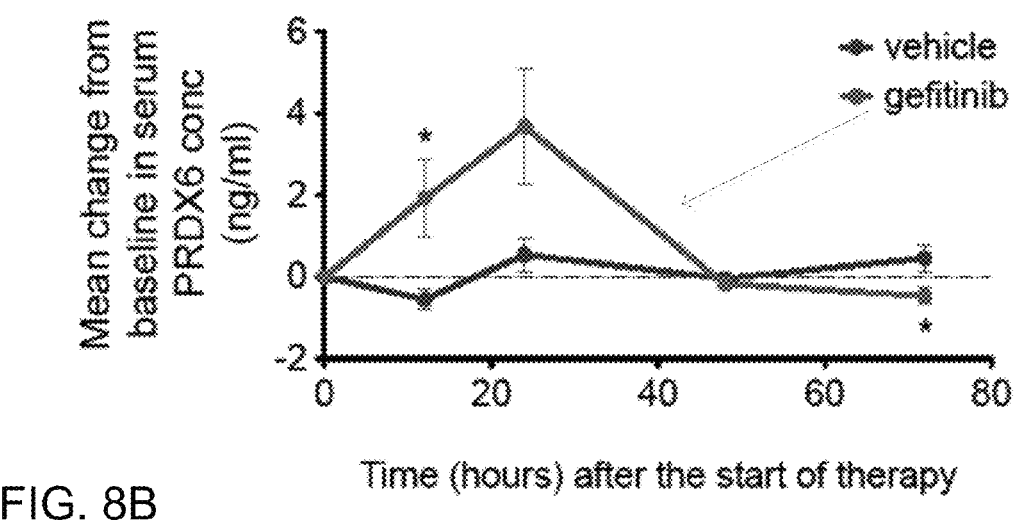
Figure 8C:
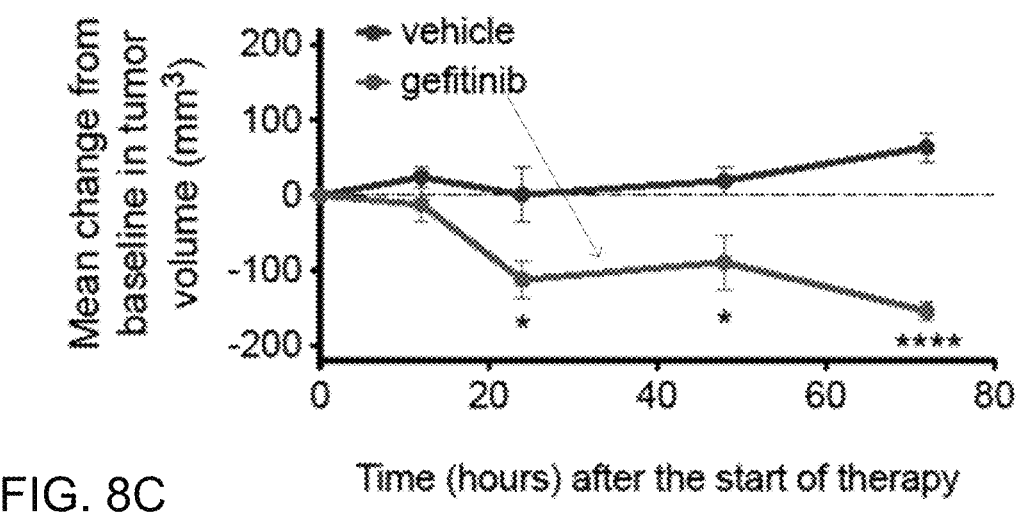
Figure 8D:
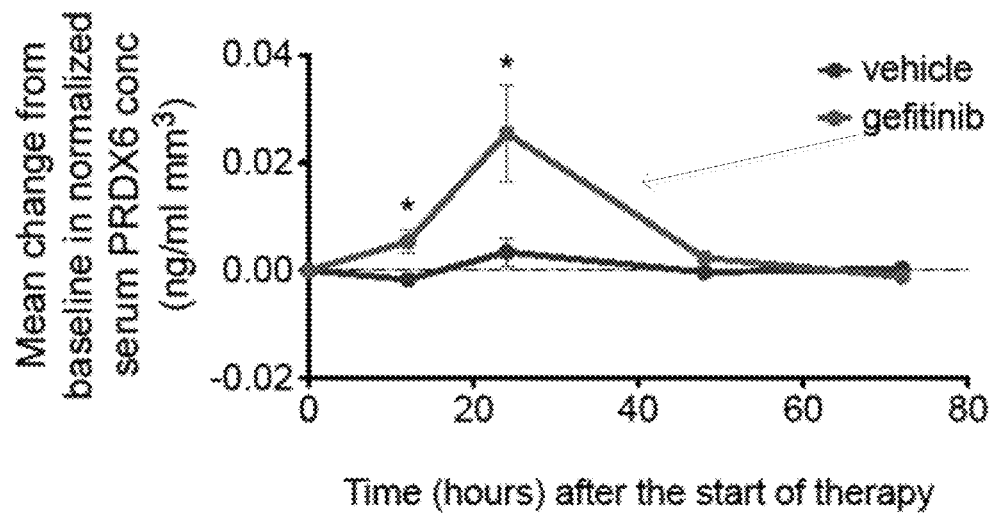

For the gefitinib treated mice, mean serum PRDX6 levels increased markedly after the start of treatment, reaching a maximum concentration at 24 hours post-treatment, before returning to baseline levels at 48 hours and continuing to decrease up to 72 hours post-treatment (FIG. 8A). The increase in mean serum PRDX6 for gefitinib treated animals relative to vehicle treated animals (FIG. 8B) was statistically significant at 12 hours ($P=0.036$) but not at 24 hours ($P=0.0659$). Tumor volumes for gefitinib treated mice decreased relative to those for vehicle treated mice (FIG. 8C) and the mean change from baseline was statistically significant at 24 hours ($P=0.0448$), 48 hours ($P=0.026$), and 72 hours ($P<0.0001$) post-treatment, but not at 12 hours ($P=0.1958$). Mean serum PRDX6 levels normalized to tumor volume were significantly greater for gefitinib treated animals relative to vehicle treated animals (FIG. 8D) at both 12 hours ($P=0.0134$) and 24 hours ($P=0.0438$).

Discussion

Monitoring response to targeted therapies in cancer is presently a major clinical challenge. Oncologists treating patients with targeted agents require effective techniques to assess initial response to therapy (or lack thereof), as well as to detect the potential onset of acquired resistance at a later stage. Therapy monitoring strategies based on the use of blood biomarkers offer a number of compelling advantages over imaging based approaches, including ease of sample collection, absence of ionizing radiation and low cost of sample analysis. Using serial blood sampling from xenograft mouse models together with enzyme-linked immunosorbent assays, the present example reveals a novel blood biomarker of response to anti-EGFR therapy. These results illustrate that changes in serum levels of PRDX6 shortly after gefitinib treatment can differentiate between gefitinib sensitive and gefitinib resistant tumors.

The cell culture studies in this Example showed that for the gefitinib-sensitive cell line HCC827, PRDX6 levels in cell media were significantly increased as early as 12 hours after treatment with gefitinib, compared with the corresponding levels after vehicle treatment. These results were then validated in vivo using HCC827 xenograft models, for which mean serum PRDX6 levels in gefitinib treated animals were significantly higher at 12 hours after the start of treatment compared with their vehicle treated counterparts. Interestingly, serum PRDX6 levels had dropped dramatically by 4 days after the start of gefitinib treatment, and were no longer detectable by ELISA by this point. An issue for translating these findings to the clinic involves determining how the dynamics of serum PRDX6 levels observed in gefitinib sensitive xenograft mouse models relate to those in patients showing a short-term response to anti-EGFR therapy. The "temporal signature" of PRDX6 changes in human NSCLC patients receiving anti-EGFR therapy was examined in Example 3, below.

A key question for a biomarker of therapy response is whether changes in biomarker levels after therapy are predominantly a function of changes in tumor burden, or alternatively a consequence of therapy induced molecular changes that precede a reduction in tumor burden. The results above, for both A431 and HCC827 xenografts, show that after 14 days of gefitinib treatment there is a statistically significant decrease in serum PRDX6 levels normalized to gross tumor volume, compared with vehicle treated animals. Thus, the decrease in serum PRDX6 levels after gefitinib treatment is most likely a result of fundamental changes in oncogenic signaling that directly impact downstream PRDX6 levels. Furthermore, in HCC827 xenograft models, the decrease in tumor volume for gefitinib treated animals compared with vehicle treated animals was significant at 24 hours but not 12 hours post-treatment, despite a significant difference in serum PRDX6 levels at 12 hours post-treatment. Thus, changes in serum PRDX6 precede changes in tumor volume after gefitinib treatment of HCC827 xenografts. This provides further support that serum PRDX6 changes following gefitinib therapy reflect fundamental changes in EGFR signaling and provide key information on early tumor response.

How does inhibition of EGFR signaling lead to subsequent changes in PRDX6 levels? To shed light on this question, a computational network analysis was used in conjunction with a curated knowledge base of protein-protein interactions (MetaCore™, GeneGo) to gain insight into the relationship between EGFR and PRDX6. Network analysis revealed that EGFR indirectly regulates PRDX6 through a variety of transcription factors, including p53[12,13], c-Myc[13-16], c-Jun[17], ESR1[18] and C/EBPbeta[17].

For long-term therapy monitoring to detect the onset of treatment resistance, it is useful to understand how potential mechanisms of acquired resistance may impact biomarker levels. In the case of NSCLC, the most common form of resistance to anti-EGFR therapy is the T790M mutation in the EGFR kinase domain. This mutation, which occurs in approximately 50% of patients[19,20], impairs the ability of EGFR inhibitors to bind to the ATP binding domain of the EGFR kinase[11]. The above results with H1975 xenografts, which harbor the T790M mutation, and are therefore resistant to gefitinib, show that serum PRDX6 levels closely track tumor volume during gefitinib treatment. Hence, it appears that acquired resistance to anti-EGFR therapy via the T790M mutation may lead to a significant and detectable increase in levels of serum PRDX6. However, alternative resistance mechanisms such as MET amplification[21] and mutations in PIK3CA[22], which function independently of the EGFR axis, may not have a significant effect on PRDX6 levels. In order to detect these forms of resistance, monitoring of additional biomarkers that are sensitive to changes in the relevant oncogenic signaling pathways could be useful. The use of multiple blood biomarkers together with multiplexed assays for highly sensitive biomarker quantification[23] may provide an effective strategy to monitor response to a range of targeted therapies, either as single agents or combination therapies.

Materials and Methods

Cell Lines and Reagents:

Human cancer cell lines A431, HCC827, and H1975 were obtained from American Type Culture Collection (ATCC, Manassas, Va.). HCC827 and H1975 cells were grown in RPMI medium 1640 with HEPES buffer and L-glutamine (GIBCO, Invitrogen; Cat. No. 22400-089) supplemented with 1 mM sodium pyruvate (GIBCO, Invitrogen; Cat. No. 11360-070), 10% FBS and 1% penicillin/streptomycin. A431 cells were grown in Dulbecco's Modified Eagle's Medium with high glucose and sodium pyruvate (GIBCO, Invitrogen; Cat. No. 10569-010) supplemented with 10% FBS and 1% penicillin/streptomycin. All cells were grown in standard tissue culture incubators at 37° C. with 95% air/5% $CO_2$ and tested regularly for mycoplasma contamination using the Lonza MycoAlert mycoplasma detection kit (Lonza Ltd, Basel, Switzerland; Cat. No. LT07-418).

Cell Culture Experiments:

A431 and HCC827 cells were cultured in complete media and plated onto 100 mm tissue culture dishes (BD Biosciences, Durham, N.C.) at a density of approximately 1.5 million cells per plate (media volume of 10 ml per plate). For each cell line, 36 plates were seeded in this manner. The cells were allowed to grow to approximately 80% confluence at which point the old media was aspirated, the cell layer carefully washed with PBS, and 10 ml of low serum media (0.1% FBS) supplemented with 10 nM EGF (GIBCO, Invitrogen; Cat. No. PHG0311L) was added to each plate. Half of the plates were then treated with 100 nM gefitinib (Biaffin GmbH & Co. KG; Cat. No. PKI-GFTB-010) dissolved in DMSO, while the other half were treated with the vehicle (0.01% DMSO). Three plates from each treatment group were collected at 0, 4, 8, 12, 24, and 32 hours after the start of treatment. At each time point, the plates were maintained on ice and the cell media was pipetted into a 15 ml falcon tube, centrifuged at 1000 rpm for 5 minutes to pellet any dead cells and cell debris, and the supernatant was then aliquoted and stored at −80° C. The culture plates were carefully washed with ice cold PBS whilst taking care not to disturb the cell layer, sealed with Sarran™ wrap and transferred to −80° C. for storage. Once the samples for all time points had been collected, the cell media aliquots and cell culture plates were processed together for subsequent ELISA analysis.

Cell Media and Lysate Processing:

Cell media was first centrifuged for 5 minutes at 1000 rpm and the supernatant collected in order to remove dead cells. 10 ml of cell media was then concentrated to 600 µl using Amicon Ultra Centrifugal (UltraCel®) Units with a molecular weight cut-off of 10 kDa (Millipore, Billerica, Mass.). Briefly, 4 ml aliquots of cell media were loaded onto the UltraCel® units and centrifuged at 3000 rpm for 10-15 minutes at 4° C. using an Eppendorf 5810R centrifuge. This procedure was repeated until sample volumes were reduced to 600 µl.

For cell lysis, frozen culture plates were thawed on ice and treated with 750 µl of ice-cold cell lysis buffer. Lysis buffer consisted of 10×RIPA buffer (Cell Signaling Technology, Danvers, Mass.; Cat. No. 9806S) diluted to 1× concentration in $ddH_2O$, and supplemented with protease inhibitor (Thermo Fisher Scientific, Rockford, Ill.; Cat. No. 78430), phosphatase inhibitor (Thermo Fisher Scientific; Cat. No. 78420) and EDTA (Thermo Fisher Scientific; Cat. No. 1860851). Two minutes after the addition of the lysis buffer, the plates were scraped using cell scrapers and the contents transferred into standard 1.5 ml Eppendorf tubes using a micropipette. During the entire procedure, all culture plates were maintained on ice. The lysates were then sonicated under ice-cold conditions in a Branson 2510 sonicator (Emerson Industrial Automation, Danbury, Conn.) using six bursts of ten seconds each, and then maintained on ice for a further 10 minutes. Following sonication, the samples were centrifuged for 10 minutes at 12,800 rpm at 4° C. using a refrigerated bench top Eppendorf 5417R ultracentrifuge. The supernatant was then collected and used for subsequent ELISA (see below) and total protein analysis.

Total protein concentrations for media and lysates were measured using Pierce BCA Protein Assay kits (Thermo Fisher Scientific; Cat. No. 23225).

Xenograft Studies:

All animal studies were approved by Stanford University Administrative Panel on Laboratory Animal Care. For all tumor inoculations, cells were suspended in an equal mixture of media and growth-factor reduced matrigel (BD Biosciences, Bedford, Mass.; Cat. No. 356231) with 100 µl of cell suspension used per inoculation. Tumor dimensions were measured every 2-3 days using digital calipers and converted to estimates of tumor volume according to the formula: $V=4/3\pi a\, b^2$, where a and b are the lengths of the major and minor axes of the tumor, respectively. Following randomization into treatment groups, mice were dosed daily by oral gavage with either 100 µl drug including 50 mg/kg gefitinib (LC Laboratories, Woburn, Mass.; Cat. No. G4408) suspended in $H_2O$ with 0.5% Tween-80, or 100 µl vehicle consisting of $H_2O$ with 0.5% Tween-80.

For the A431 xenograft study, twenty-five 8 to 10 week old female nude athymic mice (Charles River Laboratories, Wilmington, Mass.) were inoculated in the right flank above the hind limb with A431 cells. The A431 cell line used for the xenograft study was obtained as a gift from Dr. Anjali Jain at Cedars-Sinai Medical Center and established as previously described[24]. Once the average tumor volume reached approximately 400 $mm^3$, the mice were randomized into treatment and control groups including ten mice per group. Blood samples were collected from all mice prior to tumor inoculation, immediately before the start of treatment, and at the end of the study (Day 15). Mice were sacrificed 14 days after the start of treatment, or at an earlier time point if the tumor size (along any dimension) exceeded 20 mm, weight loss exceeded more than 10% of body weight, or animals exhibited signs of distress. For the HCC827/H1975 study, thirty 8 to 10 week old female athymic female mice were inoculated in the thymus with 3-4 million cells, with half the mice inoculated with HCC827 cells and half with H1975 cells. Once the average tumor volume reached approximately 240 $mm^3$, each cohort of mice was randomized into treatment and control groups including six mice per group. Blood samples were collected from all mice prior to tumor inoculation, immediately before the start of treatment, after the start of treatment (Day 4) and at the time of sacrifice (Day 10-15). Mice were sacrificed at the end of the study (Day 15), or earlier if the tumor size along any dimension exceeded 15 mm, weight loss exceeded more than 10% of body weight, or animals exhibited signs of distress.

Blood Sampling:

For all xenograft studies, blood samples were collected prior to the time of sacrifice by submandibular bleed from the cheek using 5 mm Goldenrod Animal Lancets (Medipoint Inc., Mineola, N.Y.). At the time of sacrifice, a final sample was collected by cardiac puncture. Blood samples were collected in 1.1 ml screw cap micro tubes containing a serum gel clotting activator (Sarstedt Inc., Newton, N.C.; Cat. No. 41.1378.005). Immediately following collection, each tube was tapped several times and then inverted ten times to ensure adequate mixing of the blood, before being allowed to clot for one hour at 20° C. The collection tubes were then centrifuged at 10,000 g for 5 minutes at 4° C. Finally, the separated serum was transferred in batches of 50 µl to labeled Eppendorf tubes using a micropipette and stored at −80° C.

Statistical Analysis:

Statistical analysis was performed using GraphPad Prism (GraphPad Software, La Jolla, Calif.). For all statistical tests, a two-tailed unpaired Student's t test was used to determine the significance of changes between vehicle and gefitinib treated groups at specific time points. To assess the significance of changes in serum PRDX6 levels for xenograft studies, PRDX6 changes from baseline after gefitinib treatment were compared with the corresponding changes from baseline after vehicle treatment[25]. To assess the correlation between tumor volume and PRDX6 levels, Pearson's $R^2$ statistic was used. For all statistical tests a P value<0.05 was considered to be significant.

Computational Network Analysis:

Network Analysis was Performed Using MetaCore™ (GeneGo, Thomson Reuters, Carlsbad, Calif.). Dijkstra's shortest path algorithm was used to find all possible connections in the knowledge base linking EGFR and PRDX6 in a maximum of two steps.

Enzyme-Linked Immunosorbent Assays:

ELISAs were performed as sandwich assays using paired capture and detection antibodies together with an appropriate antigen standard. Maxisorp F96 96-well plates (Nunc, Thermo Fisher Scientific; Cat. No. 442404) were coated with 100 µl/well of diluted capture antibody in PBS (GIBCO, Invitrogen; Cat. No. 10010-023) to a final concentration of 100 ng/ml (unless otherwise specified—see below), and incubated overnight at room temperature. Each plate was washed three times with 300 ul of 1× wash buffer (KPL; Cat. No. 50-63-04) using a BioTek EL408 plate washer, and blocked at room temperature for 2 hours with 300 µl/well of either 1% BSA (Sigma; Cat. No. A4503-50G) or 5% milk. Protein standards were diluted with 1% BSA for an 8 point standard curve, while samples were diluted to a suitable concentration within the dynamic range of the ELISA. Samples and standards were allowed to warm to room temperature, and 100 ul of each standard or sample was added to the plate in duplicates. The plate was then sealed with an adhesive film and incubated for 2 hours at room temperature.

Following standard/sample incubation, the plate was washed and incubated for 2 hours at room temperature with 100 µl per well of detection antibody at a concentration of 100 ng/ml (unless otherwise specified). After washing, the plate was incubated with 100 µl per well of an appropriate HRP conjugated antibody diluted in reagent diluent according to the specifications, and incubated for 30 minutes at room temperature. This was followed by 100 ul of TMB 2 Component Microwell Peroxidase Substrate (KPL; Cat. No. 50-76-00) at room temperature, with the plate maintained in the dark for 20 minutes. The reaction was stopped by addition of 50 ul of stop solution (KPL; Cat. No. 50-63-04) and read on a TECAN Infinite M1000 plate reader at optical densities of 450 nm (measurement wavelength) and 570 nm (reference wavelength). The 570 nm reference reading was then subtracted from the 450 nm measurement reading to give the final optical absorption values for the plate.

For each ELISA plate, a 4 parameter sigmoidal curve was fit to the log antigen concentration vs optical absorption data for the standards by least squares using GraphPad Prism 5 (GraphPad Software Inc., La Jolla, Calif.). The resulting interpolation function was then used to back calculate the biomarker concentration levels for all the samples on the plate.

ELISA Antibody Pairs:

PRDX6 and phospho-EGFR ELISAs were based on the following antibody/antigen combinations:

| Protein | Antibody/Antigen | Vendor | Cat. No. | Conc. (ng/ml) | Block with |
|---|---|---|---|---|---|
| PRDX6 | Capture Ab | Santa Cruz | sc-59671 | 1000 | 1% BSA |
| | Antigen | AbCAM | ab73681 | 25 | |
| | Detection Ab | AbCAM | ab73350 | 1000 | |
| p-EGFR (Y1068) | Capture Ab | R&D Systems | 842428 | 8000 | 1% BSA |
| | Antigen | R&D Systems | 842430 | 20 | |
| | Detection Ab | R&D Systems | 842429 | 1:100 | |

Figure 9A:
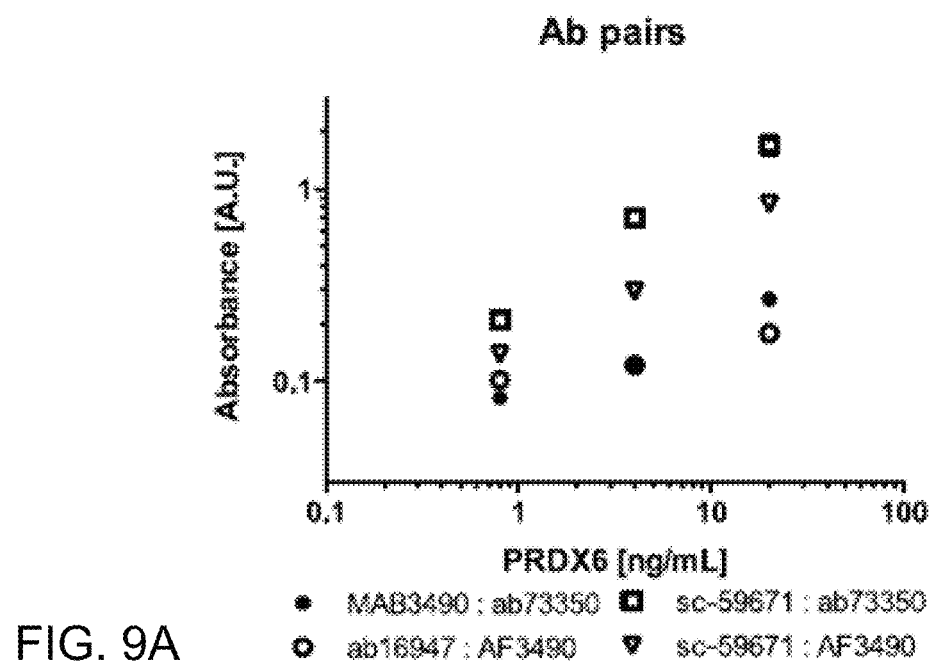
Figure 9B:
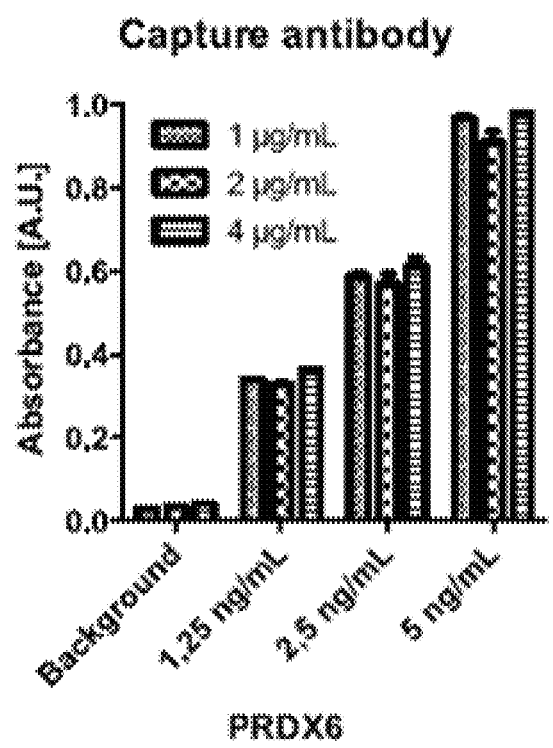

Development of PRDX6 ELISA:

Commercially available anti-PRDX6 antibodies (see table below) were initially tested in a direct ELISA with PRDX6 coated at 50, 10, 2, and 0.4 ng/well in a 96-well plate. Antibodies that were found to bind to PRDX6 in a concentration dependent manner were subsequently tested in a sandwich configuration to find suitable antibody pairs. Of the tested configurations, the pair sc-59671:ab73350 yielded the highest signal while maintaining a low background reading (FIG. 9A). The optimal concentrations of capture and detection antibodies were evaluated in a grid experiment. A concentration of 1 µg/mL for both the capture and detection antibody showed the best performance (FIG. 9B-C). The influence of sample matrix was tested with a 4-point dilution of PRDX6 in PBS with 50% mouse serum or PBS with 1% BSA. The readings were almost identical (see FIG. 9D) confirming the ability to measure PRDX6 in the presence of 50% serum. Two 8-point standard curves were performed independently of each other on different days to test the robustness of the PRDX6 ELISA. The ELISA showed a high degree of repeatability and sensitivity below 0.4 ng/mL (FIG. 9E).

PRDX6 Antibodies:

The following antibodies were tested in the development of the PRDX6 ELISA:

| Antibody | Vendor | Cat. No. |
|---|---|---|
| Capture Ab | R&D Systems | MAB3490 |
| Capture Ab | AbCAM | ab16946 |
| Capture Ab | AbCAM | ab16947 |
| Capture Ab | Santa Cruz | sc-59671 |
| Detection Ab | R&D Systems | AF3490 |
| Detection Ab | AbCAM | ab73350 |
| Detection Ab | Santa Cruz | sc-134478 |

Tumor Processing:

Following tumor resection, any remaining connective tissue was removed using scissors and the resected tumors were added to a 10 cm plate containing approximately 10 ml of serum-free and phenol-free RPMI 1640. Using two razor blades, tumor chunks were cut into pieces (~1-2 mm×1-2 mm) that were sufficiently small to be pipetted with a 10 mL pipette. Tumor pieces were transferred to a 50 ml tube and centrifuged at 1000 rpm at room temperature for 5 minutes. Following centrifugation, the supernatant was aspirated using a glass pipette, and digestion solution added to the pellet. Digestion solution was prepared by adding 15 ml of undiluted 0.05% trypsin-EDTA (1×) to a 50 ml tube, followed by 3000 units of Collagenase IV (Invitrogen; Cat. No. 17104-019) and 12 ml of serum-free media. Tumor pieces were digested in a hybridization oven at 37 C for 3.5 hours. Following digestion, an equal volume of media containing 10% serum was added to stop the digestion. The solution was pipetted repeatedly to break up remaining clumps as much as possible and then filtered through a wire mesh into a 10 cm plate. The remaining tumor pieces were ground gently with a cell scraper on a separate 10 cm plate to break up the softer pieces and release more cells. The resulting suspension was then filtered through the wire mesh with fresh media. The final filtered suspension was centrifuged at 1000 rpm at room temperature for 5 minutes, resuspended in 90% serum and 10% DMSO, transferred to 1 ml cryovials, frozen down at −80° C. using an isopropanol containing freezer box, and finally transferred to liquid nitrogen for long term storage.

References for Example 2

The following references are incorporated herein by reference in pertinent part:
1. Hanash, S. M., Baik, C. S. & Kallioniemi, O. Emerging molecular biomarkers—blood-based strategies to detect and monitor cancer. *Nature reviews. Clinical oncology* 8, 142-50 (2011).
2. Pao, W. & Chmielecki, J. Rational, biologically based treatment of EGFR-mutant non-small-cell lung cancer. *Nature reviews. Cancer* 10, 760-774 (2010).
3. Rosell, R., et al. Screening for epidermal growth factor receptor mutations in lung cancer. *N Engl J Med* 361, 958-967 (2009).
4. Maemondo, M., et al. Gefitinib or chemotherapy for non-small-cell lung cancer with mutated EGFR. *N Engl J Med* 362, 2380-2388 (2010).
5. Mok, T. S., et al. Gefitinib or carboplatin-paclitaxel in pulmonary adenocarcinoma. *N Engl J Med* 361, 947-957 (2009).
6. Eisenhauer, E. A., et al. New response evaluation criteria in solid tumours: revised RECIST guideline (version 1.1). *Eur J Cancer* 45, 228-247 (2009).
7. Kani, K., et al. Quantitative proteomic profiling identifies protein correlates to EGFR kinase inhibition. *Molecular cancer therapeutics* 11, 1071-1081 (2012).
8. Wakeling, A. E., et al. ZD1839 (Iressa): an orally active inhibitor of epidermal growth factor signaling with potential for cancer therapy. *Cancer research* 62, 5749-5754 (2002).
9. Amann, J., et al. Aberrant epidermal growth factor receptor signaling and enhanced sensitivity to EGFR inhibitors in lung cancer. *Cancer research* 65, 226-235 (2005).
10. Xu, Y. H., Richert, N., Ito, S., Merlino, G. T. & Pastan, I. Characterization of epidermal growth factor receptor gene expression in malignant and normal human cell lines. *Proceedings of the National Academy of Sciences of the United States of America* 81, 7308-7312 (1984).
11. Yun, C. H., et al. The T790M mutation in EGFR kinase causes drug resistance by increasing the affinity for ATP. *Proceedings of the National Academy of Sciences of the United States of America* 105, 2070-2075 (2008).
12. Albers, M., et al. Automated yeast two-hybrid screening for nuclear receptor-interacting proteins. *Molecular & cellular proteomics: MCP* 4, 205-213 (2005).
13. Beck, H. C., et al. Proteomic profiling of human colon cancer cells treated with the histone deacetylase inhibitor belinostat. *Electrophoresis* 31, 2714-2721 (2010).
14. Anderson, P. D., et al. Nkx3.1 and Myc crossregulate shared target genes in mouse and human prostate tumorigenesis. *The Journal of clinical investigation* 122, 1907-1919 (2012).
15. Dannenberg, J. H., et al. mSin3A corepressor regulates diverse transcriptional networks governing normal and neoplastic growth and survival. *Genes & development* 19, 1581-1595 (2005).

16. Kidder, B. L., Yang, J. & Palmer, S. Stat3 and c-Myc genome-wide promoter occupancy in embryonic stem cells. *PloS one* 3, e3932 (2008).
17. Lee, T. H., et al. Characterization of the murine gene encoding 1-Cys peroxiredoxin and identification of highly homologous genes. *Gene* 234, 337-344 (1999).
18. Gao, H., Falt, S., Sandelin, A., Gustafsson, J. A. & Dahlman-Wright, K. Genome-wide identification of estrogen receptor alpha-binding sites in mouse liver. *Molecular endocrinology* (Baltimore, Md.) 22, 10-12 (2008).
19. Kobayashi, S., et al. EGFR mutation and resistance of non-small-cell lung cancer to gefitinib. *N Engl J Med* 352, 786-792 (2005).
20. Pao, W., et al. Acquired resistance of lung adenocarcinomas to gefitinib or erlotinib is associated with a second mutation in the EGFR kinase domain. *PLoS medicine* 2, e73 (2005).
21. Engelman, J. A., et al. MET amplification leads to gefitinib resistance in lung cancer by activating ERBB3 signaling. *Science* 316, 1039-1043 (2007).
22. Sequist, L. V., et al. Genotypic and histological evolution of lung cancers acquiring resistance to EGFR inhibitors. *Sci Transl Med* 3, 75ra26 (2011).
23. Gaster, R. S., et al. Matrix-insensitive protein assays push the limits of biosensors in medicine. *Nat Med* 15, 1327-1332 (2009).
24. Fang, Q., et al. Impact of protein stability, cellular localization, and abundance on proteomic detection of tumor-derived proteins in plasma. *PloS one* 6, e23090 (2011).
25. Bland, J. M. & Altman, D. G. Comparisons within randomised groups can be very misleading. *British Medical Journal* 342(2011).

Example 3: Human Preclincal and Clinical Data Showing Human PRDX6 Profile with Tarceva® (Erlotinib)

FIG. 8, from Example 2, above, illustrates the temporal profile of PRDX6 "shedding"[1] (driven by Iressa® treatment) into the circulation of nude mice carrying Iressa-sensitive tumor xenografts. As used herein, "shedding" refers to the extrusion of a candidate biomarker into the media (cell culture) or into the circulation (preclinical or clinical) as a response to physiological or pharmacological challenge. The cause of shedding stems from release of biomarker either through death and lysis of tissues or cells or from a change in intrinsic biomarker expression as a result of therapy. As seen from FIG. 4D, the murine model's response to Iressa® is characterized by an initial spurt of PRDX6 into the circulation. This extrusion seems to peak within 24 hours and is followed by a decline afterwards in measured circulating PRDX6 concentration. The peak occurred before a significant loss in tumor load (i.e. both total number and total mass of cancers within in the host). Subsequent loss of PRDX6 content then parallels shrinkage of tumor. Additional investigations showed that in non-treated xenograft models, circulating PRDX6 content was significantly (at least P<0.01) correlated to tumor size for several types of NSCLC[2] xenografts. PRDX6 levels did not change with respect to Iressa® treatment for models carrying Iressa-resistant NSCLC xenografts thus suggesting that non-responsiveness in PRDX6 shedding with therapy may be used to uncover resistance to therapy.

Figure 10A:
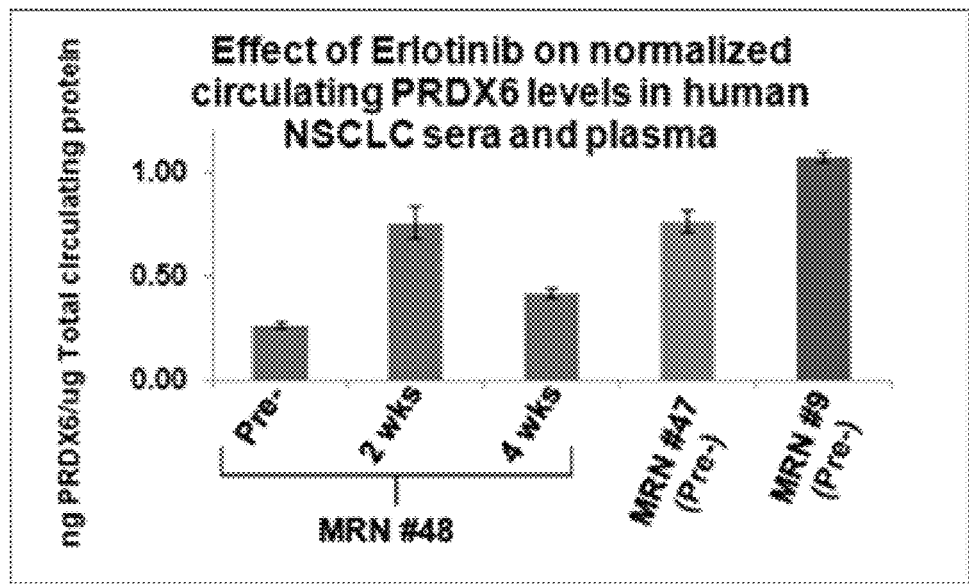
FIG. 10A illustrates an embodiments of a multi-patient PRDX 6 expression profile showing pre-treatment PRDX6 levels for 3 patients and 2-week and 4-week post treatment levels for patient MRN #48.
Figure 10B:
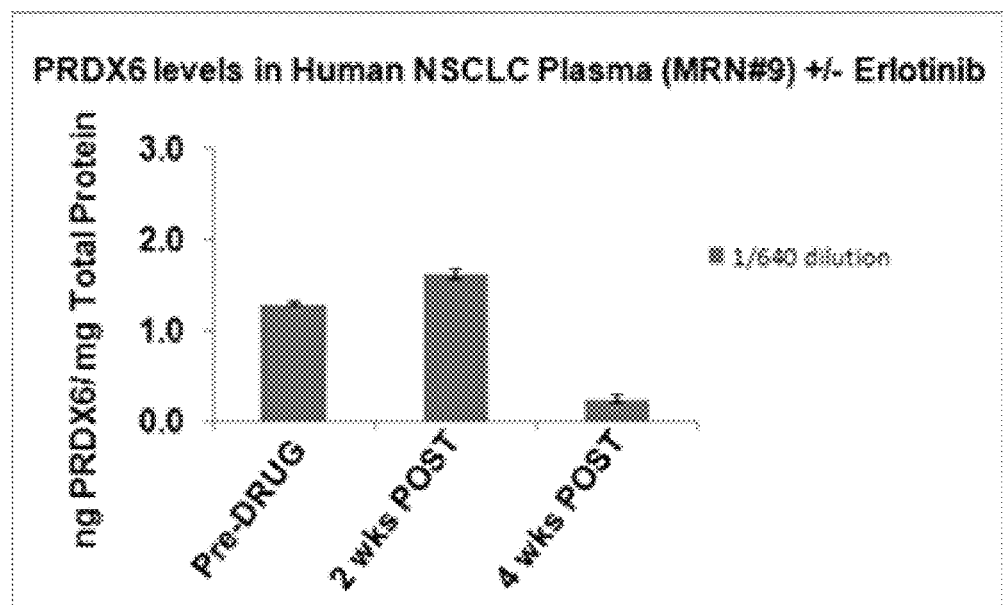
FIG. 10B illustrates an embodiments of a PRDX6 Expression Profile for patient MRN #9, showing PRDX6 protein levels in plasma at pre-treatment, 2 weeks and 4 weeks after initiation of treatment with Erlotinib.
Figure 10C:
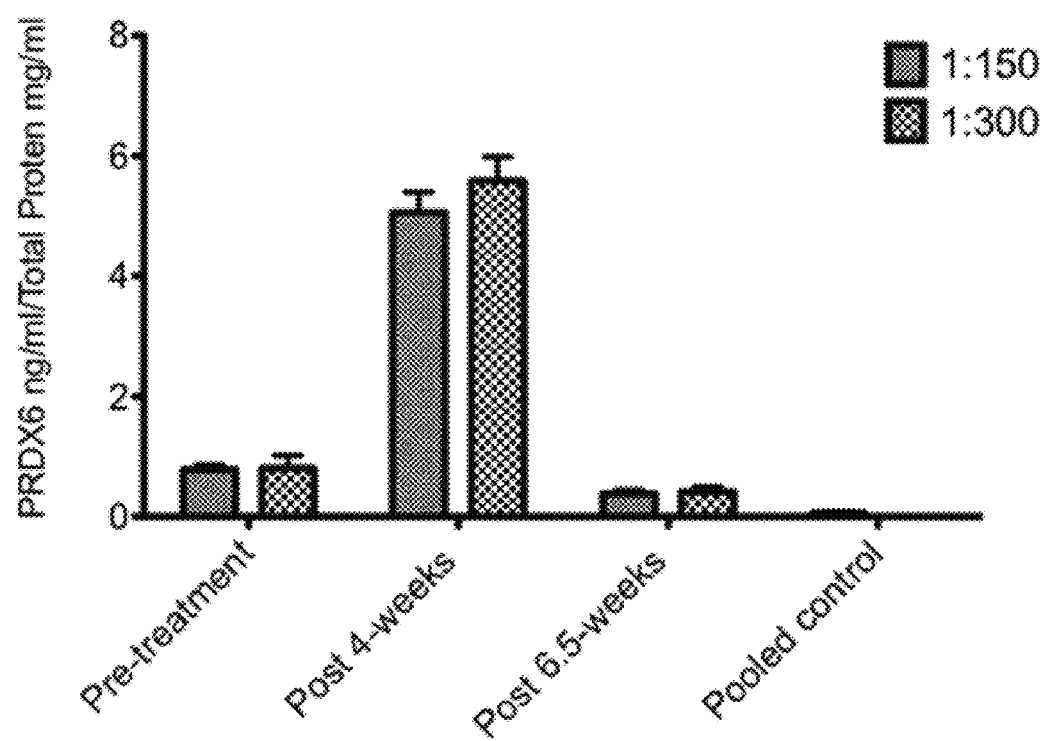
FIG. 10C illustrates an embodiment of a PRDX6 expression profile for patient #91, showing pre-treatment, 4-week, and 6.5-week post-treatment levels compared to pooled control PRDX6 levels.

To validate if this temporal profile is replicated in a clinical setting, the plasma and/or sera from human NSCLC patients was studied before and after Tarceva® (erlotinib) treatment. The results are summarized in Table II. A multi-patient PRDX6 expression profile comparing pre- and post PRDX6 expression levels for patient MRN#48 with pre-treatment levels of patients #47 and #9 is shown in FIG. 10A. Patient MRN#48 had no visible tumor (all having been removed) and was a former Stage IIIa NSLC patient. Serum samples from MRN #48 (FIG. 10A) were taken before and after treatment with Tarceva®. PRDX6 expression profiles (before and after treatment) for individual patients MRN #9 and #91 are shown in FIGS. 10B and 10C, respectively. Patient MRN#9 (FIG. 10B) had tumors present on treatment, was diagnosed with Stage IV cancer including multiple tumors and metastatic lesions. Plasma samples were obtained before treatment, and at 2 weeks and 4 weeks post initiation of treatment. For NSCLC patient #91 (FIG. 10C) samples were taken before treatment and at 4 weeks and 6.5 weeks after beginning treatment with Tarceva®. Tarceva® is a tyrosine-kinase inhibitor that is chemically related to Iressa®. Biomarker profiles by NSCLC cells treated with Tarceva® were the same as Iressa® treated NSCLC cells (data not shown). Pilot data from Table II and FIGS. 10A-10C showed that for at least three patients, a positive response to Tarceva® was characterized by an initial rise in circulating PRDX6 (2-4 weeks post-therapy) followed by a decline in PRDX6 levels by 8 weeks post-therapy. The preliminary clinical findings appear consistent with the results of the preclinical studies.

Figure 11A:
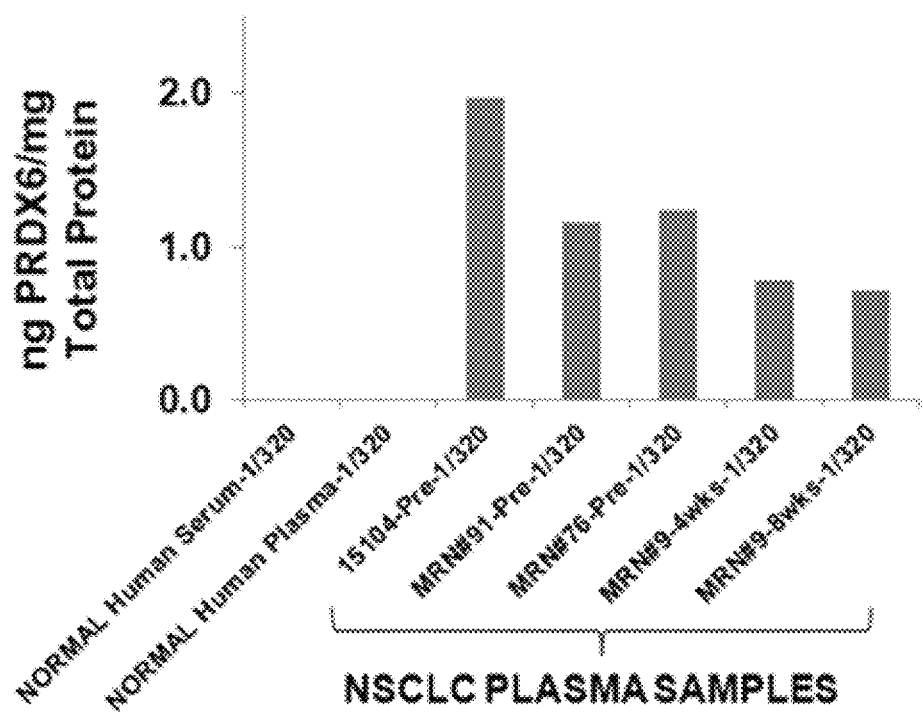
FIG. 11A is a graph comparing PRDX6 levels in various human samples at different time periods.
Figure 11B:
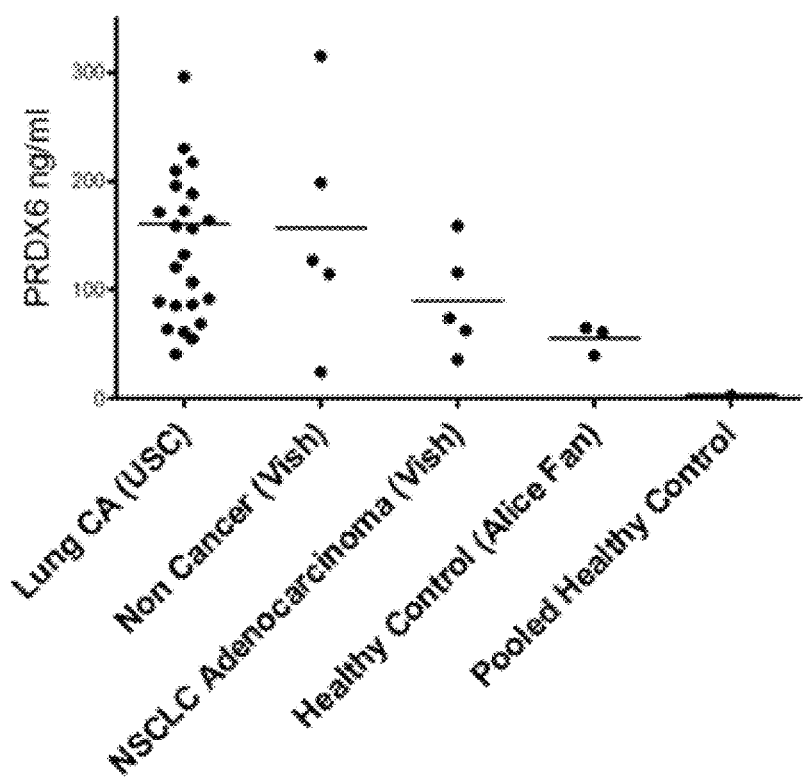
FIG. 11B compares PRDX6 levels in samples from subjects with different cancers or control groups.

Additionally, FIGS. 11A and B illustrate PRDX6 levels in various human samples and correlation with cancer type and/or treatment time. As shown in FIG. 11A, PRDX6 levels in plasma and serum of a normal (control) human subject are distinguishable from plasma samples from subjects with NSCLC. Also, FIG. 11A correlates with the findings in the mouse studies of Example 2, showing that PRDX6 levels dropped over treatment time for some of the NSCLC patients. FIG. 11B illustrates PRDX6 levels in samples taken from subjects with different stages of NSCLC, showing that, in general, PRDX6 expression progresses (i.e., is higher) in patients with progression of the stage of NSCLC.

Thus, these data demonstrate that temporal expression profile of PRDX6 to therapy is consistent from the murine model to humans. The timing (<24 hours for cells, ≤4 weeks for NSCLC patients), amplitude, extent and duration of PRX6 shedding presages the effectiveness of Iressa® therapy and therefore the thoroughness of cancer killing. In addition, non-responsiveness to therapy could indicate, quickly (<24 hours post-therapy for murine models, before 4 weeks in patients), if the resident cancers display or will soon acquire resistance to therapy. We believe that utilization of PRDX6 (as well as other candidates) as biomarkers for therapy monitoring will significantly alter and streamline clinical standards of care. It can be used to predict therapeutic effectiveness as well as to modulate therapeutic strategy in a manner superior to present expensive, time-consuming and excessively interventional (CT/PET/MRI) or non-quantitative (clinical judgments and observation by clinician) practices. There is also the possibility that PRDX6 may be a therapy-response biomarker unique to Iressa® or Tyrosine Kinase Inhibitor-type therapies as effective pacli-taxel treatment on NSCLC failed to elicit a similar shedding of PRDX6. Going forward, we believe that PRDX6 can be fitted into a future panel of clinical biomarkers that could effectively and quickly monitor and help modulate the effectiveness of specific anti-cancer therapies.

TABLE II

Summary of PRDX6 levels in Circulation of NSCLC Patients

| MRN | Pre-Tarceva | Post-Tarceva (2 wks.) | Post-Tarceva (3.5 to 4 wks.) | Post-Tarceva (6.5-8 wks.) |
|---|---|---|---|---|
| 47 | 0.77 +/− 0.05 | X | X | X |
| 48 | 0.27 +/− 0.01 | 0.76 +/− 0.08 | 0.42 +/− 0.02 | X |
| 9 | 1.07 +/− 0.03 | 1.63 +/− 0.05 | 0.33 +/− 0.11 | 0.45 +/− 0.05 |
| 72 | ND | X | X | X |
| 76 | 1.15 +/− 0.01 | X | ND (3.5 wks.) | X |
| 80 | 1.97 +/− 0.02 | X | X | X |
| 91 | 0.65 +/− 0.09 | X | 5.0 +/− 0.3 | 0.46 +/− 0.18 |
| 104 | ND | | | |

X - Sample not received;
ND - Sample present but measurement not done yet;
MRN - Medical Record Number of Patient;
Data expressed as ng PRDX6/Total Protein in circulation Example 4

Correlation of 3 Shed Biomarkers with $IC_{50}$ to Iressa®

The relationship between shedding of biomarkers into the media from several lines of human non-small cell lung cancer (NSCLC) (as a result of challenge by Iressa®) to their sensitivities with Iressa® (gefitinib) was investigated (FIGS. 12A-12F). Cell line sensitivity to Iressa® is best characterized by experimentally-determined $IC_{50}$ values (the concentration of Iressa® that causes half maximal killing of cancer cell line within 24 hours). The table below gives a listing of the cell lines being tested with their corresponding $IC_{50}$ to Iressa®.

$IC_{50}$ to Irressa of Various NSCLC Cell Lines

| NSCLC cell line | $IC_{50}$ to Iressa |
|---|---|
| H3255 | 15 nM |
| HCC827 | 5-100 nm |
| H1650 | 1000 nM |
| A431 | 10-15 μM |
| H1975 | 18-24 μM |
| H460 | 10-13 μM |

Figure 12A:
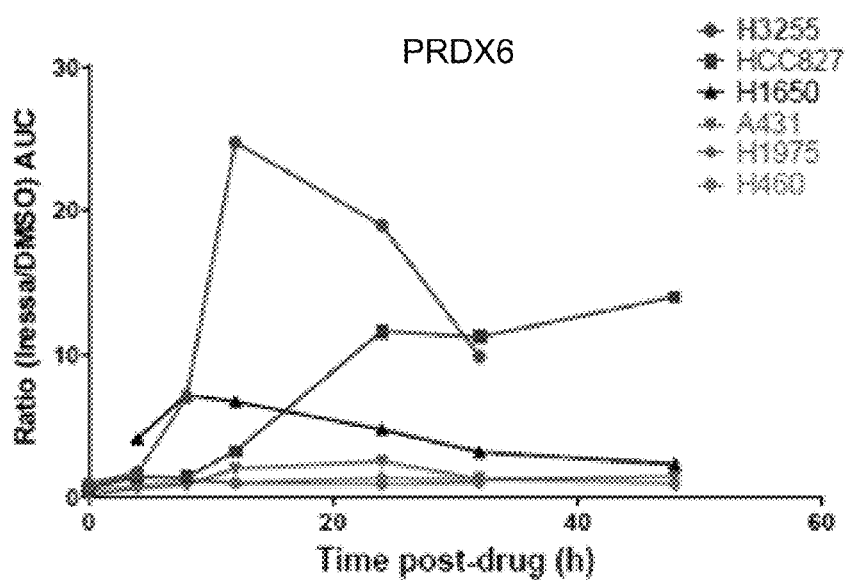
FIGS. 12A-12F illustrate the correlation of shedding of biomarkers (PRDX6, EpCAM, and cMET) by different lines of NSCLC with their $IC_{50}$ to Iressa®.
Figure 12B:
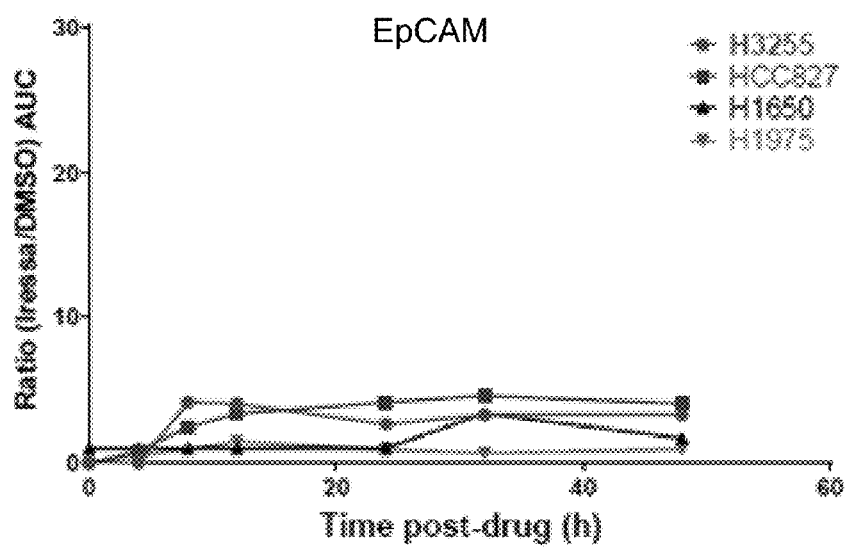
Figure 12C:
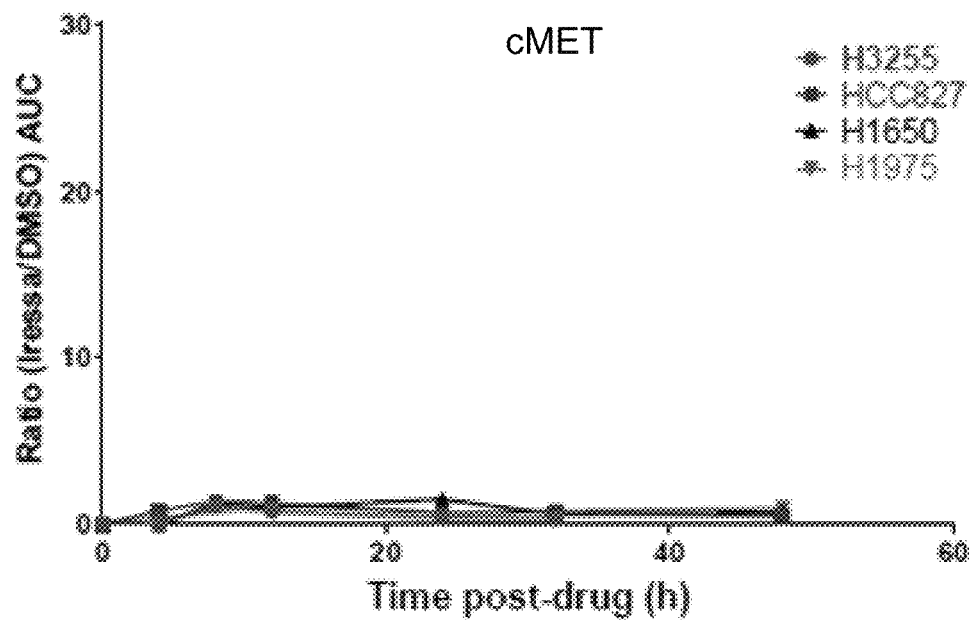
Figure 12D:
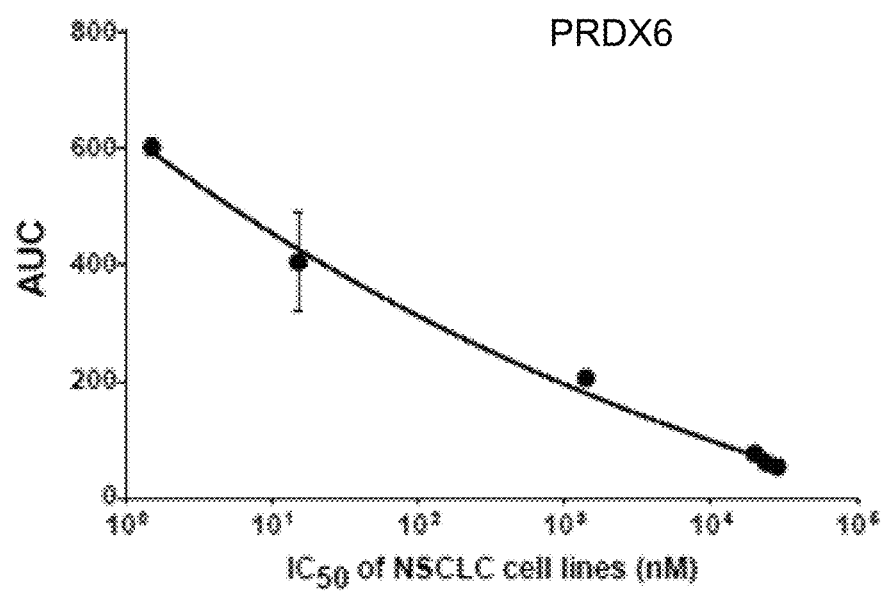
Figure 12E:
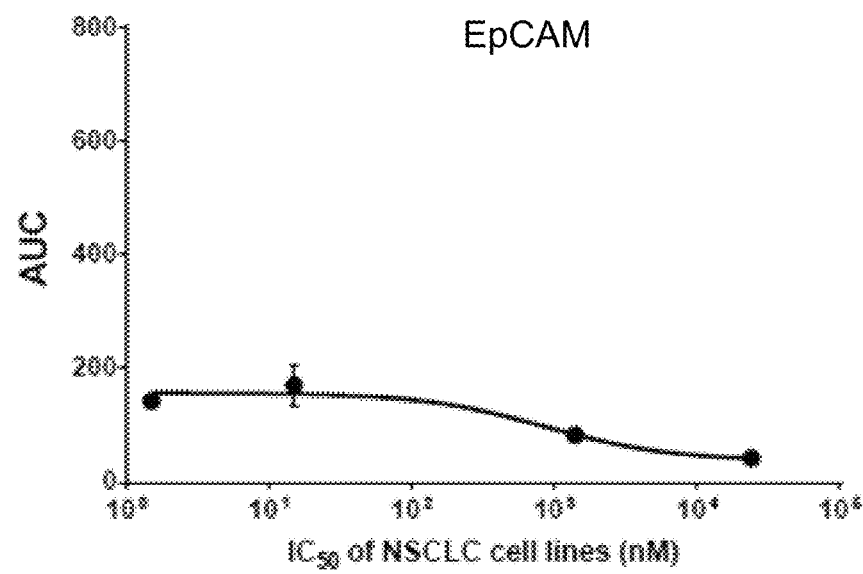
Figure 12F:
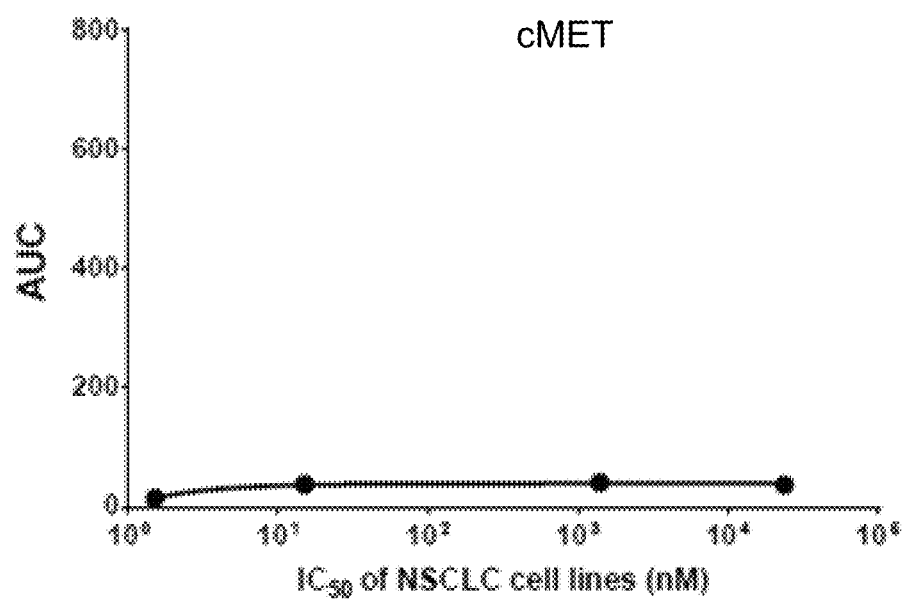

FIGS. 12A, B and C, demonstrate that treatment with Iressa® induces a time-dependent shedding of (A) PRDX6, (B) EpCAM and (C) cMET into the media for the NSCLC cell lines studied (H3255, HCC827, H1650, A431, H1975, H460). It was only with PRDX6, however, that a strong correlation was observed between total amount of biomarker shed and sensitivity to Iressa®. To quantify this relationship, the total area under the curve (AUC) of each time course of biomarker shedding for all of the cell lines studied and for all of the biomarkers taken into consideration were calculated and compared to the $IC_{50}$ to Iressa® of the corresponding cancer cell lines. The relationship between AUC and $IC_{50}$ to Iressa® were plotted (FIGS. 12D-12F) for PRDX6 (FIG. 12D), EpCAM (FIG. 12E), and cMET (FIG. 12F). The most significant correlation between total biomarker shed (as assessed by AUC) and $IC_{50}$ to Iressa® occurred with PRDX6 ($R^2$=0.79, $p<0.04$). Collectively, the data suggests that, thus far, PRDX6 is the only robust biomarker to track response to therapy of anti-tyrosine kinase drugs.

The invention claimed is:

1. A method of treating cancer in a subject, the method comprising:
determining a pre-treatment level of peroxiredoxin 6 (PRDX6) protein in a sample taken from a human subject having a cancer predicted to be sensitive to anti-epidermal growth factor receptor (EGFR) treatment, the cancer comprising cells with an EGFR mutation, wherein the pre-treatment sample is taken from the subject before or at the time of initiation of treatment with a tyrosine kinase inhibitor (TKI) anti-EGFR drug;
initiating a treatment regimen for the subject with a TKI anti-EGFR drug, wherein the subject receives one or more doses of the TKI anti-EGFR drug over a period of time;
determining a second level of PRDX6 in a second sample taken from the subject no later than about 4 weeks after the subject takes the initial dose of the TKI anti-EGFR drug;
creating a PRDX6 expression profile for the subject, wherein the PRDX6 expression profile compares the pre-treatment and second PRDX6 levels relative to the TKI anti-EGFR treatment regimen; and
continuing, modifying, or discontinuing the treatment regimen with the TKI anti-EGFR drug based on the PRDX6 expression profile, wherein:
treatment with the anti-EGFR drug is continued when the second level is at least 10% greater than the pre-treatment level of PRDX6 for the subject, indicating sensitivity to the anti-EGFR drug, or
treatment with the anti-EGFR drug is either discontinued or is continued by maintaining the dosage of the anti-EGFR drug or by increasing the amount of the drug subsequently administered to the subject when the second level is about the same as the pre-treatment level, about 10% less than the pre-treatment level, or less than about 10% greater than the pre-treatment level of PRDX6 for the subject, indicating potential non-responsiveness or resistance, and
optionally determining one or more subsequent levels of PRDX6 in subsequent samples taken from the subject after the second sample, wherein the pre-treatment sample, second sample and any subsequent samples comprise a sample selected from the group consisting of: blood, plasma, and sera; and
updating the PRDX6 expression profile for the subject to include any subsequent PRDX6 levels for evaluation of efficacy of the TKI anti-EGRF drug in reducing tumor volume.

2. The method of claim 1, wherein the second sample is taken from the subject between about 2 weeks and about 4 weeks after the initial treatment with the anti-EGFR drug.

3. The method of claim 1, wherein the cancer is selected from a group of cancers sensitive to anti-EGFR therapy consisting of: non-small cell lung cancer (NSCLC), colorectal cancer, pancreatic cancer, breast cancer, and prostate cancer.

4. The method of claim 1 wherein the anti-EGFR drug comprises an anti-EGFR drug selected from the group consisting of: gefitinib, erlotinib, and icontinib.

5. The method of claim 1, wherein determining a level of PRDX6 in a sample taken from the subject comprises performing an ELISA assay on the sample with a capture antibody specific for PRDX6 and a detection antibody capable of binding PRDX6.

6. The method of claim 5, wherein the capture antibody comprises sc-59671 and the detection antibody comprises ab73350.

7. The method of claim 1, comprising increasing the amount of the drug subsequently administered to the subject when the second PRDX6 level is about the same as the pre-treatment level, less than the pre-treatment level, or less than about 10% greater than the pre-treatment level of PRDX6 for the subject.

8. The method of claim 1, comprising continuing to treat the subject with the anti-EGFR drug when a third level of PRDX6, determined from a third sample taken from the subject about 2 weeks, or more, after the second sample, is about the same as the second level of PRDX for the subject or less than the second level of PRDX6 for the subject.

9. The method of claim 1, indicating possible resistance of the cancer to the anti-EGFR drug when the PRDX6 expression profile shows at least two consecutive PRDX6 levels after the second level within about 10% or less of each other, or when, after a third level that was lower than the second level, one or more subsequent levels after the third level are more than about 10% greater than the third level.

10. The method of claim 9, further comprising discontinuing the anti-EGFR drug when the PRDX6 expression profile indicates possible resistance to the anti-EGRF drug.

11. A method of treating cancer in a subject, the method comprising:
   a) determining a pre-treatment level of peroxiredoxin 6 (PRDX6) protein in a sample taken from a human subject having a cancer predicted to be sensitive to anti-epidermal growth factor receptor (EGFR) treatment, the cancer comprising cells with an EGFR mutation, wherein the pre-treatment sample is taken from the subject before or at the time of initiation of treatment with a tyrosine kinase inhibitor (TKI) anti-EGFR drug;
   b) initiating a treatment regimen for the subject with a TKI anti-EGFR drug, wherein the subject receives one or more doses of the TKI anti-EGFR drug over a period of time;
   c) determining a second level of PRDX6 in a second sample taken from the subject no later than about 4 weeks after the subject takes the initial dose of the TKI anti-EGFR drug;
   d) creating a PRDX6 expression profile for the subject, wherein the PRDX6 expression profile compares the pre-treatment and second PRDX6 levels relative to the TKI anti-EGFR treatment regimen; and
   e) continuing, modifying, or discontinuing the treatment regimen with the TKI anti-EGFR drug based on the PRDX6 expression profile, wherein:
      treatment with the anti-EGFR drug is continued when the second level is at least 10% greater than the pre-treatment level of PRDX6 for the subject, indicating sensitivity to the anti-EGFR drug, or
      treatment with the anti-EGFR drug is either discontinued or is continued by maintaining the dosage of the anti-EGFR drug or by increasing the amount of the drug subsequently administered to the subject when the second level is about the same as the pre-treatment level, about 10% less than the pre-treatment level, or less than about 10% greater than the pre-treatment level of PRDX6 for the subject, indicating potential non-responsiveness or resistance, and;
   f) optionally determining one or more subsequent levels of PRDX6 in subsequent samples taken from the subject after the second sample, wherein the pre-treatment sample, second sample and any subsequent samples comprise a sample selected from the group consisting of: blood, plasma, and sera;
   g) updating the PRDX6 expression profile for the subject to include any subsequent PRDX6 levels; and
   h) continuing, modifying, or discontinuing the treatment regimen with the TKI anti-EGFR drug based on the PRDX6 expression profile, wherein:
      when a third level of PRDX6, determined from a third sample taken from the subject about 2 weeks or more after the second sample, is about the same as the second level of PRDX6 for the subject or less than the second level of PRDX6 for the subject, sensitivity is indicated and treatment of the subject is continued with the anti-EGFR drug, or
      when two consecutive PRDX6 levels after the second level are within about 10% of each other or less, or when, after a third level that was lower than the second level, one or more subsequent levels after the third level are more than about 10% greater than the third level, possible tumor re-growth and possible resistance of the cancer to the anti-EGFR drug is indicated and treatment with the drug is discontinued or resistance by other tests is confirmed.

12. A method of determining sensitivity or resistance of a cancer in a human subject to a tyrosine kinase inhibitor (TKI) anti-epidermal growth factor receptor (EGFR) drug, the method comprising:
   determining a pre-treatment level of peroxiredoxin 6 (PRDX6) protein in a sample taken from a human subject having cancer comprising cells with an EGFR mutation, wherein the pre-treatment level is determined from a sample taken from the subject before or at the time of initiation of treatment with the TKI anti-EGFR drug;
   providing one or more doses of the TKI anti-EGFR drug to the subject over a period of time;
   determining a second level of PRDX6 in a second sample taken from the subject no later than about 4 weeks after the subject takes the initial dose of the TKI anti-EGFR drug, wherein the pre-treatment sample and second sample and any subsequent samples comprise a sample selected from the group consisting of: blood, plasma, and sera;
   creating a PRDX6 expression profile for the subject comparing the pre-treatment level of PRDX6 with the second level of PRDX6, relative to the TKI anti-EGFR treatment regimen; and
   determining sensitivity or potential non-responsiveness or resistance of the cancer to the anti-EGFR drug based on the PRDX6 expression profile, wherein:
   when the second level of PRDX6 is at least 10% greater than the pre-treatment level of PRDX6 for the subject, indicating sensitivity and continuing to treat the subject with the anti-EGFR drug, and
   when the second level is about the same as the pre-treatment level, about 10% less than the pre-treatment level, or less than about 10% greater than the pre-treatment level of PRDX6 for the subject, indicating potential non-responsiveness or resistance, and either discontinuing treatment with the anti-EGFR drug or continuing to treat the subject with the anti-EGFR drug by maintaining the dosage of the anti-EGFR drug or increasing the amount of the drug subsequently administered to the subject and determining one or more subsequent PRDX6 levels from the subject to confirm sensitivity or resistance.

13. The method of claim 12, comprising discontinuing treatment with the anti-EGFR drug when the second level is about the same as the pre-treatment level, about 10% less than the pre-treatment level, or less than about 10% greater than the pre-treatment level of PRDX6 for the subject.

14. The method of claim 12, comprising continuing to treat the subject with the anti-EGFR drug by maintaining the dosage of the anti-EGFR drug or increasing the amount of the drug subsequently administered to the subject to confirm sensitivity or resistance when the second level is about the same as the pre-treatment level, about 10% less than the pre-treatment level, or less than about 10% greater than the pre-treatment level of PRDX6 for the subject.

15. The method of claim 12, further comprising:
   determining one or more subsequent levels of PRDX6 in one or more subsequent samples taken from the subject, wherein the one or more subsequent samples are taken beginning about 6 weeks, or more, after the subject takes the initial dose of the TKI anti-EGFR drug;
   updating the PRDX6 expression profile based on the PRDX6 levels of the one or more subsequent samples;
   maintaining or increasing the amount of the anti-EGFR drug subsequently administered to the subject when the one or more subsequent levels of PRDX6 are about 10%, or more, less than the second level of PRDX6 for the subject; and
   wherein potential acquired resistance to anti-EGFR therapy is indicated when the one or more subsequent levels are the same or greater than the second level of PRDX6 for the subject.

* * * * *